(12) United States Patent
Kothari et al.

(10) Patent No.: US 10,478,400 B2
(45) Date of Patent: Nov. 19, 2019

(54) IMMEDIATE-RELEASE TABLETS CONTAINING COMBIMETINIB AND METHODS OF MAKING AND USING THE SAME

(71) Applicant: Genentech, Inc., South San Francisco, CA (US)

(72) Inventors: Sanjeev Kothari, Foster City, CA (US); Priscilla Mantik, San Jose, CA (US); Alexander Mauerer, Nuremberg (DE); Hamid Rezaei, San Ramon, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/852,125

(22) Filed: Dec. 22, 2017

(65) Prior Publication Data

US 2018/0116966 A1    May 3, 2018

Related U.S. Application Data

(63) Continuation of application No. PCT/US2016/039960, filed on Jun. 29, 2016.
(Continued)

(51) Int. Cl.
*A61K 9/20* (2006.01)
*A61K 9/28* (2006.01)
(Continued)

(52) U.S. Cl.
CPC .............. *A61K 9/2095* (2013.01); *A61J 3/10* (2013.01); *A61K 9/2018* (2013.01);
(Continued)

(58) Field of Classification Search
CPC .... A61K 9/2095; A61K 45/06; A61K 31/437; A61K 31/4523; A61K 9/1652;
(Continued)

(56) References Cited

U.S. PATENT DOCUMENTS

| | | | |
|---|---|---|---|
| 5,595,762 A * | 1/1997 | Derrieu | A61K 8/676 424/490 |
| 7,951,400 B2 * | 5/2011 | Desai | A61K 9/2086 424/472 |

(Continued)

FOREIGN PATENT DOCUMENTS

| WO | WO-2009120844 A2 * | 10/2009 | ........ A61K 9/2018 |
|---|---|---|---|
| WO | 2014/027056 A1 | 2/2014 | |
| WO | 2014/136048 | 9/2014 | |

OTHER PUBLICATIONS

Musib et al., "Absolute Bioavailability and Effect of Formulation Change, Food, or Elevated pH with Rabeprazole on Cobimetinib Absorption in Healthy Subjects," Molecular Pharmaceutics, 2013, 10, 4046-4054 (Year: 2013).*

*Primary Examiner* — Aradhana Sasan
(74) *Attorney, Agent, or Firm* — Genentech, Inc.; Richard G.A. Bone

(57) ABSTRACT

The present disclosure relates generally to rapid-release pharmaceutical dosage unit tablets containing a drug that is an inhibitor of the mitogen-activated protein kinase enzyme, a filler and a disintegrant, and to processes for forming the tablets. More specifically, the present disclosure relates to pharmaceutical dosage unit tablets containing cobimetinib, a least one filler, at least one lubricant and at least one disintegrant, and to methods for preparing the tablets from granules formed by dry granulation.

67 Claims, 21 Drawing Sheets

Related U.S. Application Data

(60) Provisional application No. 62/186,556, filed on Jun. 30, 2015.

(51) Int. Cl.
*A61K 31/4523* (2006.01)
*A61J 3/10* (2006.01)

(52) U.S. Cl.
CPC .......... *A61K 9/2054* (2013.01); *A61K 9/2077* (2013.01); *A61K 9/284* (2013.01); *A61K 31/4523* (2013.01)

(58) Field of Classification Search
CPC .... A61K 9/2018; A61K 9/1623; A61K 9/284; A61K 9/2054; A61K 9/2077; A61J 3/10
See application file for complete search history.

(56) References Cited

U.S. PATENT DOCUMENTS

| | | |
|---|---|---|
| 2010/0323005 A1 | 12/2010 | Seyer et al. |
| 2014/0093568 A1* | 4/2014 | Bray ................ G06Q 30/0241 424/482 |
| 2015/0038504 A1 | 2/2015 | Casteel et al. |
| 2018/0346442 A1* | 12/2018 | Brown ................ C07D 401/04 |

* cited by examiner

IMMEDIATE-RELEASE TABLETS CONTAINING COMBIMETINIB AND METHODS OF MAKING AND USING THE SAME

CROSS-REFERENCE TO RELATED APPLICATION

This application is a continuation of International Application No. PCT/US2016/039960, filed Jun. 29, 2016 which claims the benefit of priority to U.S. Provisional Application No. 62/186,556 filed Jun. 30, 2015, each of which are incorporated herein by reference in its entirety.

BACKGROUND

The field of the invention relates generally to pharmaceutical dosage unit tablets containing a drug and excipients, and processes for forming the tablets.

In some aspects of the disclosure, the drug is an inhibitor of the mitogen-activated protein kinase enzymes MEK1 and MEK2. Such MEK inhibitors are indicated for the treatment of patients with unresectable or metastatic melanoma with the BRAFV600 mutations. In some particular aspects of the disclosure, the drug is cobimetinib ([3,4-Difluoro-2-(2-fluoro-4-iodoanilino)phenyl]{3-hydroxy-3-[(2S)-piperidin-2-yl]azetidin-1-yl} methanone) and salts thereof. In yet other particular aspects of the disclosure, the drug is crystalline hemifumarate salt of (S)-[3,4-Difluoro-2-(2-fluoro-4-iodoanilino)phenyl]{3-hydroxy-3-[(2S)-piperidin-2-yl] azetidin-1-yl} methanone) designated as Form A.

Immediate-release compressed tablets (e.g., caplets) are an effective form for delivering pharmaceutically active drugs. Compressed tablets often involve multiple steps in order to incorporate pharmaceutically active agents into the form since only certain materials (excipients) may be suitable for compression. The drug active and excipients must have the correct compression characteristics such as flow and compressibility in order to maintain operability on a tablet press, retain shape and form without breakage, and dissolve within an appropriate timeframe in the gastrointestinal tract.

Problematically, some combinations of drugs, fillers and disintegration agents (to impart rapid release properties) have poor compression characteristics thereby presenting mechanical strength and dissolution issues for tablets prepared by dry granulation and tablet compression methods.

A need therefore exists for improved tablet compositions containing a drug, a filler and a disintegration agent and related preparation methods that allow for tablets having both (1) sufficient hardness to resist breakage, chipping and abrasion and (2) adequate dissolution and disintegration characteristics required for immediate-release tablets.

BRIEF DESCRIPTION

In some aspects of the disclosure, a process for preparing a pharmaceutical dosage unit tablet core is provided. The process comprises blending a particulate pharmaceutical active drug, an intragranular filler, an intragranular disintegrant and an intragranular lubricant to form a pre-blend, wherein the particulate pharmaceutical active drug has a particle size D[v, 0.5] of from about 25 µm to about 65 µm, from about 25µ to about 50 µm, or from about 30µ to about 40 µm. The pre-blend is compacted by application of a roller compaction force of from about 1 kN/cm to about 8 kN/cm, from about 2 kN/cm to about 5 kN/cm or from about 2 kN/cm to about 4 kN/cm. The compacted pre-blend is milled and screened to form granules. In some particular aspects of the disclosure, the pre-blend is compacted between at least two rotating rolls having a gap width of from about 2 mm to about 5 mm, from about 2 mm to about 4 mm, from about 3 mm to about 5 mm or from about 4 mm to about 5 mm to form a ribbon, and the ribbon is milled and screened to form granules. The granules are tableted by application of a tableting compression force of from about 5 kN to about 20 kN, from about 14 kN to about 19 kN, from about 14 kN to about 18 kN, or from about 8 kN to about 13 kN to form the pharmaceutical dosage unit tablet core.

In some other aspects of the disclosure, a pharmaceutical dosage unit tablet core is provided. The tablet core comprises: (1) about 5 wt. % or more of a particulate pharmaceutical active drug; (2) a lubricant at a content based on the pharmaceutical dosage unit tablet core weight of from about 0.5 wt. % to about 5 wt. %, from about 0.5 wt. % to about 3 wt. %, from about 1 wt. % to about 3 wt. %, from about 1 wt. % to about 2.5 wt. %, or from about 1.5 wt. % to about 2 wt. %; (3) a disintegrant at a content based on the pharmaceutical dosage unit tablet core weight of from about 2 wt. % to about 7 wt. %, from about 2 wt. % to about 6 wt. %, from about 2 wt. % to about 5 wt. %, from about 3 wt. % to about 6 wt. % or from about 3 wt. % to about 5 wt. %; (4) a filler at a content based on the pharmaceutical dosage unit tablet core weight of from about 60 wt. % to about 78 wt. %, from about 65 wt. % to about 78 wt. %, from about 65 wt. % to about 77 wt. %, from about 70 wt. % to about 77 wt. %, or from about 71 wt. % to about 75 wt. %; and (5) optionally, up to 10 wt. % of a binder.

In other aspects of the disclosure, a pharmaceutical dosage unit tablet core is provided. The tablet core comprises: (1) 18.5 wt. % cobimetinib hemifumarate polymorph Form A; (2) 45.6 wt. % microcrystalline cellulose; (3) 30.4 wt. % lactose monohydrate; (4) 4 wt. % croscarmellose sodium; and (5) 1.5 wt. % magnesium stearate.

In other aspects of the disclosure, a coated pharmaceutical dosage unit tablet core is provided. The coated table comprises: (1) 17.79 wt. % cobimetinib hemifumarate polymorph Form A; (2) 43.85 wt. % microcrystalline cellulose; (3) 29.23 wt. % lactose monohydrate; (4) 3.84 wt. % croscarmellose sodium; (5) 1.45 wt. % magnesium stearate; and (6) 3.85 wt. % film coating.

In other aspects of the disclosure, a process for preparing a coated pharmaceutical dosage unit tablet is provided. The process comprises the following steps: (1) combining a particulate filler component, a first particulate disintegrant component and a particulate active drug component in a blender and admixing said components to form a primary pre-blend; (2) combining a particulate first lubricant component with the primary pre-blend in a blender and admixing said first lubricant component and primary pre-blend to form a finished pre-blend; (3) dry granulating the finished pre-blend to form granules; (4) combining the granules and a second particulate disintegrant component in a blender and admixing said granules and disintegrant component to form a primary final blend; (5) combining a second particulate lubricant component and the primary final blend in a blender and admixing said second lubricant component and primary final blend to form a finished final blend; (6) tableting the final blend to form tablet cores; and (7) coating the tablet cores. In some aspects of the disclosure, a film-coat solid mixture is suspended in water to form a coating mixture slurry and the tablet cores are coated with the coating mixture slurry to form the coated pharmaceutical dosage unit tablet.

In still other aspects of the disclosure, a pharmaceutical product is provided. The product comprises (1) a first tablet comprising cobimetinib and (2) a second tablet comprising propane-1-sulfonic acid {3-[5-(4-chlorophenyl)-1H-pyrrolo[2,3-b]pyridine-3-carbonyl]-2,4-difluoro-phenyl}-amide (vemurafenib), or a pharmaceutically acceptable salt thereof. The first tablet and the second tablet comprise a combined preparation for concurrent or sequential use in the treatment of BRAFV600 mutation positive unresectable or metastatic melanoma. One or more first tablets are administered to provide a total dose of 60 mg cobimetinib, on days 1-21 of a 28 day cycle, and one or more second tablet are administered to provide a total dose of 960 mg vemurafenib, twice daily each day of the 28 day cycle.

In yet other aspects of the disclosure, the pharmaceutical product recited above is used in the manufacture of a medicament for treatment of BRAF$^{V600}$ mutation-positive unresectable or metastatic melanoma.

In other aspects of the disclosure, a kit is provided. The kit comprises (1) a first tablet comprising cobimetinib and (2) a second tablet comprising vemurafenib, or a pharmaceutically acceptable salt thereof.

DETAILED DESCRIPTION

In accordance with some aspects of the present disclosure, there is provided, as described herein, pharmaceutical dosage form tablets comprising at least 5 weight percent ("wt. %") of an active drug, a filler, a disintegrant and a lubricant wherein the tablets exhibit rapid dissolution rate, rapid disintegration time, sufficient hardness to resist table chipping or crumbling during packaging and storage, and sufficient abrasion resistance to resist erosion or chipping during coating. In accordance with some other aspects of the present disclosure, there is provided, as described herein, a processes for preparing the pharmaceutical dosage form tablets comprising an active drug from granules.

In some aspects of the disclosure, the active drug is cobimetinib. Special reference is made in the description to the active drug cobimetinib, however, the compositions, formulations and processes disclosed herein are applicable to and encompass active drugs other than cobimetinib.

Figure 1:
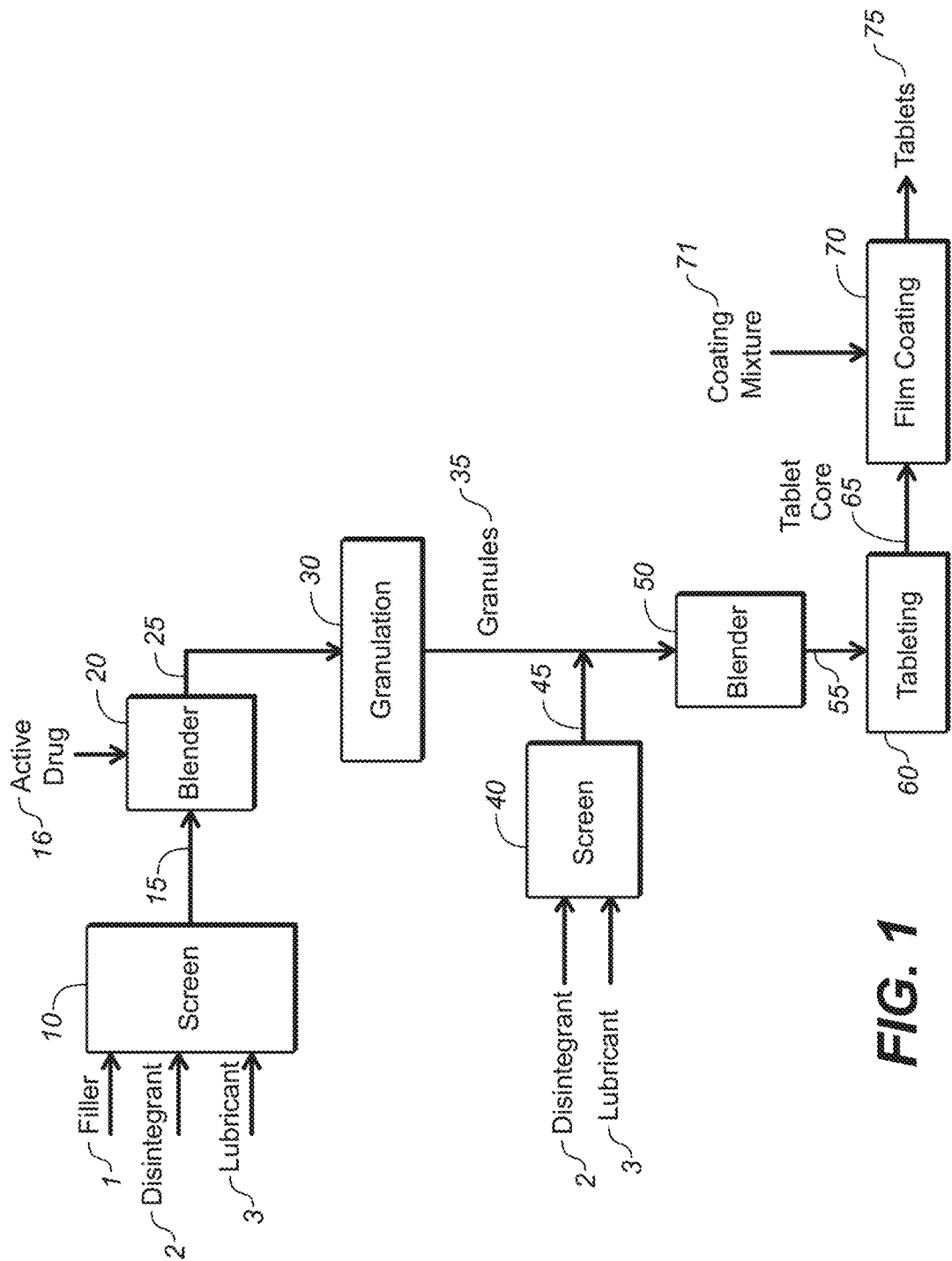
FIG. 1 depicts a first tableting process of the present disclosure.

One process of the present disclosure is depicted in FIG. 1. As depicted, filler 1, disintegrant 2 and lubricant 3 are delumped by passing through screen 10 to form delumped pre-blend material 15. Delumped pre-blend material 15 is combined with active drug 16 in blending apparatus 20 and admixed to form pre-blend 25. Pre-blend 25 is granulated in granulation apparatus 30 (e.g., by granulation, milling and screening) to form granules 35. The filler 1, disintegrant 2 and lubricant 3 are present in granules 35 as intragranular components. Disintegrant and lubricant 3 are delumped by passing through screen 40 to form delumped material 45 that is combined with granules 35 in blending apparatus 50 and admixed to form final blend 55. Final blend 55 is tableted in tableting apparatus 60 to form core tablets 65. Core tablets 65 are coated with coating mixture 71 in film coating apparatus 70 to form coated tablets 75.

As used herein, intragranular refers to a component that is added prior to granulation such that the component is incorporated within the granules. As further used herein, extragranular refers to a component that is combined with the granules prior to compression, such as in a tablet press.

Figure 2:
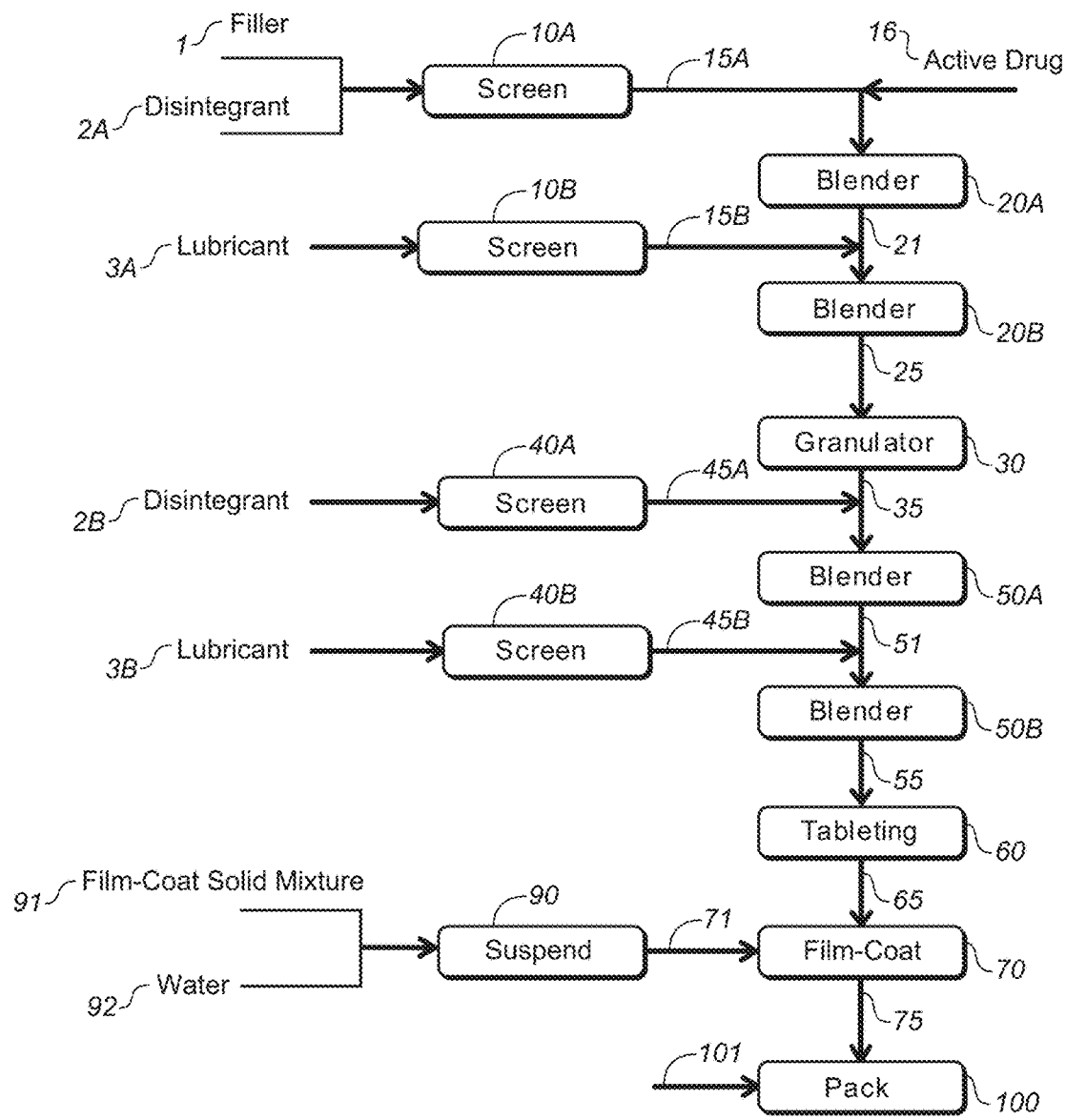
FIG. 2 depicts a second tableting process of the present disclosure.

Another process of the present disclosure is depicted in FIG. 2. As depicted, filler 1 and disintegrant 2A are delumped by passing through screen 10A to form stream 15A that is added to blender apparatus 20A. Active drug 16 is added to blender apparatus 20A. Stream 15A and active drug 16 are then admixed to form primary pre-blend 21.

Lubricant 3A is delumped by passing through screen 10B to form stream 15B that is combined with primary pre-blend 21 in blender apparatus 20B. Stream 15B and first pre-blend 21 are then admixed to form pre-blend 25. In some aspects of the disclosure, screen 10A and screen 10B are the same apparatus and in other aspects of the disclosure screen 10A and screen 10B are different apparatuses. In yet further aspects of the disclosure, blender 20A and blender 20B are the same apparatus and in other aspects of the disclosure blender 20A and blender 20B are different apparatuses. Pre-blend 25 is dry granulated in granulator apparatus 30 (e.g., by granulation, milling and screening) to form granules 35. Disintegrant 2B is delumped by passing through screen 40A to form stream 45A that is combined with granules 35 in blender apparatus 50A. Stream 45A and granules 35 are then admixed to form primary final blend 51. Lubricant 3B is delumped by passing through screen 40B to form stream 45B that is combined with primary final blend 51 in blender apparatus 50B. Stream 45B and primary final blend 51 are then admixed to form final blend 55. In some aspects of the disclosure disintegrant 2A and disintegrant 2B are the same compound and in other aspects of the disclosure disintegrant 2A and disintegrant 2B are different compounds. In some further aspects of the disclosure lubricant 3A and lubricant 3B are the same compound and in other aspects of the disclosure lubricant 3A and lubricant 3B are different compounds. In some aspects of the disclosure, screen 40A and screen 40B are the same apparatus and in other aspects of the disclosure screen 40A and screen 40B are different apparatuses. In some aspects, screen 10A and screen 40A are the same screen and screen 10B and screen 40B are the same screen. In yet further aspects of the disclosure, blender 50A and blender 50B are the same apparatus and in other aspects of the disclosure blender 50A and blender 50B are different apparatuses. Final blend 55 is tableted in tableting apparatus 60 to form core tablets 65. Film-coat solid mixture 91 is combined with water 92 and suspended in suspending apparatus 90 to form film-coating mixture 71. Core tablets 65 are coated with coating mixture 71 in film coating apparatus 70 to form coated tablets 75. Coated tablets are then packaged in containers 101 in packing apparatus 100.

Figure 11:
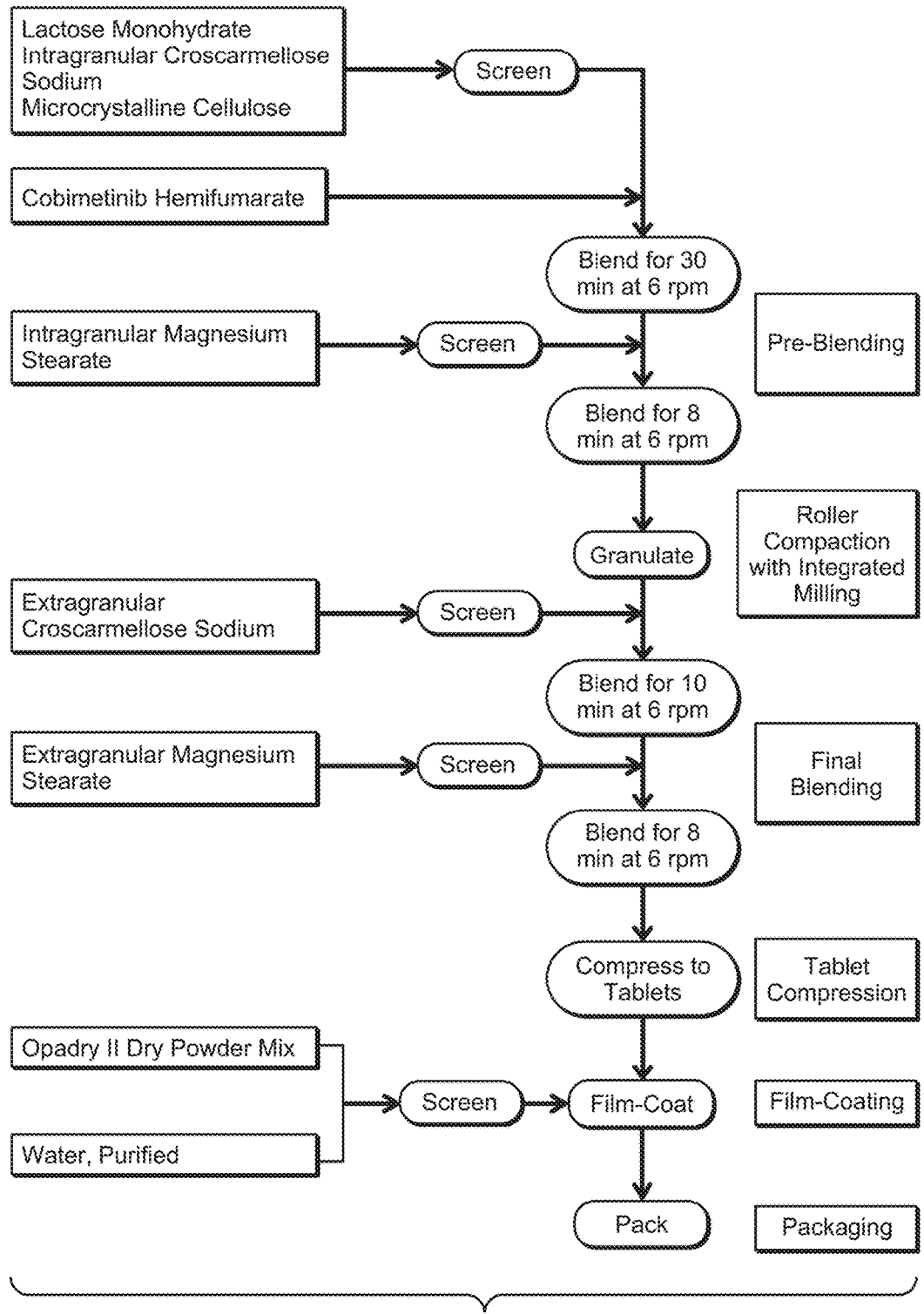
FIG. 11 depicts a third tableting process of the present disclosure.

One particular manufacturing aspect of the present disclosure is depicted in FIG. 11 and comprises pre-blending, granulating/milling and screening, final blending, tableting, and coating steps.

Referring to FIG. 11, a pre-blend is formed in two steps. In a first step, intragranular lactose monohydrate, intragranular croscarmellose sodium, and intragranular microcrystalline cellulose are screened for delumping and charged to a blender. Delumping may be done by methods known to those skilled in the art such as passing the material through a 1.0 mm mesh screen as using a vibratory sifter or an in-line sifter. Cobimetinib hemifumarate Form A is then charged to the blender, and the blender contents are admixed at a blending speed of 6 rpm for 30 minutes. Suitable blenders and blender loading is as described in more detail elsewhere herein. In a second step, intragranular magnesium stearate is screened for delumping through a 0.5 mm mesh screen and charged to the blender, and the contents are admixed at a blending speed of 6 rpm for 8 minutes to produce the pre-blend. In some such aspects, a pre-blend batch suitable for producing 420,000 tablets is manufactured wherein the pre-blend comprises 22.982 kg microcrystalline cellulose, 15.322 kg lactose monohydrate, 1.008 kg croscarmellose sodium and 0.126 kg magnesium stearate.

Referring again to FIG. 11, the pre-blend is dry-granulated by roller compaction, milled and screened through a 1 mm screen as described in more detail elsewhere herein. In some such aspects, for an active drug having a particle size D [v, 0.5] less than 38 μm, the roller compaction force is set at 2 kN/cm and the gap size is 5 mm. In some other such aspects, for an active drug having a particle size D [v, 0.5] of at least 38 μm, the roller compaction is set at from 2 kN/cm to 4 kN/cm and the gap size is from 4 mm to 5 mm.

Referring again to FIG. 11, a final blend is formed in two steps. In a first step, extragranular croscarmellose sodium is screened through a 1.0 mm screen for delumping as described above and combined with the granulate in a blender. The blender contents are admixed at a blending speed of 6 rpm for 10 minutes. In a second step, extragranular magnesium stearate is screened through a 0.5 mm screen for delumping and charged to the blender, and the contents are admixed at 6 rpm for 8 minutes to form the final blend. In aspects wherein a final blend batch suitable for producing 420,000 tablets is manufactured, the amount of extragranular croscarmellose sodium is 1.008 kg and the amount of extragranular magnesium stearate 0.63 kg.

Again referring to FIG. 11, the final blend is compressed in a press, such as a rotary tableting press, at a main compression force of from 14 kN to 19 kN to form tablet cores. The tablet cores are coated by spraying with a coating suspension using a pan coating apparatus known in the art. In some such aspects, wherein a final blend batch suitable for producing 420,000 tablets is manufactured, the coating suspension comprises 0.806 kg polyvinyl alcohol, 0.504 kg titanium dioxide, 0.407 kg Macrogol/PEG 3350, 0.298 kg talc and a suitable amount of purified water to form the coating suspension. In some other such aspects, the coating composition is Opadry II White 85F18422. Batch sizes other than those suitable for preparing 420,000 tablets may be prepared with the same ratios of ingredients.

Tablet Component Description

Active Drug

The tablet compositions of the present disclosure comprise about 5 wt. % or more active drug, such as about 5 wt. %, about 10 wt. %, about 15 wt. %, about 20 wt. %, about 25 wt. %, about 30 wt. % or about 35 wt. %, and ranges thereof, such as from about 5 wt. % to about 35 wt. %, from about 10 wt. % to about 30 wt. % or from about 15 wt. % to about 25 wt. %. In some aspects of the present disclosure the active drug is cobimetinib free base or a salt thereof. In some other aspects, the active drug is cobimetinib hemifumarate. Cobimetinib hemifumarate is anhydrous, crystalline, is known to exist in a single polymorphic Form A, and exhibits a high melting point of from about 233 to 241° C. and low hygroscopicity. Cobimetinib, preparative methods, and therapeutic uses are disclosed in International Publication Numbers WO 2007/044515, WO 2007/044615, WO 2014/027056 and WO 2014/059422, each of which is incorporated herein by reference. Cobimetinib is considered to be a high-solubility, moderate-to-high permeability compound with in vivo absorption/pharmacokinetic characteristics consistent with Biopharmaceutics Classification System (BCS) Class 1. The 24-hour solubility results for cobimetinib hemifumarate active drug in a range of buffers across the physiological pH range, at 37° C., are presented in Table A below. An active drug is considered highly soluble when the highest dose strength is soluble in <250 mL water over a pH range of 1 to 7.5.

TABLE A

| pH | Buffer | Solubility (mg/mL) | pH measured |
| --- | --- | --- | --- |
| Neutral | Water | 0.72 | 7.5 |
| 6.5 | FaSSIF | 0.48 | 6.4 |
| 5.0 | FeSSIF | 4.13 | 5.0 |
| 1.1 | 0.1M HCl | 48.21 | 1.9 |
| 4.5 | 50 mM Acetate | 1.08 | 4.5 |
| 6.8 | 50 mM Phosphate | 0.78 | 6.8 |
| 7.5 | 50 mM Phosphate | 0.73 | 7.5 |

FaSSIF = fasted-state simulated intestinal fluid; FeSSIF = fed-state simulated intestinal fluid.

Cobimetinib, compound (I) in scheme 1, can be prepared as described in WO 2014/059422 and as generally depicted in Scheme 1. Reaction of commercially available (3 S,5R, 8a5)-3-phenyl-hexahydro-oxazolo[3,2-a]pyridine-carbonitrile (VII) with commercially available tert-butyl-3-oxo-1-azetidinecarboxylate (VIIa) in the presence of base provides compound (VI). Compound (VI) is treated with a hydride reducing agent such as sodium cyanoborohydride in the presence of acid, followed by treatment with aqueous sodium hydroxide, to provide compound (V). Deprotection of compound (V) using acid gives compound (IV), which is coupled to acid chloride (Iva) in the presence of a catalytic amount of pyridine to provide compound (III). Hydrogenation of compound (III) yields piperidine derivative compound (II). Finally, coupling of compound (II) with 2-fluoro-4-iodo aniline (IIa) yields cobimetinib.

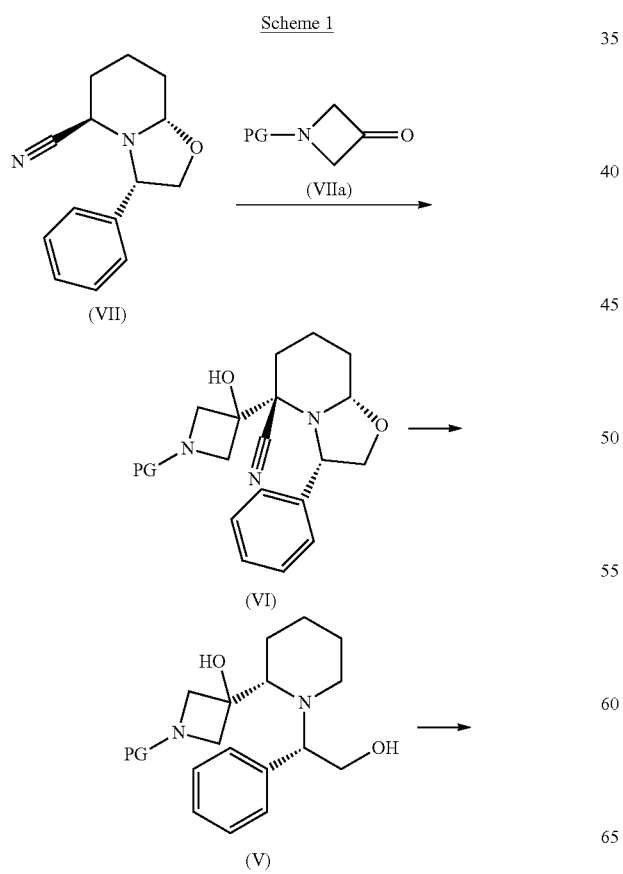

Scheme 1

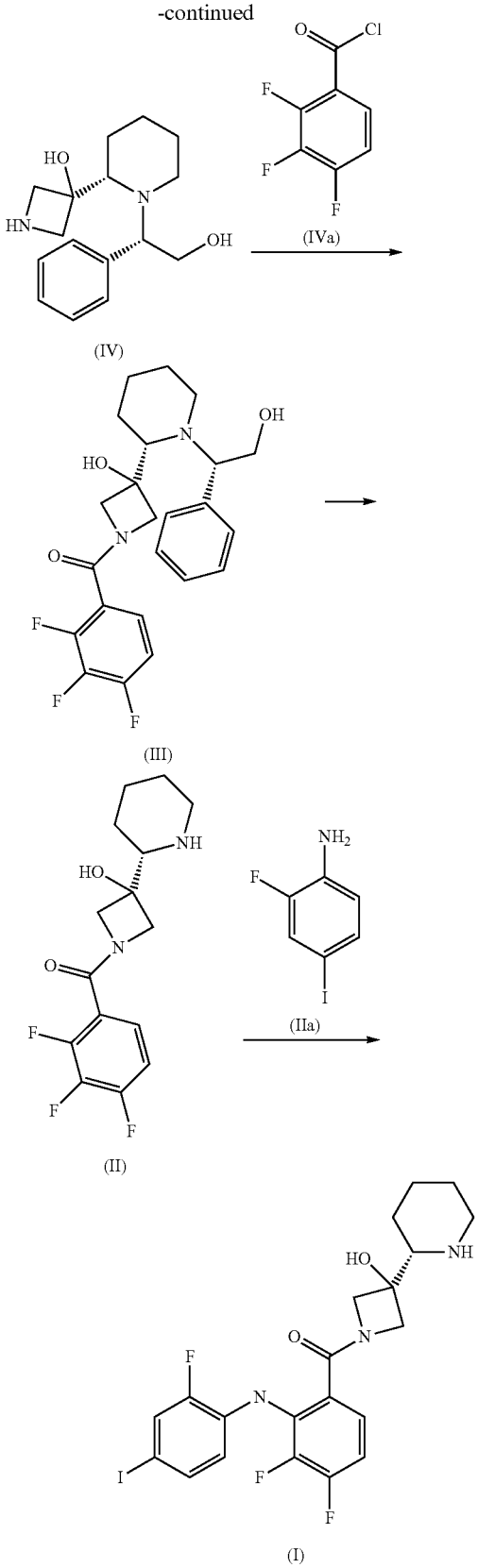

Various salts of cobimetinib are known including salts prepared from benzoic acid, malonic acid, fumaric acid, mandelic acid, acetic acid, and orotic acid. In some aspects of the disclosure, the salt is the hemifumarate salt wherein one molecule of fumaric acid forms a salt with two molecules of cobimetinib. Thus, about 0.50, about 0.51, about 0.52 or about 0.53, or from about 0.51 to about 0.5 equivalents of fumaric acid are used for every one equivalent of cobimetinib to form the hemifumarate salt.

Crystalline forms of cobimetinib hemifumarate may be prepared by a variety of methods including, but not limited to, for example, crystallization or recrystallization from a suitable solvent mixture; sublimation; growth from a melt; solid state transformation from another phase; crystallization from a supercritical fluid; and jet spraying. Techniques for crystallization or recrystallization of crystalline forms of a solvent mixture include, but are not limited to, for example, evaporation of the solvent; decreasing the temperature of the solvent mixture; crystal seeding of a supersaturated solvent mixture of the compound and/or salt thereof; crystal seeding a supersaturated solvent mixture of the compound and/or a salt from thereof; freeze drying the solvent mixture; and adding anti-solvents (counter-solvents) to the solvent mixture. High throughput crystallization techniques may be employed to prepare crystalline forms including polymorphs.

In some aspects of the disclosure for the preparation of cobimetinib hemifumarate polymorph Form A, cobimetinib is dissolved in a solvent; fumaric acid is dissolve in a solvent; the cobimetinib solution is combined with the fumaric acid solution to form crystalline cobimetinib hemifumarate polymorph Form A; and the crystals are collected. In some aspects of the disclosure, the solvents are polar solvents. Depending on the solubility of fumaric acid and/or cobimetinib in a particular solvent, gentle heating (40-80° C.) may be necessary to ensure complete dissolution. For example, fumaric acid can be dissolved in a protic such as an alcohol (for example, methanol, ethanol, n-propanol or isopropanol or the like, alone or as a mixture with one more other solvents or with water. Alternatively, fumaric acid can be dissolved in an aprotic solvent such as tetrahydrofuran, dichloromethane, or the like. Similarly, cobimetinib can be dissolved in dichloromethane or a polar solvent such as an alcohol (for example, methanol, ethanol, n-propanol or isopropanol or the like, alone or as a mixture with one more other solvents or with water. The solution of fumaric acid is then added to the solution of cobimetinib and the resulting mixture is allowed to stand until a precipitate forms. In some instances, to expedite crystal formation, the resulting mixture is cooled or a seed crystal is added. In other instances, an anti-solvent such as a nonpolar hydrocarbon solvent such as heptane or the like is used to expedite crystal formation.

In some other aspects of the disclosure for the preparation of cobimetinib hemifumarate polymorph Form A, cobimetinib is dissolved in a first solvent to form a first mixture; fumaric acid is dissolved in a second solvent to form a second mixture; the first and second mixtures are combined with cooling to form the crystals as a precipitate; and the crystals of the crystalline cobimetinib hemifumarate polymorph Form A are collected. As in the previous aspect, the solvents that are employed are polar solvents. In a particular embodiment, the first and second solvents are the same and are a mixture of isopropanol and water. In one embodiment, the ratio of isopropanol to water is 9:1. In another embodiment, the ratio of isopropanol to water is 4:1. In another embodiment, the ratio of isopropanol to water is 85:15. Typically, approximately 7 to 11 weight equivalents of the first solvent are used for every one weight equivalent of cobimetinib, and 2.0 to 3.0 weight equivalents of the second solvent are used for every one weight equivalent of fumaric acid. More particularly, approximately 8 to 10 weight equivalents of the first solvent are used for every one weight equivalent of cobimetinib, and 2.4 to 2.7 weight equivalents of the second solvent are used for every one weight equivalent of fumaric acid.

In some particular aspects, cobimetinib solution is filtered (e.g., thorough activated carbon) and thereafter slowly combined with fumaric acid solution with gentle heating at a temperature of about 40-90° C.; more preferably 60-85° C.; and more preferably 75-80° C. In some instances, seeding crystals may be added to the mixture of cobimetinib and fumaric acid in a propanol/water solvent. To complete the crystallization process, the mixture can be cooled to approximately 20° C. The resulting crystals may be isolated by filtration or centrifugation.

In some further aspects of the disclosure for the preparation of cobimetinib hemifumarate polymorph Form A, cobimetinib is dissolved in a first solvent to form a first mixture; fumaric acid is dissolved in a second solvent to form a second mixture; the first and second mixtures are combined wherein the crystalline cobimetinib hemifumarate polymorph Form A is formed by precipitation. In some such aspects, the process further comprises adding seed crystals of the cobimetinib hemifumarate polymorph Form A to the mixture.

In still further aspects of the disclosure for the preparation of cobimetinib hemifumarate polymorph Form A, amorphous cobimetinib hemifumarate is dissolved in a solvent with gentle heating at 65-80° C. and cooled to form crystals. In one embodiment, cobimetinib hemifumarate polymorph Form A seed crystals can be added to the mixture. In another embodiment, the mixture can be cooled to approximately 20° C. In any such aspect, the resulting crystals are may be isolated by filtration or centrifugation.

Figure 15:
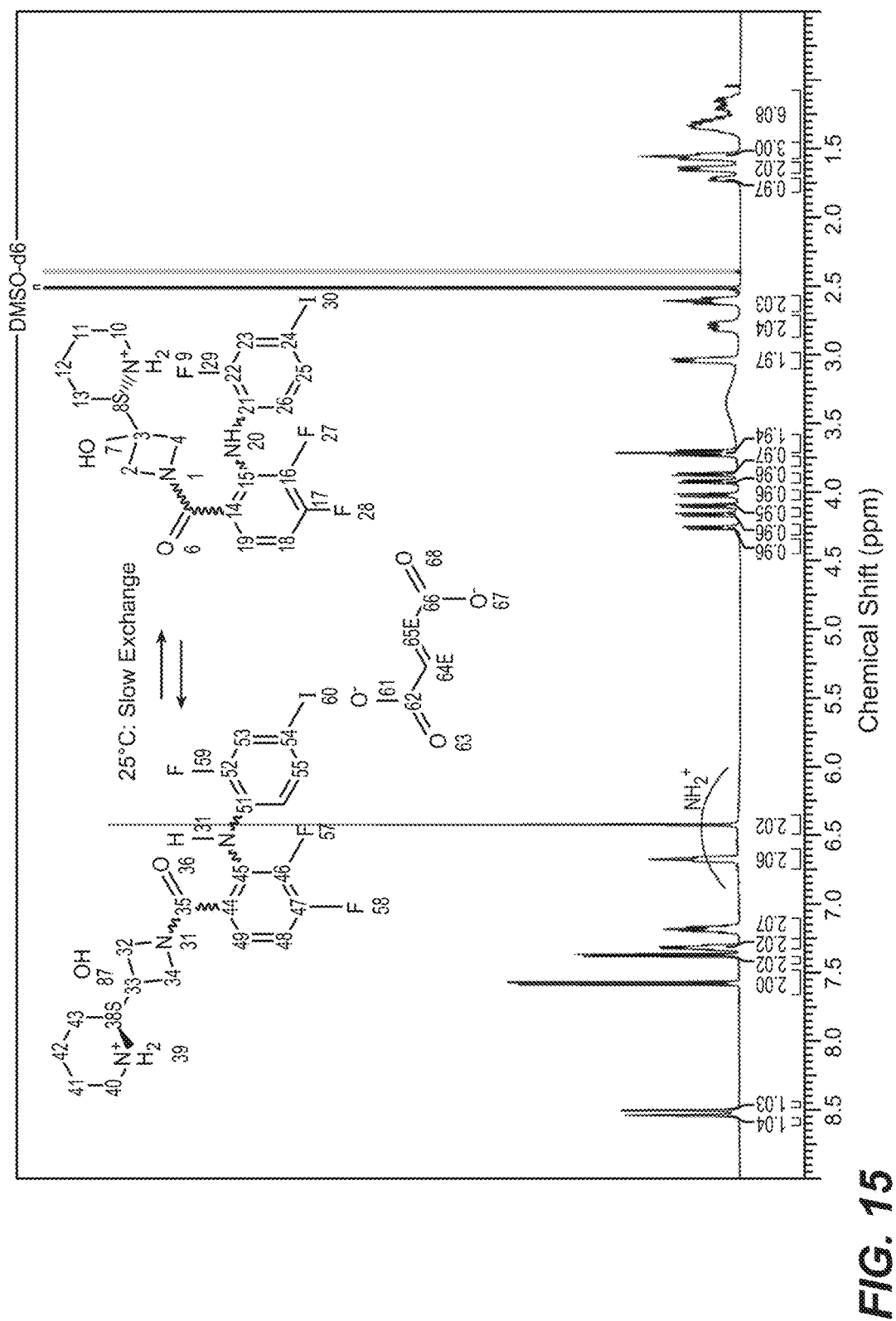
FIG. 15 is a $^1$H NMR spectrum of cobimetinib hemifumarate polymorph Form A in $d_6$ DMSO.
Figure 16:
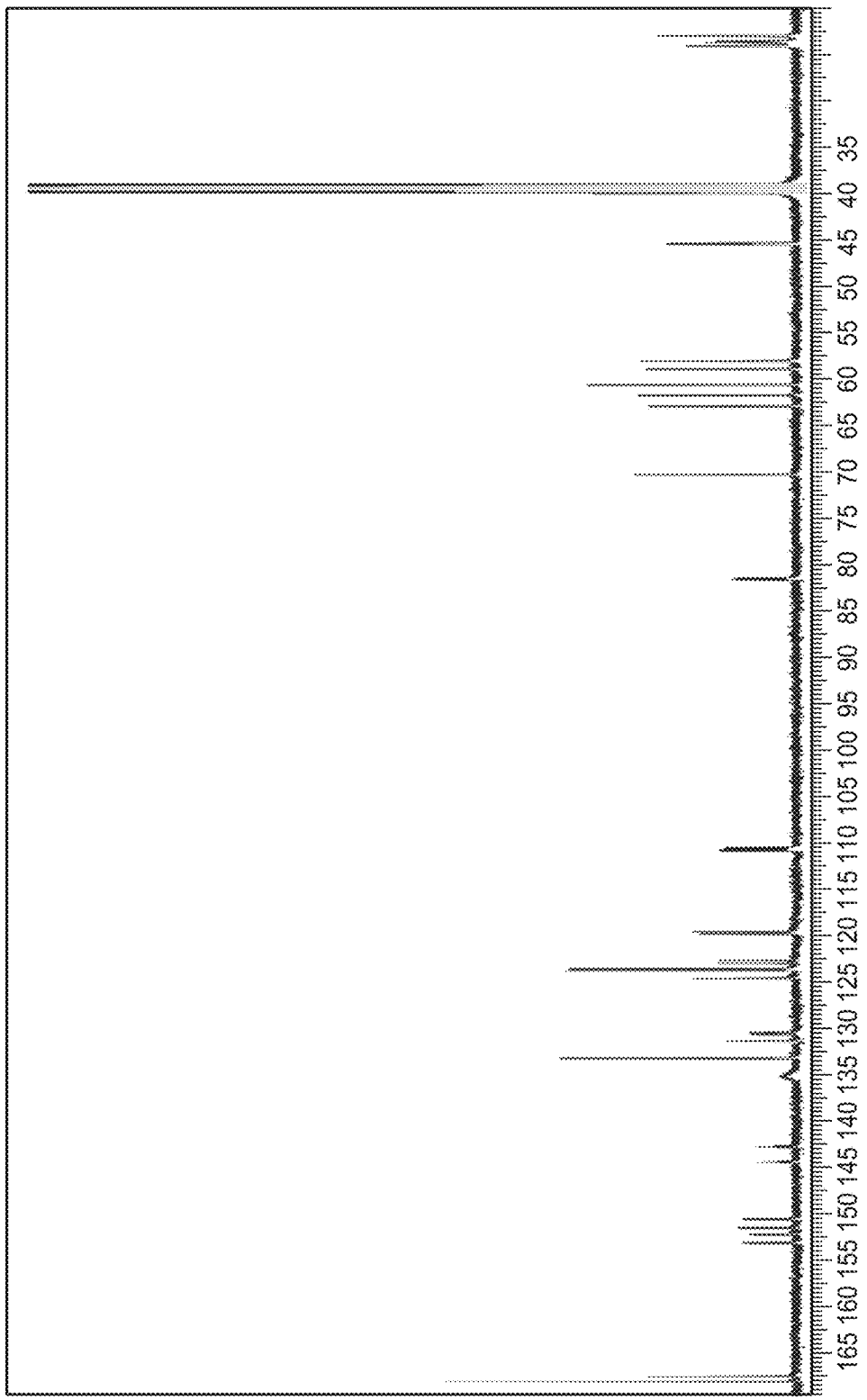
FIG. 16 is a $^{13}$C NMR spectrum of cobimetinib hemifumarate polymorph Form A in $d_6$ DMSO.
Figure 17:
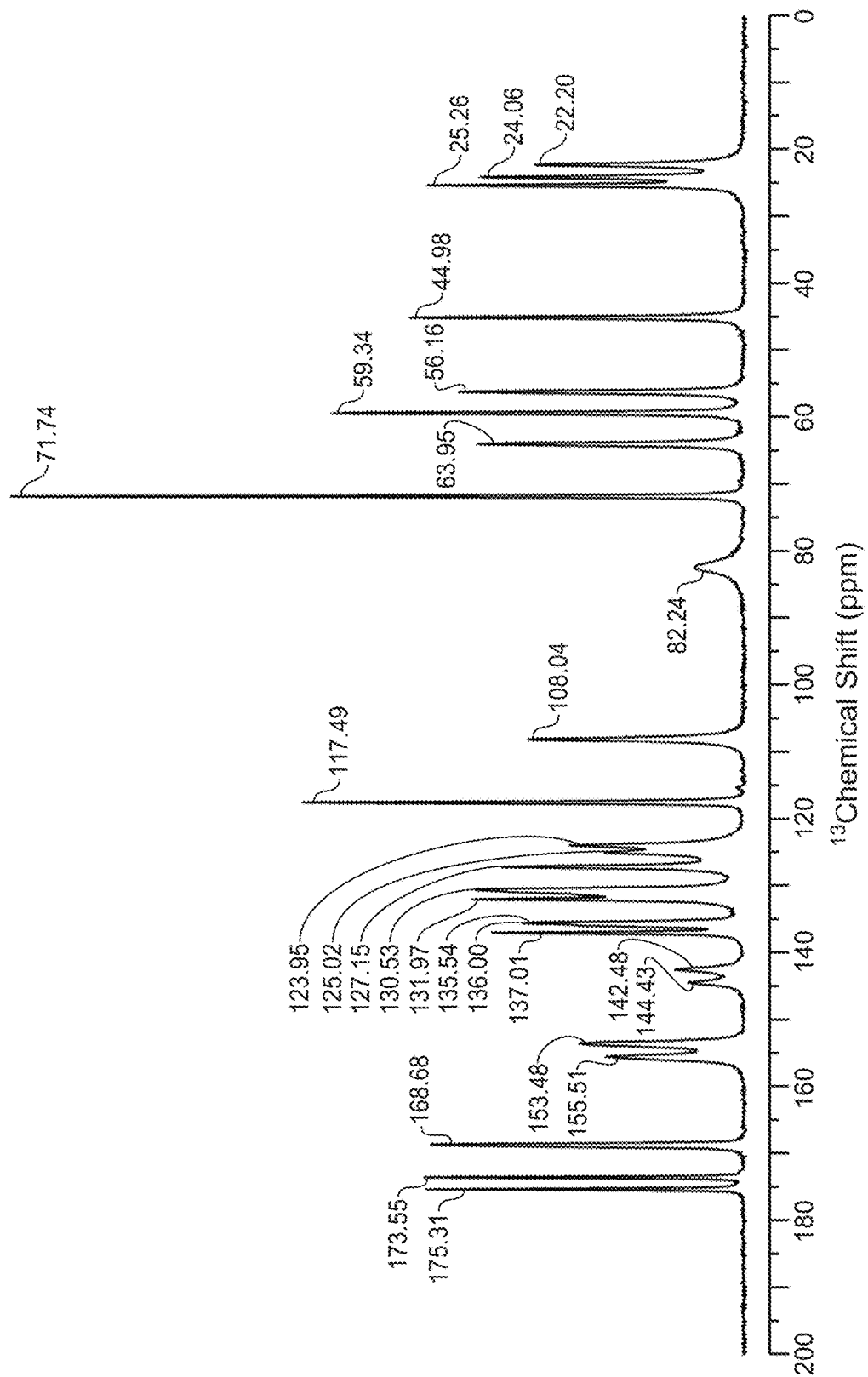
FIG. 17 is a solid state $^{13}$C NMR spectrum of cobimetinib hemifumarate polymorph Form A.

In some aspects of the disclosure, the crystalline hemifumarate salt of (S)-[3,4-difluoro-2-(2-fluoro-4-iodophenylamino)phenyl] [3-hydroxy-3-(piperidin-2-yl) azetidin-1-yl-methanone designated as Form A is characterized by one, two three, four, or five peaks selected from 175.3, 173.6, 117.5, 155.5, and 153.5, ±0.2 ppm in the solid state $^{13}C$ Nuclear magnetic resonance (NMR) spectrum. In some other aspects of the disclosure, said salt is characterized by one, two three, four, or five peaks selected from 4.6, 12.1, 13.2, 13.6 and 14.5±0.2 °2θ in the x-ray diffraction pattern (CuKα λ=1.5418 Å). In some other aspects, said salt is characterized by a $^1H$ NMR spectrum in $d_6$ DMSO substantially as depicted in FIG. 15. In still other aspects, said salt is characterized by a 13C NMR spectrum in $d_6$ DMOS substantially as depicted in FIG. 16. In yet other aspects, said salt is characterized by a solid state $^{13}C$ NMR spectrum substantially as depicted in FIG. 17. NMR measurements may suitably be done on Bruker Avance 600 and 400 MHz spectrometers wherein the 600 MHz machine may be equipped with a 5 mm, TCI, z-gradient CryoProbe and the 400 MHz machine may be equipped with a 5 mm, BBFO, z-gradient Probe. A sample may be prepared by dissolving 6 mg of the crystalline fumarate salt of cobimetinib designated as Form A in 0.75 mL DMSO-d6 (D, 99.8%) for all proton detected experiments. For $^{13}C$-NMR and $^{19}F$-NMR, 62 mg may be dissolved in 0.75 mL DMSO-d6.

Figure 18:
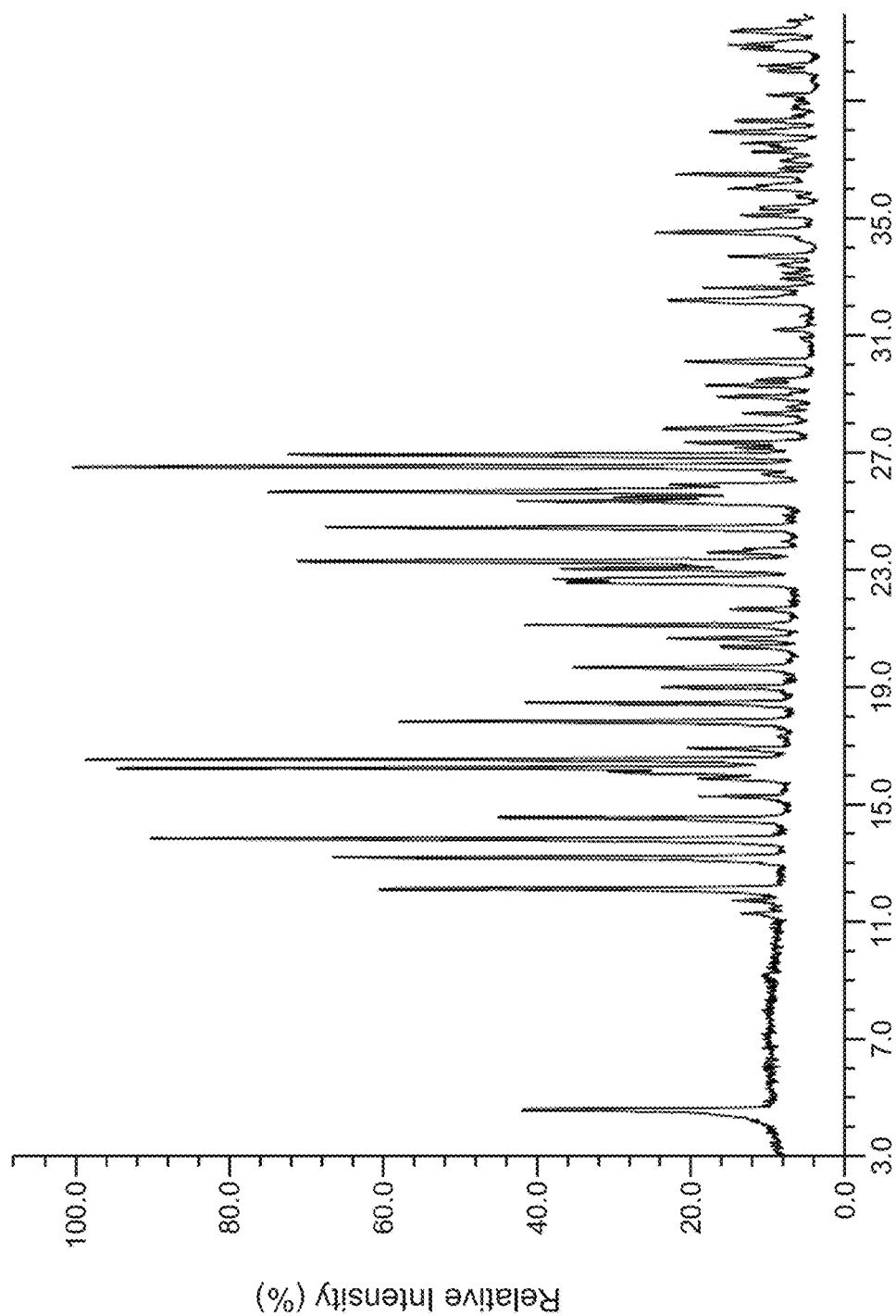
FIG. 18 is an x-ray powder diffraction pattern of cobimetinib hemifumarate polymorph Form A.

In still other aspects, said salt is characterized by a x-ray powder diffraction (XRPD) pattern substantially in accordance with the pattern shown in FIG. 18. XRPD measurements may be done using a single crystal mounted in a loop and measured at ambient temperature. Data may be collected at the Swiss Light Source beamline X10SA equipped with a DECTRIS Pilatus 6M detector with synchrotron radiation and data processed with the program XDS. The crystal structure may be solved and refined with She1XTL (Bruker AXS, Karlsruhe). In some such aspects, XRD patterns may recorded at ambient conditions in transmission geometry with a STOE STADI P diffractometer (Cu K α radiation [1.54 Å], primary monochromator, silicon strip detector, angular range 3° to 42° 2-θ, approximately 30 minutes total measurement time).

Figure 19:
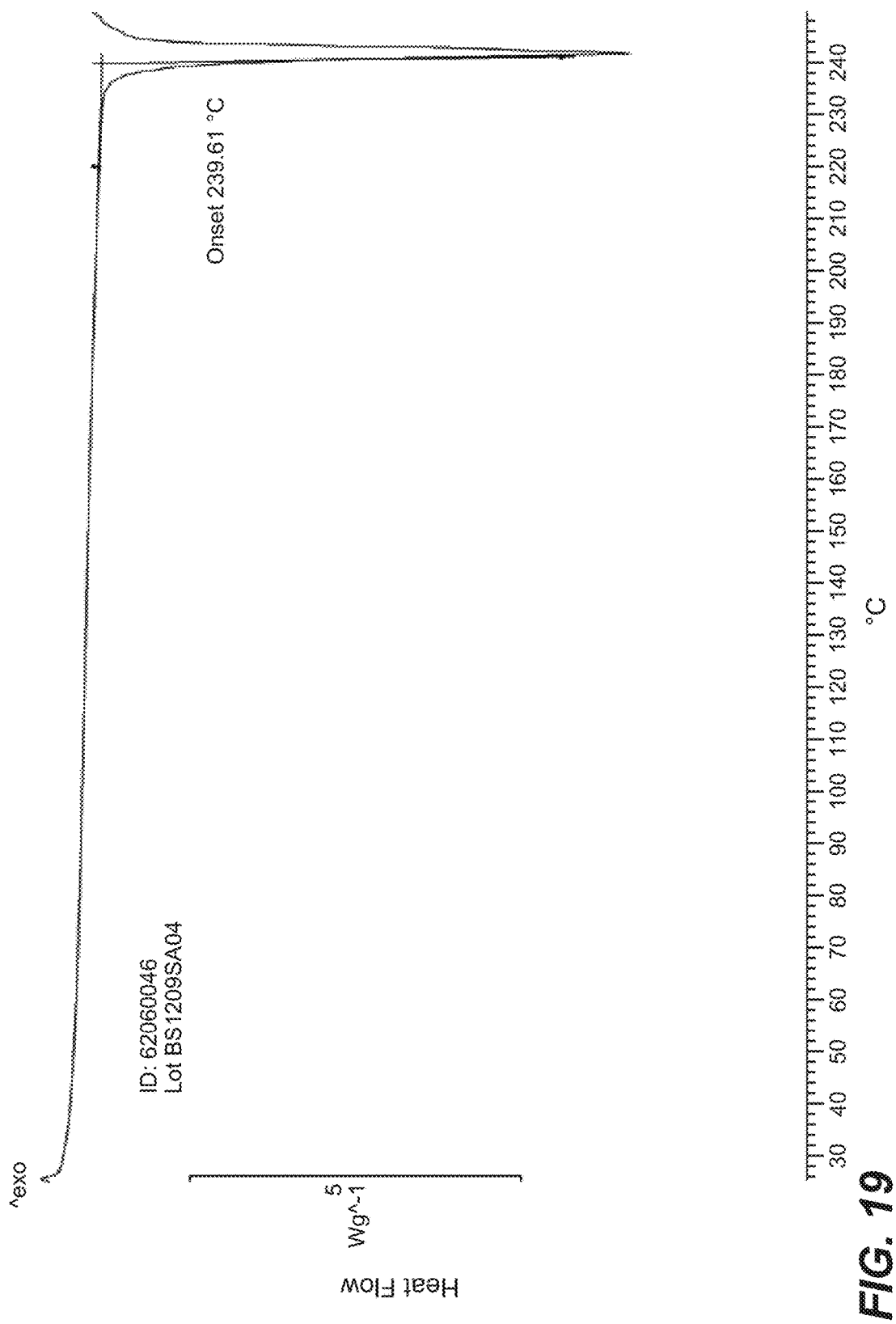
FIG. 19 is a differential scanning calorimetry thermogram of cobimetinib hemifumarate polymorph Form A.

In yet other aspects, said salt is characterized by a differential scanning calorimetry (DSC) thermogram substantially in accordance with FIG. 19. DSC thermograms may be recorded using a Mettler-Toledo instrument (DSC820/821e/1; FRS05 sensor) wherein about 2-6 mg of a sample may be placed in aluminum pans and sealed with aluminum lids. Lids are automatically pierced prior to heating and the samples are heated under nitrogen at a rate of 10 K/min to a maximum of 250° C.

In still other aspects, said salt is characterized by unit cell parameters approximately equal to the following: (1) Crystal System: Tetragonal; (2) Space Group: P43212; (3) Crystal Habit: Plates; (4) Unit Cell Dimensions: a=7.8825 Å, b=7.8825 Å, c=76.846 Å, α=90°, β=90°, γ=90°; (5) Temperature: 293K; (6) Cell Volume 4774.7 A; (7) Molecules in Cell: 8; and (8) Density: 1.637 g/cm$^3$.

Based on experimental evidence to date, it has been discovered that active drug particle size distribution ("PSD") can impact content and uniformity of dosage tablets through an influence on processability during tablet compression (blend flowability, tablet weight, and main compression force variability) and on tablet appearance. In particular, PSD has been discovered to affect stickiness to process equipment and varying flow properties.

An active drug with a small D [v, 0.5] has been discovered to lead to tablet appearance defects, which could have an impact on patient compliance. Based on experimental evidence to date, it has been discovered that a lower limit for active drug D [v, 0.5] of about 25 µm, in combination with control of roller compaction gap size and force (as described in more detail herein) and in further combination with main compression force during tablet compression unit operations (as described in more detail herein) allows for acceptable appearance of the film-coated tablets. It has been further discovered that a positive trend with respect to drug product processability and tablet appearance results from increasing active drug particle size. Based in experimental evidence to date, increasing the active drug particle size to a particle size defined by D [v, 0.9] of about 100 µm, results in a positive trend with respect to drug product processability to appearance. It is believed however that acceptable drug product processability and tablet appearance may be achieved at D [v, 0.9] of about 150 µm, about 200 µm, about 250 µm, about 300 µm, about 350 µm, about 400 µm, about 450 µm or about 500 µm. As used herein D [v, 0.5] represents the size value of a particle at which 50% of a sample of a plurality of particles is below. Alternatively stated, D [v, 0.5] refers to the median particle diameter. D [v, 0.9] represents the size value of a particle at which 90% of a sample of a plurality of particles is below.

In accordance with the present disclosure, D [v, 0.5] is about 25 µm, about 30 µm, about 35 µm, about 40 µm, about 45 µm, about 50 µm, about 55 µm, about 60 µm, or about 65 µm, and ranges thereof, such as from about 25 µm to about 65 µm, from 27 µm to about 65 µm, from about 40 µm to about 65 µm, from about 25 µm to about 50 µm, from 27 µm to about 50 µm, from about 25 µm to about 40 µm, from about 30 µm to about 40 µm, or from 32 µm to 38 µm.

In further accordance with the present disclosure, D [v, 0.9] is about 45 µm, about 50 µm, about 55 µm, about 60 µm, about 65 µm, about 70 µm, about 75 µm, about 80 µm, about 85 µm, about 90 µm, or about 95 µm, about 100 µm, about 150 µm, about 200 µm, about 250 µm, about 300 µm, about 350 µm, about 400 µm, about 450 µm or about 500 µm, and ranges thereof, such as from about 45 µm to about 500 µm, from about 45 µm to about 400 µm, from about 45 µm to about 300 µm, from about 45 µm to about 200 µm, from about 45 µm to about 100 µm, from 44 µm to about 100 µm, from about 50 µm to about 60 µm, from 49 µm to 56 µm, from about 65 µm to about 100 µm, from about 45 µm to about 80 µm, from 44 µm to 77 µm, from about 75 µm to about 100 µm, or from 77 µm to about 100 µm.

Active drug particle size may suitably be measured by laser diffraction methods known in the art. In some such methods, a MasterSizer 2000 or MasterSizer 3000 laser diffraction instrument (Malvern Instruments), a Hydro 2000S, Hydro 2000S$^+$ or Hydro MV (Malvern Instruments) dispersion unit, and a dispersion medium comprising an n-heptane solution of 5 g/L Span85 are suitable for measurement of particle size distribution. The instrument software calculates the cumulative undersize plot according to the Fraunhofer theory. The cumulative undersize plot Q3 (X) indicates the standardized proportion (as a volume/volume percentage) of particles (based on the total amount) that are smaller than particle diameter X.

Filler

The tablets of the present disclosure comprise fillers. The fillers are used for direct compression (tableting) of the granules of the present disclosure prepared by dry granulation, and constitute the major component of the present tablets. Fillers are known in the art and include, for instance and without limitation, sugars and sugar alcohols, cellulosics, and other fillers. Non-limiting examples of suitable sugars and sugar alcohols include dextrates, dextrin, dextrose, lactose, maltodextrin, mannitol, isomalt, sorbitol, sucrose, sugars spheres, xylitol, fructose, lactitol, erythritol, maltitol, xylose, glucose, mannose, galactose, maltose, cellobiose, trehalose and raffinose. Non-limiting examples of cellulosics include microcrystalline cellulose ("MCC") and silicified MCC. Non-limiting examples of other fillers include calcium carbonate, calcium sulphate, calcium silicate, chitin, chitosan, dibasic calcium phosphate dihydrate, glyceryl palmitostearate, hydrogenated vegetable oil, kaolin, magnesium aluminum silicate, magnesium carbonate, magnesium oxide, polymethacrylates, potassium chloride, powdered cellulose, pregelatinized starch, sodium chloride, starch, talc, and di- and tri-basic calcium phosphate. In some aspects of the disclosure, the filler is lactose, MCC, silicified MCC, di-basic calcium phosphate, mannitol, isomalt, pregelatinized starch, and combinations thereof.

Figure 3:
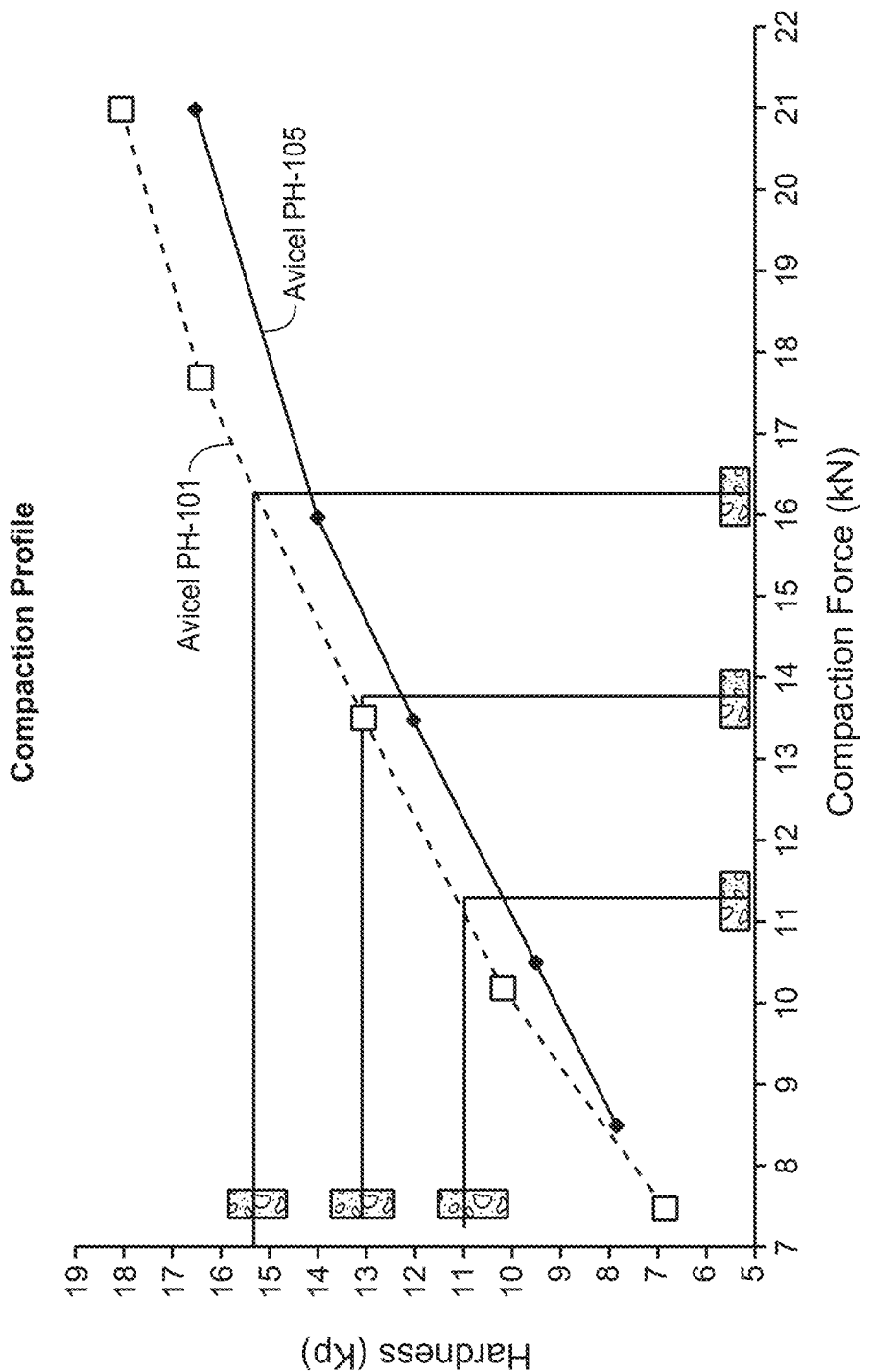
FIG. 3 is a graphical representation of a compaction profile of cobimetinib hemifumarate in combination with microcrystalline cellulose grades PH-101 and PH-105.

In some particular aspects, the filler is lactose (e.g., lactose monohydrate), MCC, and combinations thereof. Based on experimental results to date, it has been discovered that lactose monohydrate loading and its ratio to MCC may have an effect on the amount of fines present in the granulation, hence affecting tablet crushing strength and processability. In some aspects of the disclosure, the total filler content and the ratio of lactose to MCC is controlled in a ratio determined experimentally to optimize the mechanical properties of the active drug and tablets formed therefrom. MCC undergoes plastic deformation on compression. MCC in the formulation is combined with the more brittle excipient lactose monohydrate in an optimized ratio, which helps to manage the mechanical properties of the active drug. The ratio of lactose to MCC is about 4:1 about 3.5:1, about 3:1, about 2.5:1, about 2:1, about 1.5:1, about 1:1, about 1:1.25 or about 1:1.5 and ranges thereof, such as from about 1:1.5 to about 4:1, from about 1.25 to about 4:1, from about 1:1 to about 4:1 from about 1:1 to about 3:1, from about 1.5:1 to about 3:1 or from about 2:1 to about 2.5:1. Non-limiting examples of MCC include Avicel® grades PH-101, PH-102, PH-105 and PH-200 available from FMC Biopolymer. In some particular aspects, the MCC is grade PH-101 having a bulk density of from 0.26 to 0.31, a degree of polymerization of not more than 350, and a particle size (air jet) of not more than 1 wt. %+60 mesh (250 microns) and not more than 30 wt. %+200 mesh (75 microns). that has been demonstrated to provide for some improvement compactability as compared to other grades, such as PH-105. See FIG. 3 that depicts the experimental results of compactability testing of two cobimetinib formulations of the present disclosure containing Avicel® PH-101 and Avicel® PH-105, respectively, wherein the results indicate that tablet compactability is improved through use of Avicel® PH-101. It is further believed that MCC grade PH-101 provides for improved flow and a lower angle of repose as compared to other MCC grades.

Total filler content based on tablet core weight is about 60 wt. %, about 61 wt. %, about 62 wt. %, about 63 wt. %, about 64 wt. %, about 65 wt. %, about 66 wt. %, about 67 wt. %, about 68 wt. %, about 69 wt. %, about 70 wt. %, about 71 wt. %, about 72 wt. %, about 73 wt. %, about 74 wt. %, about 75 wt. %, about 76 wt. %, about 77 wt. % or about 78 wt. %, and ranges thereof, such as from about 60 wt. % to about 78 wt. %, from about 65 wt. % to about 78 wt. %, from about 65 wt. % to about 77 wt. %, from about 70 wt. % to about 78 wt. %, from about 70 wt. % to about 77 wt. %, or from about 71 wt. % to about 75 wt. %.

Disintegrant

Disintegrant is used to ensure rapid disintegration of the tablet. This is achieved through rapid swelling when in contact with aqueous media. Disintegrant may suitably be added to the pre-blend prior to granulation thereby forming intragranular disintegrant. Additionally, disintegrant may be combined with granulated pre-blend prior to tableting thereby forming extragranular disintegrant. Disintegrants are known in the art. Non-limiting examples include: modified starches such as sodium carboxymethyl starch (sodium starch glycolate); cross-linked polyvinylpyrrolidones such as crospovidone; modified celluloses such as croscarmellose sodium; cross-linked alginic acid; gums such as gellan gum and xanthan gum; calcium silicate. In some aspects of the disclosure, the disintegrant is croscarmellose sodium, crospovidone, sodium starch glycolate, and combinations thereof. In some aspects of the disclosure, the disintegrant is croscarmellose sodium, sodium starch glycolate, and combinations thereof.

Total tablet disintegrant loading based on tablet core weight may be about 1 wt. %, about 2 wt. %, about 3 wt. %, about 4 wt. %, about 5 wt. %, about 6 wt. %, or about 7 wt. %, and ranges thereof, such as from about 1 wt. % to about 7 wt. %, from about 2 wt. % to about 7 wt. %, from about 2 wt. % to about 6 wt. %, from about 2 wt. % to about 5 wt. %, from about 3 wt. % to about 6 wt. % or from about 3 wt. % to about 5 wt. %. Total tablet intragranular disintegrant loading may be about 0.1 wt. %, about 0.25 wt. %, about 0.5 wt. %, about 0.75 wt. %, about 1 wt. %, about 1.5 wt. %, about 2 wt. %, about 2.5 wt. %, or about 3 wt. %, and ranges thereof, such as from about 0.1 wt. % to about 3 wt. %, from about 0.25 wt. % to about 2.5 wt. %, from about 0.25 wt. % to about 2 wt. %, from about 0.25 wt. % to about 1.5 wt. %, from about 0.25 wt. % to about 1 wt. %, from about 0.5 wt. % to about 3 wt. %, from about 0.5 wt. % to about 2 wt. %, from about 0.5 wt. % to about 1.5 wt. %, from about 1 wt. % to about 3 wt. %, or from about 1 wt. % to about 2.5 wt. %. Total tablet extragranular disintegrant loading may be about 0.5 wt. %, about 1 wt. %, about 1.25 wt. %, about 1.5 wt. %, about 2 wt. %, about 2.5 wt. %, or about 3 wt. %, and ranges thereof, such as from about 0.5 wt. % to about 3 wt. %, from about 1 wt. % to about 3 wt. %, from about 1.25 wt. % to about 3 wt. %, from about 1.25 wt. % to about 2.5 wt. %, from about 1.25 wt. % to about 2 wt. %, from about 1.25 wt. % to about 1.5 wt. %, from about 1.5 wt. % to about 3 wt. %, or from about 1.5 wt. % to about 2.5 wt. %. Alternatively stated, in aspects of the disclosure directed to the combination of intra and extragranular disintegrant, the weight ratio of the intragranular disintegrant to the extragranular disintegrant is about 1:5, about 1:3, about 1:1 or about 2:1. Based on experimental results to date, it is believed that higher disintegrant levels produced tablets with relatively shorter disintegration times and reduced tablet hardness.

Lubricant

Lubricants are added to compositions for tableting in order to reduce the friction between the surfaces of manufacturing equipment and that of organic solids in the tablet composition, promote ejection from the tablet press, affect the dynamics of dry granulation and tableting processes, and affect the mechanical properties of tablets. Lubricants may suitably be added to the pre-blend prior to granulation thereby forming intragranular lubricant. Additionally, lubricants may be combined with granulated pre-blend prior to tableting thereby forming extragranular lubricant. Lubricants and known in the art. Non-limiting examples include magnesium stearate, calcium stearate, stearic acid, sodium stearyl fumarate, hydrogenated vegetable oils, polyethylene glycol (4000-6000), and sodium lauryl sulfate. In some aspects of the disclosure, the lubricant is magnesium stearate, sodium stearyl fumarate, and combinations thereof.

Total tablet lubricant loading, on a tablet core basis, may be about 0.5 wt. %, about 1 wt. %, about 1.5 wt. %, about 2 wt. %, about 2.5 wt. %, about 3 wt. %, about 3.5 wt. %, about 4 wt. %, about 4.5 wt. % or about 5 wt. %, and ranges thereof, such as from about 0.5 wt. % to about 5 wt. %, from about 0.5 wt. % to about 4 wt. %, from about 0.5 wt. % to about 3 wt. %, from about 1 wt. % to about 5 wt. %, from about 1 wt. % to about 4 wt. %, from about 1 wt. % to about 3 wt. %, from about 1 wt. % to about 2.5 wt. %, or from about 1.5 wt. % to about 2 wt. %. Total tablet intragranular lubricant loading may be about 0.1 wt. %, about 0.15 wt. %, about 0.2 wt. %, about 0.25 wt. %, about 0.3 wt. %, about 0.4 wt. %, about 0.5 wt. %, about 0.75 wt. %, or about 1 wt. %, and ranges thereof, such as from about 0.1 wt. % to about 1 wt. %, from about 0.2 wt. % to about 0.75 wt. % or from about 0.25 wt. % to about 5 wt. %. Total tablet extragranular lubricant loading may be about 0.5 wt. %, about 0.75 wt. %, about 1 wt. %, about 1.25 wt. %, about 1.5 wt. %, about 1.75 wt. %, about 2 wt. %, about 2.25 wt. % or about 2.5 wt. %, and ranges thereof, such as from about 0.5 wt. % to about 2.5 wt. %, from about 0.75 wt. % to about 2.25 wt. %, from about 0.75 wt. % to about 2 wt. %, from about 1 wt. % to about 1.75 wt. % or from about 1.25 wt. % to about 1.5 wt. %. In some particular aspects, the lubricant is present intragranularly at levels ranging from 0.25% to 0.50% and extragranularly at levels ranging from 1.25% to 1.50% at a total loading 1.5% to 2.0%.

Tablet Coating

The tablets of the present disclosure (tablet cores) are preferably coated with a film-coating to provide for tablets that are predominantly tasteless and odorless, and are easy to swallow. Further, film coating prevents dust formation during packaging and ensures robustness during transportation. Commercial coating compositions are suitable for purposes of the present disclosure and include Opadry® YS-1-7003, Opadry® YS-1-18202, Opadry® II White 85F18422. In any of the various coating aspects, the surface of the tablet core is coated with from about 2 wt. % to about 6 wt. %, from about 3 wt. % to about 5 wt. % or from about 4 wt. % to about 5 wt. % of a film-coating based on the weight of the table core. In some aspects of the disclosure the film coating comprises: from about 30 wt. % to about 50 wt. %, from about 35 wt. % to about 45 wt. % or from 38 wt. % to 42 wt. % of a coating agent (e.g., polyvinyl alcohol); from about 20 wt. % to about 30 wt. % or from 23.8 wt. % to 26.3 wt. % of a pigment (e.g., titanium dioxide); from about 15 wt. % to about 25 wt. % or from 19.2 wt. % to 21.2 wt. % of a plasticizer (e.g., Macrogol/PEG3350); and from about 10 wt. % to about 20 wt. % or from 14.1 wt. % to 15.5 wt. % of an anticaking agent (e.g., talc).

Optional Components

The tablet cores of the present disclosure may optionally comprise a binder to promote the bonding and cohesiveness of granules and tablets and function to improve hardness. Binders are known in the art. Non-limiting examples include partially pregelatinized starch, hydroxypropyl cellulose, methyl cellulose, hydroxypropyl methyl cellulose ("HPMC"), copovidone, and povidone. In some aspects, the binder is copovidone, povidone, HMP, pregelatinized starch, and combinations thereof. In some further aspects, the binder is copovidone. The binder is generally present as an intragranular component at a total content based on tablet weight of about 1 wt. %, about 2 wt. %, about 3 wt. %, about 4 wt. %, about 5 wt. %, about 6 wt. %, about 7 wt. %, about 8 wt. %, about 9 wt. % or about 10 wt. %, up to about 10 wt. %, up to about 8 wt. %, up to about 6 wt. %, and ranges thereof, such as from about 1 wt. % to about 10 wt. %, from about 1 wt. % to about 8 wt. %, from about 1 wt. % to about 7 wt. %, from about 1 wt. % to about 6 wt. % or from about 1 wt. % to about 5 wt. %.

Other optional table core components include talc (an antiadherent/glidant), fumed silicon dioxide (an antiadherent/glidant), citric acid (a pH adjuster) and tartaric acid (a pH adjuster)

Tableting Manufacturing Process

The tableting manufacturing process of the present disclosure utilize standard and conventional pharmaceutical operations, such as screening, blending, dry granulation, compression, and film coating.

In one process of the present disclosure depicted in FIG. 1, filler, disintegrant, lubricant and binder (optional—not depicted in FIG. 1) are screened and combined with an active drug in a blender to form a pre-blend. In some optional aspects, the filler and disintegrant are screened, combined with the active drug and blended for a first blend period followed addition of screened lubricant and a blending in a second blend period to form the pre-blend. The filler, disintegrant and lubricant in the pre-blend are termed intragranular. The pre-blend is then processed by roller compaction followed, milling and screening to form a granulate. The granulate is combined with additional screened lubricant and screened filler and blended to form a tableting blend. In some optional aspects, the granulate is combined with screened disintegrant and blended for a first period followed by addition of screened lubricant and blending in a second blend period to form the tableting blend. The disintegrant and lubricant combined with the granulate are termed extragranular. The tableting blend is compressed using any suitable tableting apparatus known in the art to form tablet cores. The table cores are coated with a film coating to form the finished tablets.

In one particular process of the present disclosure depicted in FIG. 2, intragranular filler (e.g., lactose monohydrate, croscarmellose sodium and/or microcrystalline cellulose) and disintegrant (e.g., croscarmellose sodium and/or sodium starch glycolate) are screened and combined with active drug and admixed (blended) in a first pre-blending step. The first blend material is combined with screened lubricant (e.g., magnesium stearate and/or sodium fumarate) and admixed (blended) in a second pre-blending step to form the pre-blend. The pre-blend is granulated by roller compaction, milled and screen to form a granulate. The granulate is combined with screened extragranular filler and admixed (blended) in a first final blending step. The first blend material is combined with screened extragranular lubricant and admixed (blended) in a second final blending step to form a tableting blend. The tableting blend is compressed using any suitable tableting apparatus known in the art to form tablet cores. Solid film coating material is combined with an aqueous carrier and suspended. The table cores are coated with the film coating suspension to form the finished tablets.

Pre-blending

Pre-blending is designed to provide substantial homogeneity of the intragranular components prior to roller compaction. Pre-blending equipment and related process parameters the provide for essentially homogeneous blends are known to those skilled in the art and are not believed to be narrowly critical. Suitable blenders are known in the art and any apparatus typically employed in the pharmaceutical industry for uniformly admixing two or more components including V-shaped blenders, double-cone blenders, bin (container) blenders, and rotary drum blenders. The combination blender volume, blender fill, rotation speed and rotation time may be suitably determined by those skilled in the art, based on routine experimentation, to achieve an essentially homogeneous admixture of components. Blender volume is suitably 50 L, 100 L, 200 L, 250 L or greater. Selection of blender fill allows for convection and three-dimensional material movement and is suitably about 25%, about 30%, about 35%, about 40%, about 50%, about 60% or about 70%, and ranges thereof, such as from about 30% to about 60%, from about 45% to about 65%, from 32% to 53% or from 32% to 40%. Blend time is suitably, 5 min, 10 min, 15 min, 20 min, 30 min, 40 min, 50 min, 60 min, or more. Rotation rate is suitably, for instance, 2 rpm, 3 rpm, 4 rpm, 5 rpm, 6 rpm, 7 rpm, 8 rpm, 9 rpm or 10 rpm.

Filler, lubricant and disintegrants are typically delumped by screening prior to blending. Screening methods are known to this skilled in the art.

In an example of one particular pre-blend aspect of the disclosure, filler (e.g. lactose monohydrate and MCC) and disintegrant (e.g., croscarmellose sodium) are delumped by screening and are combined with the active drug (e.g., cobimetinib hemifumarate) in a blender, and the blender contents are blended for a blend time (e.g., 30 minutes) at a fixed rotation rate (e.g., 6 rpm). Lubricant (e.g., magnesium stearate) is delumped by screening and is added to a blender containing admixed filler, disintegrant and active drug. The blender contents are blended for a blend time (e.g., 8 minutes) at a fixed rotation rate (e.g., 6 rpm) to form the pre-blend.

In another example of one pre-blend aspect of the disclosure, the active drug (e.g., cobimetinib hemifumarate) is blended with a delumped disintegrant (e.g., croscarmellose sodium) for a blend time (e.g., 5 minutes at 6 rpm). Optional delumped binder (e.g., copovidone) is added to the blender and the contents are blended for a blend time (e.g., 15 minutes at 6 rpm). Delumped filler (e.g., lactose and MCC) is added to the blender and the contents are blended for a blend time (e.g., 15 minutes at 6 rpm). Delumped lubricant (e.g., magnesium stearate) is added to the blender and the contents are blended for a blend time (e.g., 2 minutes).

Granulation and Sizing

Granulation and sizing may be achieved using any suitable means known to those skilled in the art. In some particular aspects of the disclosure, granulation and sizing comprises dry granulation, milling and screening (sieving). In some other aspects of the disclosure, dry granulation is roller compaction.

Granulation and sizing improves flow and compression characteristics of the admixture of active drug and excipients. Roller compaction is a process wherein pre-blend powder particles are made to adhere together resulting in larger, granular multi-particle entities. Roller compaction generally comprises three unit operations including a feeding system, a compaction unit and a milling/sieving unit. In the compaction unit, the pre-blend is compacted between counter-rotating rolls by application of a roller compaction force (expressed in kN/cm) to form a formed mass of compacted material, such as a ribbon or a sheet. The distance between the rolls is defined as the gap width. The formed ribbon of compacted material is processed in a size reduction unit by milling to form granules that are screened to produce a plurality of granules having a desired particle size distribution.

Roller compaction and milling equipment is available commercially from a number of manufacturers including Gerteis, Fitzpatrick®, Freund-Vector. Such equipment generally provides for control of roller compaction force, gap width, roller speed and feed rate. The roller surfaces may be smooth, knurled, or one roller surface may be smooth and the other roller surface may be knurled. In any of the various aspects, the pre-blend is charged to a roller compactor feed hopper. Roller compaction is performed at a specified force and gap size, and the process is preferably run under gap control. The formed ribbons are milled through a screen to produce granules. In some aspects of the disclosure, the screen is integral to the mill.

Without being bound to any particular theory, it is believed that the properties of the ribbon and granules formed therefrom are affected by the combination of roller compaction and milling variables including roller compaction force, gap width, material mass throughput, the screen size, and the uniformity and composition of the pre-blend. It is further believed that the properties of the formed ribbon (as influenced by gap size, roller compaction force, etc.) affects tablet appearance due, among other effects, to punch filming/sticking. It is further believed that the roller compaction variables may affect granule particle size distribution, granule density (thus, compressibility), and granule flow. Roller compaction gap size is believed to have an impact on cohesiveness of the final blend particles, with smaller gap size leading to granules with a greater tendency to stick. It is further believed that a smaller gap size may result in filming on the punches during tablet compression and the production of tablets with appearance defects. Roller compaction force is believed to influence the densification of the pre-blend during granulation, to affect granule properties, and to affect in vitro dissolution of the resulting tablets. Experimental evidence indicates that decreasing roller compaction force produces final blend with better flowability, leading to reduced variability in main compression force and tablet weight, and increased control of uniformity of dosage units. Milling screen size impacts granule particle size distribution which may impact flowability and may impact the uniformity of the dosage units. For instance, under some conditions, poor flow could cause segregation in the tableting feed hopper and/or during feeding. Further, poor flow could also impact tableting die filling with concomitant tablet weight variation. It is believed that tablet disintegration is not generally affected by granule particle size in tablet embodiments wherein disintegrant is present both intra and extragranularly.

The combination of roller compaction force and gap size is believed to influence ribbon/granule density, especially as the gap is reduced, and to affect in vitro dissolution of the resulting tables. Gap size, along with roller compaction force, has also been observed to affect the sticking tendency of the final blend during tablet compression and the production of tablets with appearance defects. Increasing the gap size and decreasing roller compaction force produces final blend with a lower sticking tendency and leads to improved tablet appearance.

In any of the various aspects of the disclosure, the gap size is about 2 mm, about 3 mm, about 4 mm or about 5 mm, and ranges thereof, such as from about 2 mm to about 5 mm, from about 2 mm to about 4 mm, from about 3 mm to about 5 mm or from about 4 mm to about 5 mm. Based on experimental evidence to date, such gap sizes are generally sufficient to reduce sticking. The roller compaction force is about 1 kN/cm, about 2 kN/cm, about 3 kN/cm, about 4 kN/cm, about 5 kN/cm, about 6 kN/cm, about 7 kN/cm or about 8 kN/cm, and ranges thereof, such as from about 1 kN/cm to about 8 kN/cm, from about 2 kN/cm to about 5 kN/cm or from about 2 kN/cm to about 4 kN/cm. Based on experimental evidence, it has been discovered that the roller compaction parameters of the present disclosure allow for sufficient compensation of the active drug properties at pre-blend loadings of as well as control of the granule properties to achieve an optimum tablet compression process.

In any of the various aspects of the disclosure, the milling screen size is 0.5 mm, 0.75 mm, 1.0 mm, 1.25 mm, 1.5 mm, 1.75 mm, 2.0 mm, 2.25 mm or 2.5 mm, and ranges thereof, such as from about 0.5 mm to about 2.5 mm, from about 0.5 mm to about 2.0 mm, from about 0.5 mm to about 1.5 mm, from about 0.5 mm to about 1.25 mm, from about 0.75 mm to about 2.5 mm, from about 0.75 mm to about 2.0 mm, from about 0.75 mm to about 1.5 mm, from about 0.75 mm to about 1.25 mm. In some particular aspects of the disclosure, a 1.0 mm milling screen is used.

Ribbon at-gap density (defined as ribbon throughput per operational time divided by the calculated volume per time) is the result of the combination of roller compaction parameters and is believed to be correlated with granule properties and with processability during tablet compression. Ribbon at-gap density is suitably about 0.85 g/mL, about 0.9 g/mL, about 0.95 g/mL, about 1.0 g/mL, about 1.05 g/mL, about 1.1 g/mL about 1.15 g/mL, about 1.2 g/mL, about 1.25 g/mL or about 1.3 g/mL and ranges thereof, such as from about 0.85 g/mL to about 1.3 g/mL, from about 0.9 g/mL to about 1.25 g/mL, from about 0.95 g/mL to about 1.2 g/mL. In some aspects of the disclosure low ribbon at-gap density of from about 0.85 g/mL to about 95 g/mL or from about 0.9 g/mL to about 0.95 g/mL is selected and controlled for. In some other aspects of the disclosure center point ribbon at-gap density of from about 0.95 g/mL to from about 1.1 g/mL, from about 0.95 g/mL to about 1.05 g/mL, from about 1 g/mL to about 1.10 g/mL or from about 1 g/mL to about 1.05 g/mL is selected and controlled for. In yet other aspects of the disclosure high ribbon at-gap density of from about 1.1 g/mL to about 1.3 g/mL, from about 1.1 g/mL to about 1.25 g/mL, from about 1.1 g/mL to about 1.2 g/mL, from about 1.1 g/mL to about 1.15 g/mL, from about 1.15 g/mL to about 1.3 g/mL, from about 1.15 g/mL to about 1.25 g/mL, or from about 1.15 g/mL to about 1.2 g/mL is selected and controlled for.

In some particular aspects of the present disclosure, for an active drug with a PSD D [v, 0.5] of from about 25 μm to about 40 μm or from 27 μm to 37 μm, a roller compaction force of 2 kN/cm and gap size at 5 mm may be suitably used for granulation. In some other particular aspects of the present disclosure, for an active drug with a PSD D [v, 0.5] of from about 40 μm to about 65 μm or from 38 μm to 65 μm, a roller compaction force of 2 to 4 kN/cm and gap size of 4 to 5 mm may be suitably used for granulation.

Final Blending

In the final blending step, granules formed by roller compaction and milling are charged to a blender and any extragranular portion of the disintegrant (e.g., croscarmellose sodium) and the lubricant (e.g., magnesium stearate) is added to the blender to form an admixture. The final blending step provide for an essentially homogeneous distribution of any external disintegrant and lubricant and provides for acceptable processability during tablet compression. Suitable blenders and related process variables are described above.

In some aspects, the disintegrant is delumped prior to addition to the blender and the disintegrant is blended with the granules under a first set of blending conditions (e.g., for 10 minutes at 6 rpm). In a second final blending step, the lubricant is delumped and added to the blender and blended under a second set of blending conditions (e.g., for about 8 minutes at 6 rpm).

In any of the various aspects of the disclosure, the final blend bulk density is about 0.4 g/mL, about 0.45 g/mL, about 0.5 g/mL, about 0.55 g/mL, about 0.6 g/mL, about 0.65 g/mL, about 0.7 g/mL or about 0.75 g/mL, and ranges thereof, such as from about 0.4 g/mL to about 0.75 g/mL, from about 0.45 g/mL to about 0.7 g/mL, or from about 0.51 g/mL to 0.63 g/mL. The final blend is preferably easy or free flowing and has a flow function coefficient of at least 4.

Tableting

In the tableting step, a tableting die mold is filled with final blend material and the mixture is compressed to form a tablet core that is ejected. Suitable tablet presses are known in the art and are available commercially from, for instance, Riva-Piccola, Fette, Bosch Packaging Technology, GEA and Natoli Engineering Company. Generally, each tablet is made by pressing the granules inside a die, made up of hardened steel. The die is a disc shape with a hole cut through its center. The powder is compressed in the center of the die by two hardened steel punches that fit into the top and bottom of the die thereby forming the tablet. Tablet compression may be done in two stages with the first, pre-compression, stage involving tamping down the powder and compacting the blend slightly prior to application of the main compression force for tablet formation. The tablet is ejected from the die after compression.

Main compression force affects tablet characteristics such as hardness and appearance. Main compression force further has an impact on sticking of the final blend to tablet tooling during compression, with increased force leading to reduced sticking and, hence, fewer tablets with appearance defects. Further, the compressibility of the final blend can impact the quality (such as the presence or lack of defects) of the resultant tablet core. Compression processing parameters, such as compression force and run time, can also have an impact. Final blend material attributes and compression process parameters may also have an impact on tablet weight variability and content. Further, variations in input final blend material attributes and compression processing parameters may have an impact on tablet weight variability, which is directly related to uniformity of dosage units. Moreover, quality attributes of the tablet core, such as hardness, friability, and porosity, are related to dissolution and impacted by compression processing parameters.

In some aspects of the disclosure, the compression force is about 5 kN, about 6 kN, about 7 kN, about 8 kN, about 9 kN, about 10 kN, about 11 kN, about 12 kN, about 13 kN, about 14 kN, about 15 kN, about 16 kN, about 17 kN, about 18 kN, about 19 kN or about 20 kN, and ranges thereof, such as from about 5 kN to about 20 kN, from about 14 kN to about 19 kN, from about 14 kN to about 18 kN, or from about 8 kN to about 13 kN. In some aspects of the disclosure, tablets comprising about 60 mg of the active drug may be formed at a compression force of from about 14 kN to about 18 kN. In other aspects of the disclosure, tablets comprising about 20 mg of the active drug may be formed at a compression force of from about 8 kN to about 13 kN.

Film Coating

The tablet cores are film-coated to ensure that tablets are essentially tasteless and odorless, and are easy to swallow. Film coating also prevents dust formation during packaging and ensures robustness during transportation. Film coating may suitably be done by methods known in the art such as by pan coating. Suitable coating equipment includes, without limitation, a Glatt GC1000S.

In some aspects of the disclosure, tablet cores are charged to a coating pan and warmed to a target temperature. The coating suspension is prepared to a target solids content. Once the tablets are within the target temperature range, drum rotation and spraying are runs at target rates designed to achieve predetermined weight gain of about 3 wt. %, about 4 wt. % or about 5 wt. %. Outlet air temperature is maintained in a range to ensure that the target product temperature is obtained throughout coating. Once spraying is complete, the coated tablets are dried and cooled down before discharging the film-coated tablets. A solid content of a coating suspension is suitably about 12 wt. %, about 13 wt. %, about 14 wt. %, about 15 wt. %, about 16 wt. %, about 17 wt. %, about 18 wt. %, about 19 wt. % or about 20 wt. %, and ranges thereof, such as from about 12 wt. % to about 20 wt. %, or from about 14 wt. % to about 20 wt. %. The coating spray rate per kg of tablet cores is suitably about 0.8, about 1, about 1.5, about 1.9 about 2, about 2.1, about 2.2, about 2.3, about 2.4 or about 2.5, and ranges thereof, such as from about 0.8 to about 2.5, or from about 1 to about 2.1. The coating temperature is suitably about 35° C., about 39° C., about 40° C., about 45° C., about 47° C., about 48° C., about 49° C., about 50° C. or about 55° C., and ranges thereof, such as from about 35° C. to about 50° C., or from about 39° C. to about 47° C. The pan rotational speed is suitably about 2 rpm, about 4 rpm, about 5 rpm, about 8 rpm, about 10 rpm, about 12 rpm, about 15 rpm or about 20 rpm, and ranges thereof, such as from about 2 to about 20 rpm, from about 4 to about 15 rpm, or from about 8 to about 12 rpm. The inlet air volume varies with the batch size and is suitably about 300 m$^3$/h, about 450 m$^3$/h, about 600 m$^3$/h, about 750 m³/h, about 1000 m³/h, about 1250 m³/h, or about 1500 m³/h, and ranges thereof, such as from about 300 to about 1500 m³/h, from about 450 to about 1200 m³/h, or from about 1000 to about 1250 m³/h.

Tablet Cores and Coated Tablets

In some aspects of the present disclosure the tablet core comprises the components and concentration ranges in wt. % as indicated in Table B.

TABLE B

| Component | 1st Range | 2nd Range | 3rd Range |
|---|---|---|---|
| Active drug | 5-35% | 10-30% | 15-25% |
| Filler | 60-78% | 65-78% | 70-78% |
| Disintegrant | 1-7% | 2-6% | 3-5% |
| Lubricant | 0.5-5% | 1-4% | 1-3% |
| Binder (Optional) | 0-10% | 0-8% | 0-6% |

In some aspects of the present disclosure, the tablet core comprises the components and concentration ranges in wt. % as indicated in Table C on the basis of a tablet containing 20 mg of the active drug. In some other aspects, the tablet contains 40 mg or 60 mg of the active drug. For tablets comprising other than 20 mg of the active drug, e.g., 40 mg or 60 mg, the ratios of the various components disclosed below for the 20 mg tablets is maintained.

TABLE C

| Component | 1st Range | 2nd Range | 3rd Range |
|---|---|---|---|
| Active drug | 17.5-18.5% | 17.5-18.5% | 17.5-18.5% |
| Filler | 60-78% | 65-78% | 70-78% |
| Disintegrant | 1-7% | 2-6% | 3-5% |
| Lubricant | 0.5-5% | 1-4% | 1-3% |
| Binder (Optional) | 0-10% | 0-8% | 0-6% |

In some aspects of the present disclosure, the tablet core comprises the components and concentration ranges in wt. % as indicated in Table D on the basis of a tablet containing 20 mg of the active drug.

TABLE D

| Component | 1st Range | 2nd Range | 3rd Range |
|---|---|---|---|
| Cobimetinib Hemifumarate Polymorph Form A | 17.5-18.5% | 17.5-18.5% | 17.5-18.5% |
| MCC | 36-47% | 39-47% | 42-47% |
| Lactose monohydrate | 24-31% | 26-31% | 38-47% |
| Croscarmellose sodium | 1-7% | 2-6% | 3-5% |
| Magnesium stearate | 0.5-5% | 1-4% | 1-3% |
| Binder (Optional) | 0-10% | 0-8% | 0-6% |

In some particular aspects of the present disclosure, the tablet cores comprise the components and concentrations in wt. % as indicated in Table E on the basis of a tablet containing 20 mg of the active drug.

TABLE E

| Component | 1st Tablet | 2nd Tablet |
|---|---|---|
| Cobimetinib Hemifumarate polymorph Form A | 18.5% | 18.5% |
| MCC | 24.67% | 45.6% |
| Lactose monohydrate | 48.33% | 30.4% |

TABLE E-continued

| Component | 1st Tablet | 2nd Tablet |
|---|---|---|
| Croscarmellose sodium | | |
| Intragranular | 1% | 2% |
| Extragranular | 1% | 2% |
| Magnesium stearate | | |
| Intragranular | 0.375% | 0.25% |
| Extragranular | 1.125% | 1.25% |
| Copovidone | 5% | 0% |

In some particular aspects of the present disclosure, coated tablet cores comprise the components and concentrations in wt. % as indicated in Table F on the basis of a tablet containing 20 mg of the active drug. The components and concentrations in wt. % of a film coating composition is indicated in Table G.

TABLE F

| Component | 1st Tablet | 2nd Tablet |
|---|---|---|
| Cobimetinib Hemifumarate polymorph Form A | 17.96% | 17.79% |
| MCC | 23.95% | 43.85% |
| Lactose monohydrate | 46.92% | 29.23% |
| Croscarmellose sodium | | |
| Intragranular | 0.97% | 1.92% |
| Extragranular | 0.97% | 1.92% |
| Magnesium stearate | | |
| Intragranular | 0.36% | 0.24% |
| Extragranular | 1.09% | 1.21% |
| Copovidone | 4.85% | 0% |
| Film Coating | 2.91% | 3.85% |

TABLE G

| Component | Concentration |
|---|---|
| Polyvinyl Alcohol | 40% |
| Titanium Dioxide | 25% |
| Macrogol/PEG 3350 | 20.2% |
| Talc | 14.8% |

Tablets and table cores of the present disclosure are characterized by the specifications listed in Table H.

TABLE H

| Specification | Limit |
|---|---|
| Content Uniformity (% RSD, n = 30) | <4% |
| Assay (% of label claim) | 95.0-105.0% |
| Dissolution at 15 and 30 minutes (% dissolved, min., n = 6) | ≥80% |
| Disintegration Time (sec, average, n = 6) | ≤300 |
| Average Hardness (N, n = 6) | 45-85 |
| Abrasion (%) | <1.0% |
| Weight Variation (% RSD, n = 90) | ≤3% |
| Weight Range (mg, n = 90) | ≤18 |
| Main Compression Force Variation (% RSD) | ≤13% |

Cancer Medicaments

The combination of cobimetinib and vemurafenib has been shown to reduce the risk of BRAF$^{V600}$ mutation-positive advance melanoma worsening, or death, by half with a median progression-free survival for the drug combination of 9.9 months as compared to 6.2 months for vemurafenib alone (Larkin, et al., *Combined Vemurafenib* and *Cobimetinib in BRAF-Mutated Melanoma*, New England Journal of Medicine, 371:1867-1876, 2014).

In some aspects, the present disclosure relates to the use of the MEK inhibitor tablets of the present invention in combination with a BRAF inhibitor for the treatment of cancer. More particularly, in some aspects, the present disclosure relates to the use of the MEK inhibitor tablets of the present disclosure in combination with a BRAF inhibitor for the therapeutic treatment of patients having unresectable or metastatic melanoma with $BRAF^{V600}$ mutation. Such combination therapies are disclosed in International Publication Number WO 2014/027056 A1 (incorporated herein by reference).

Vemurafenib (propane-1-sulfonic acid {3-[5-(4-chlorophenyl)-1H-pyrrolo[2,3-b]pyridine-3-carbonyl]-2,4-difluoro-phenyl}-amide) is FDA-approved for treatment of patients with unresectable or metastatic melanoma that is $BRAF^{V600E}$ mutation-positive using the Cobas® 4800 $BRAF^{V600}$ Mutation Test (see ZELBORAF® [vemurafenib] package insert). Vemurafenib was associated with a 63% reduction in the risk of death and a 74% decrease in the risk of disease progression or death, when compared with dacarbazine (Chapman et al., NEJM (2011) 364 (26):2507-16). Moreover, vemurafenib treatment led to response rates consistently greater than 50% and median OS of 14 to 16 months (Flaherty et al., NEJM (2010) 363:809-819; Chapman et al., id.; Sosman et al., NEJM (2012) 366(8):707). In one aspect, ZELBORAF® is administered at a dose of 960 mg twice daily, on days 1-28 of a 28 day cycle.

Cobimetinib is expected to be marketed as COTELLIC™ and, in one aspect, each COTELLIC™ dose consists of three 20 mg (60 mg) tablets taken together orally once daily for 21 consecutive days (day 1 to 21-treatment period); followed by a 7 day break in COTELLIC™ treatment (days 22-28-treatment break)."

In one combination treatment aspect, a method of treating (e.g., therapeutically treating) a patient having $BRAF^{V600}$ mutation-positive unresectable or metastatic melanoma is provided, the method comprises administering to the patient (i) tableted cobimetinib (e.g., COTELLIC™) at a dose of 60 mg (e.g., three 20 mg tablets), on days 1-21 of a 28 day cycle; and (ii) tableted vemurafenib (e.g., ZELBORAF®) at a dose of 960 mg (e.g., four 240 mg tablets) twice daily, on days 1-28 of the 28 day cycle. In some such aspects, the cobimetinib and vemurafenib tablets are administered sequentially. In some such aspects, the cobimetinib and vemurafenib tablets are administered concurrently. In some other such aspects, the BRAFV600 mutation-positive unresectable or metastatic melanoma has not been previously treated.

Kits are provided in some further aspects of the disclosure, the kits comprising (i) cobimetinib tablets (e.g., COTELLIC™); and (ii) vemurafenib (e.g., ZELBORAF®); for use in the treatment of unresectable or metastatic melanoma, wherein cobimetinib is administered at a dose of 60 mg (e.g., three 20 mg tablets), on days 1-21 of a 28 day cycle, and wherein vemurafenib (e.g., ZELBORAF®) at a dose of 960 mg (e.g., four 240 mg tablets), twice daily each day of the 28 day cycle. The kit may further comprise a package insert indicating that the combination of pharmaceutical compositions are for treating (e.g., therapeutically treating) a patient with $BRAF^{V600}$ mutation-positive unresectable or metastatic melanoma, in combination with vemurafenib, wherein cobimetinib is administered at a dose of 60 mg, on days 1-21 of a 28 day cycle and vemurafenib is administered at a dose of 960 mg (e.g., four 240 mg tablets) twice daily, on days 1-28 of the 28 day cycle.

Treatment may, for example, increase survival of the patient, decrease the patient's risk of cancer recurrence, increase duration of response to treatment and/or increase the patient's likelihood of survival. In some aspects, the unresectable or metastatic melanoma has not been previously treated (i.e., previously treated for unresectable or metastatic melanoma). In other aspects, the patient's unresectable or metastatic melanoma has been previously treated (in some embodiments, without prior treatment to BRAF inhibitor). In some other aspects, the first composition comprising cobimetinib and the second composition comprising vemurafenib are provided as a single dosing form.

EXAMPLES

Various testing and analytical methods are described herein.

Determination of identity, assay, and degradation products is performed by the same reversed-phase liquid chromatography (reversed-phase high-performance liquid chromatography, reversed-phase rapid resolution liquid chromatography, ultra-high-performance liquid chromatography) method. One such method uses a stainless steel 100×4.6 mm column having a C18, 3.5 µm stationary phase (e.g., Waters SunFire). The following working conditions may be used: A column temperature of 40° C.; Ultraviolet detection at 240 mm; Mobile phase A of 0.02% trifluoroacetic acid in water; and Mobile phase B of 0.02% trifluoroacetic acid in water/acetonitrile 10/90 (v/v).

Determination of uniformity of dosage units ("UDU") was performed according to the general chapter, "Uniformity of Dosage Units," USP <905>, harmonized with Ph. Eur. 2.9.40 and JP 6.02. The content uniformity test is performed by reversed-phase high-performance liquid chromatography (RP-HPLC)/reversed-phase rapid resolution liquid chromatography (RP-RRLC) with a C18, a stainless steel 150×4.6 mm column having a C18, 3.5 µm stationary phase (e.g., Waters Symmetry). The following working conditions may be used: A column temperature of 40° C.; Ultraviolet detection at 240 mm; Mobile phase A of 0.03% formic acid in water; and Mobile phase B of 0.01% formic acid in acetonitrile.

The dissolution test is performed using the general chapter, "Dissolution," described in USP <711>, harmonized with Ph. Eur. "Dissolution," Ph. Eur. 2.9.3 "Dissolution Test for Solid Dosage Forms," and JP 6.10 "Dissolution Test." The following methodology may be used: 50 rpm; 50 mmol/L acetate buffer, pH 4.5; 37° C.; and UV detection at 278 nm.

Hausner ratio and Carr index are known in the art indices that are correlated to flowability. The Hausner ratio is calculated by the formula $H=\rho_T/\rho_B$ where $\rho_B$ is the freely settled bulk density of the powder and $\rho_T$ is the trapped bulk density of the powder. A Hausner ratio of greater than 1.25 is generally considered to be an indication of poor flowability. The Hausner ratio (H) is related to the Carr index (C) by the formula $H=100/(100-C)$.

Tablet hardness testing is known in the art and is a measure of the breaking point and structural integrity of a tablet. In one compression test method, an aligned tablet is compressed in a testing apparatus with increasing force continually applied until the tablet fractures thereby indicating the hardness.

Friability testing is known in the art and is a measure of the likelihood of a tablet breaking into smaller pieces during transit. The methodology involves repeatedly dropping a sample of tablets over a fixed time, using a rotating wheel with a baffle, and afterwards checking whether any tablets are broken, and what percentage of the initial mass of the tablets has been chipped off.

Example 1

Example 1 evaluated the quantitative effects of binder level, intra and extragranular disintegrant level, and lubricant level in tablets with the experimental design indicated in Table 1.1 Below.

TABLE 1.1

| | | Levels | | |
|---|---|---|---|---|
| | Factors: Formulation Variables | −1 | 0[a] | +1 |
| A | Binder (%) | 0 | 3 | 5 |
| B | Disintegrant (%) | 3 | 4 | 5 |
| C | Lubricant (Intragranular %:extragranular %) | 0.25:1.25 | 0.5:1.25 | 0.5:1.5 |
| D | Lactose:MCC ratio | 0:1 | 1:1 | 1:0 |
| Q | Particle Size of the active drug Batch 1: D [v, 0.5] = 4.7 μm Batch 2: D [v, 0.5] = 1.5 μm Batch 3: D [v, 0.5] = 10.7 μm | | | |
| | Result Key | | | |
| $Y_1$ | Fines (granules) (%) | | | |
| $Y_2$ | Coarse (granules) (%) | | | |
| $Y_3$ | Hausner Ratio (granules) | | | |
| $Y_4$ | Hardness (60 mg tablets) (Kp) | | | |
| $Y_5$ | Normalized Hardness (60 mg tablets) | | | |
| $Y_6$ | Friability (60 mg tablets) (%) | | | |
| $Y_7$ | Disintegration Time (60 mg tablets) (s) | | | |
| $Y_8$ | Dissolution at 5 min (60 mg tablets) (%) | | | |
| $Y_{10}$ | Hardness (20 mg tablets) (Kp) | | | |
| $Y_{11}$ | Normalized Hardness (20 mg tablets) | | | |
| $Y_{12}$ | Friability (20 mg tablets) (%) | | | |
| $Y_{13}$ | Disintegration Time (20 mg tablets) (s) | | | |
| $Y_{14}$ | Dissolution at 5 min (20 mg tablets) (%) | | | |

[a]Center-point conditions were repeated with Active Drug with D [v, 0.5] = 10.7 μm The protocol for Example 1 is detailed in Table 1.2 below.

TABLE 1.2

| Process Step | Equipment |
|---|---|
| Pre-blending | V Blender (8 quart, rotational speed 25 rpm) Blend Active Drug and croscarmellose sodium for 5 min. Add copovidone; blend for 15 min. Add lactose and MCC; blend for 15 min. Add intragranular magnesium stearate; blend for 2 min. |
| Roller Compaction including Milling | Roller width 25 mm, roller diameter 120 mm Roller surface: top = smooth, bottom = knurled Roller pressure: 25 Bar Roller gap: 2 mm Roller speed: 3 rpm Feed screw: 22-40 rpm Milling: Vector-Lab Micro granulator, 1.0 mm screen |
| Final Blending | V Blender (4 quart, rotational speed 25 rpm) Blend granules and extragranular croscarmellose sodium for 10 min. Add extragranular magnesium stearate; blend for 2 min. |
| Tablet Compression | 10-station Piccola rotary tablet press speed: 20 rpm 60 mg tablets: Tooling: oval shape Number of punch stations used: 2 Compression force: 14-18 kN 20 mg tablets: Tooling: round shape (6.5 mm diameter) Number of punch stations used: 5 Compression force: 8-13 kN |

Granules produced in the final blending step were assessed for Results Y1 to Y3 (flow properties and PSD [Fines %, Coarse %]) and also submitted for an assessment of mechanical properties using a compaction simulator. They were further processed into tablets using a Piccola tablet rotary press and the resultant tablets assessed for results Y4 to Y15. Results for the granules are presented in Table 1.3 and for the tablets in Tables 1.4A and 1.4B. As used herein throughout, "Pattern" refers to the variable values specified in an experimental design table by references such as a, −1, 0, +1 and A. For instance, Table 1.1 denotes values in terms of −1, 0 and +1 for the concentration of binder (denoted as "A" in %), for the concentration of disintegrant (denoted as "B" in %), for the ratio of intragranular lubricant to extragranular lubricant (denoted as "C") and for the ratio of lactose filler to MCC filler (denoted as "D"). As one example, −1 for binder (A) refers to 0 wt. %, +1 for disintegrant (B) refers to 5 wt. %, +1 for the intragranular:extragranular lubricant ratio (C) refers to 0.5: 1.5, and −1 for the lactose:MCC ratio refers to 0:1. Turning to Table 1.3, the Pattern −++− refers to the values for A B C D of 0 wt. %, 5 wt. %, 0.5:1.5 and 0:1, respectively. Other patterns may be similarly construed.

TABLE 1.3

| | Factors | | | | | | Results | | |
|---|---|---|---|---|---|---|---|---|---|
| Pattern | Q | A | B | C | D | RSF | $Y_1$ | $Y_2$ | $Y_3$ |
| 0 | 4.8 | 3 | 4 | 0.5:1.25 | 1:1 | 0.735 | 36.5 | 37.4 | 1.44 |
| − + + − | 4.8 | 0 | 5 | 0.5:1.5 | 0:1 | 0.700 | 36.4 | 37.0 | 1.44 |
| + − − + | 4.8 | 5 | 3 | 0.25:1.25 | 1:0 | 0.790 | 26.8 | 44.6 | 1.40 |
| − + − + | 1.5 | 0 | 5 | 0.25:1.25 | 1:0 | 0.780 | 21.9 | 48.6 | 1.37 |
| − − − − | 4.8 | 0 | 3 | 0.25:1.25 | 0:1 | 0.700 | 33.3 | 45.5 | 1.40 |
| + + − − | 1.5 | 5 | 5 | 0.25:1.25 | 0:1 | 0.790 | 32.3 | 43.6 | 1.41 |
| + + + + | 4.8 | 5 | 5 | 0.5:1.5 | 1:0 | 0.750 | 24.8 | 45.3 | 1.43 |
| − − + + | 1.5 | 0 | 3 | 0.5:1.5 | 1:0 | 0.820 | 25.2 | 41.0 | 1.43 |
| + − + − | 1.5 | 5 | 3 | 0.5:1.5 | 0:1 | 0.720 | 38.6 | 35.7 | 1.39 |
| 0 | 4.8 | 3 | 4 | 0.5:1.25 | 1:1 | 0.760 | 34.9 | 35.7 | 1.42 |
| 0 | 1.5 | 3 | 4 | 0.5:1.25 | 1:1 | 0.760 | 33.0 | 40.0 | 1.41 |
| A | 1 | 3 | 4 | 0.5:1.25 | 1:1 | 0.710 | 28.4 | 44.7 | — |

TABLE 1.4A

| | Results (60 mg tablets) | | | | | |
|---|---|---|---|---|---|---|
| Pattern | Compress Force (kN) | $Y_4$ | $Y_5$[a] | $Y_6$ | $Y_7$ | $Y_8$ |
| 0 | 17.5 | 14.0 | 0.80 | 0.09 | 355 | 48 |
| − + + − | 18.0 | 13.6 | 0.76 | 0.10 | 32 | 76 |
| + − − + | 16.5 | 10.4 | 0.63 | 0.18 | 345 | 41 |
| − + − + | 16.5 | 9.9 | 0.60 | 5.20[b] | 116 | 70 |
| − − − − | 14.0 | 13.8 | 0.99 | 0.09 | 20 | 70 |
| + + − − | 15.1 | 14.0 | 0.93 | 0.04 | 380 | 59 |
| + + + + | 17.0 | 10.7 | 0.63 | 0.14 | 305 | 41 |
| − − + + | 18.0 | 10.9 | 0.61 | 0.15 | 286 | 66 |
| + − + − | 13.5 | 13.8 | 1.02 | 0.08 | 304 | 57 |
| 0 | 16.0 | 13.4 | 0.84 | 0.08 | 266 | 55 |
| 0 | 16.3 | 14.1 | 0.87 | 0.07 | 281 | 57 |
| 0 | 17.6 | 15.4 | 0.88 | 0.04 | 343 | 57 |

TABLE 1.4B

| | | Results (20 mg tablets) | | | | |
|---|---|---|---|---|---|---|
| Pattern | Compress Force (kN) | $Y_{10}$ | $Y_{11}{}^a$ | $Y_{12}$ | $Y_{13}$ | $Y_{14}$ |
| 0       | 10.6 | 6.9 | 0.65 | 0.00%  | 265 | 57 |
| − + + − | 11.2 | 6.7 | 0.60 | 0.01%  | 41  | 74 |
| + − − + | 13.0 | 7.3 | 0.56 | 0.08%  | 365 | 49 |
| − + − + | 10.8 | 5.4 | 0.50 | 0.04%  | 204 | 81 |
| − − − − | 8.6  | 7.4 | 0.86 | −0.07% | 34  | 72 |
| + + − − | 9.0  | 6.9 | 0.77 | −0.08% | 211 | 70 |
| + + + + | 9.9  | 5.6 | 0.57 | −0.04% | 270 | 49 |
| − − + + | 12.1 | 5.6 | 0.46 | 0.05%  | 257 | 70 |
| + − + − | 7.9  | 6.6 | 0.84 | −0.02% | 350 | 46 |
| 0       | 12.1 | 7   | 0.58 | 0.02%  | 315 | 59 |
| 0       | 10.2 | 6.9 | 0.68 | 0.00%  | 291 | 71 |
| 0       | 20 mg tablets not manufactured | | | | | |

Statistical evaluation revealed the same effects of factors for the 20 mg and 60 mg dose strengths. The granules used were common to the manufacture of both strengths and therefore conclusions are valid for both 20 mg and 60 mg tablets.

Some sticking to process equipment was observed for compositions comprising the finest Active Drug batch evaluated (D [v, 0.5] 1.5 μm).

Dissolution was studied in pH 4.5 acetate buffer at 37° C. using USP Apparatus II, rotating paddles at 75 rpm. Dry binder was shown to have an impact on '5 minutes' dissolution. Percentage of cobimetinib dissolved after 5 minutes decreased with increasing binder. These effects were less distinctive in the dissolution test after 15 minutes with dissolution values greater than 80%.

Hardness values are presented in Table 1.3 as normalized values, calculated as the ratio of tablet hardness (crushing strength) to the force used to compress the formulation. The lactose to MCC ratio was determined to effect tablet hardness, with increasing lactose leading to decreasing hardness at a given compression force. Dry binder did not significantly impact tablet hardness.

The lactose to MCC ratio affects the % fines. Increasing levels of lactose monohydrate resulted in a decrease in the % fines of the granules.

The bulk and tapped density of each granulation were determined and used to calculate Hausner ratio as an indication of flowability. Lubricant concentration was the only significant factor influencing Hausner ratio. Increasing levels of magnesium stearate from 1.5% (total) to 2.0% (total) increased the Hausner ratio slightly, indicating poorer flow. At 1.5% magnesium stearate (0.25% intragranular and 1.25% extragranular) tablets with acceptable physical properties and satisfactory tablet ejection forces were produced.

All tablets, independent of the compression force with which they were compressed, showed acceptable friability (<0.2% weight loss for a tablet hardness in the range 5.4-7.4 kP for 20 mg tablets and 9.9-15.4 kP for 60 mg tablets). The one exception was a single 60 mg batch where a single tablet split at the end of the friability test, leading to a friability result (outlier) of 5.2%. The same formulation/granules compressed to 20 mg tablets with a similar normalized hardness showed very good friability with 0.04% weight loss. The formulation variables in the ranges studied did not show any statistically significant impact on tablet friability.

Granules produced in Example 1 were subjected to compression at various pressures, on a Presster compaction simulator, for dwell times of 15 ms and 75 ms using round, flat-faced tooling to make cylindrical tablets with 9.5 mm diameter. Immediately after ejection, the tablets were broken diametrically using a texture analyzer (speed: 0.01 mm/s) and the results used to plot compaction pressure against tensile strength (MPa) to determine tabletability and compactability. Granules exhibited variable compression properties due to formulation variations and excipient properties. Overall compressibility and compactability were insensitive to tableting speed. Granules from all formulations tested in the study produced tablets with acceptable tensile strength (>2 MPa) when compressed at typical operating pressures for the production of solid oral-dosage forms.

Example 2

Example 2 evaluated the ratio of filler components (lactose monohydrate to MCC), roller compaction gap size, and roller compaction force as indicated in Table 2.1 below. The lactose monohydrate to MCC ratios of 40:60, 50:50, 60:40, 36:64, and 64:36 by mass were evaluated. For the purposes of the present disclosure, these ratios referred to as a single numerical value representing the % lactose monohydrate in the lactose monohydrate-MCC mix, hence, 36%, 40%, 50%, 60%, and 64% lactose monohydrate.

The intra and extragranular disintegrant and lubricant levels were fixed and a single batch of active drug having a particle size distribution of D [v, 0.5] 4.7 μm and D [v, 0.9] 20.2 μm) was used. The experiment was repeated a second active drug batch having a particle size distribution of D [v, 0.5] 10.7 μm and D [v, 0.9] 25.2 μm.

Furthermore, ribbon solid fraction (RSF) (relative density) was used as a process parameter to reduce the number of parameters associated with roller compaction (which is a result of the combination of variable, such as, for example, roller compaction gap size and force).

TABLE 2.1

| | | Levels | | | | |
|---|---|---|---|---|---|---|
| | Factors | a | −1 | 0 | +1 | A |
| A | Lactose (%) | 36 | 40 | 50 | 60 | 64 |
| B | Target Ribbon Solid Fraction | 0.56 | 0.59 | 0.67 | 0.75 | 0.78 |
| — | Roller Compaction Gap Size (mm) | 4 | 4 | 3 | 2 | 2 |
| — | Roller Compaction Force (kN/cm) | 2.5 | 3 | 5 | 7.5 | 10 |
| $Y_1$ | Fines (granules) (%) | | | | | |
| $Y_2$ | Coarse (granules) (%) | | | | | |
| $Y_3$ | Carr's Index (granules) | | | | | |
| $Y_4$ | Hausner Ratio (granules) | | | | | |
| $Y_5$ | Hardness (Kp) | | | | | |
| $Y_6$ | Normalized Hardness | | | | | |
| $Y_7$ | Friability (%) | | | | | |
| $Y_8$ | Disintegration Time (s) | | | | | |
| $Y_9$ | Dissolution at 5 min (%) | | | | | |
| $Y_{10}$ | Dissolution at 15 min (%) | | | | | |

As with Example 1, resultant granules were assessed for Reponses $Y_1$ to $Y_4$. They were also further processed into tablets using a Piccola rotary tablet press and the resultant tablets assessed for results $Y_5$ to $Y_{10}$.

The protocol for Experiment 2 is detailed in Table 2.2 below.

TABLE 2.2

| Process Step | Equipment |
|---|---|
| Pre-Roller Compaction Blending and Lubrication | V Blender (8 quart, rotational speed 25 rpm) Blend MCC, Active Drug, lactose, and intragranular croscarmellose sodium for 30 min. Add intragranular magnesium stearate and blend for 2 min. |
| Roller Compaction including Milling | Roller surface: left = smooth; right = knurled Roller speed: 3 rpm Tamp/feed ratio: 180%, 250% Milling: Star mill, 1 mm screen Operation: gap control |
| Final Blending and Lubrication | V Blender (8 quart, rotational speed 25 rpm) Blend granules and extragranular croscarmellose sodium for 10 min Add extragranular magnesium stearate and blend for 2 min |
| Tablet Compression | 10-station Piccola rotary tablet press Tooling: oval shape Number of punch stations used: 2 Press speed: 20 rpm Compression force: 12 kN to 16.5 kN |

Granules produced in the final blending step were assessed for Results Y1 to Y4. They were further processed into tablets using a Piccola tablet rotary press and the resultant tablets assessed for Results Y5 to Y10. Results for the granules are presented in Table 2.3 and for the tablets in Tables 2.4.

TABLE 2.3

| Pattern | A | B | Active D [v, 0.5] | $Y_1$ | $Y_2$ | $Y_3$ | $Y_4$ |
|---|---|---|---|---|---|---|---|
| 0 | 50 | 0.67 | 4.7 | 32.4 | 41.9 | 26.3 | 1.36 |
| – – | 40 | 0.59 | 4.7 | 39.5 | 19.7 | 27.0 | 1.37 |
| 0 | 50 | 0.67 | 4.7 | 33.3 | 42.7 | 27.6 | 1.38 |
| A0 | 64 | 0.67 | 4.7 | 32.7 | 38.1 | 24.2 | 1.32 |
| a0 | 36 | 0.67 | 4.7 | 33.3 | 41.3 | 27.0 | 1.37 |
| + + | 60 | 0.75 | 4.7 | 25.0 | 52.9 | 26.7 | 1.36 |
| + – | 60 | 0.59 | 4.7 | 39.5 | 22.7 | 28.6 | 1.40 |
| – + | 40 | 0.75 | 4.7 | 29.6 | 48.1 | 25.3 | 1.34 |
| 0a | 50 | 0.56 | 4.7 | 46.1 | 14.7 | 28.4 | 1.40 |
| 0A | 50 | 0.78 | 4.7 | 19.6 | 53.6 | 25.5 | 1.34 |
| 0 | 50 | 0.67 | 10.7 | 23.6 | 41.5 | 27.1 | 1.37 |
| 0a | 50 | 0.56 | 10.7 | 32.1 | 20.2 | 32.6 | 1.48 |
| 0A | 50 | 0.78 | 10.7 | 17.0 | 59.0 | 23.7 | 1.31 |
| A0 | 64 | 0.67 | 10.7 | 32.4 | 31.1 | 28.1 | 1.39 |
| a0 | 36 | 0.67 | 10.7 | 25.0 | 43.2 | 30.0 | 1.43 |

TABLE 2.4

| Pattern | Compression Force (kN) | $Y_5$ | $Y_6{}^a$ | $Y_7$ | $Y_8$ | $Y_9$ | $Y_{10}$ |
|---|---|---|---|---|---|---|---|
| 0 | 14.0 | 13.8 | 0.99 | 0.03 | 150 | 72 | 96 |
| – – | 12.0 | 14.5 | 1.21 | 0.04 | 83 | 72 | 95 |
| 0 | 13.5 | 14.1 | 1.04 | 0.04 | 149 | 71 | 96 |
| A0 | 16.0 | 13.3 | 0.83 | 0.07 | 192 | 65 | 93 |
| a0 | 13.5 | 14.0 | 1.04 | 0.04 | 124 | 73 | 95 |
| + + | 14.5 | 14.1 | 0.97 | 0.01 | 210 | 64 | 95 |
| + – | 13.5 | 14.5 | 1.07 | 0.06 | 135 | 66 | 95 |
| – + | 14.5 | 13.6 | 0.94 | 0.03 | 164 | 69 | 94 |
| 0a | 13.5 | 15.2 | 1.13 | 0.00 | 145 | 70 | 95 |
| 0A | 16.5 | 12.9 | 0.78 | 0.09 | 173 | 65 | 93 |
| 0 | 13.0 | 13.0 | 1.00 | 0.04 | 135 | 73 | 95 |
| 0a | 12.5 | 14.8 | 1.18 | 0.04 | 120 | 73 | 96 |
| 0A | 16.0 | 13.1 | 0.82 | 0.05 | 210 | 69 | 96 |
| A0 | 13.5 | 14.1 | 1.04 | 0.05 | 188 | 68 | 96 |
| a0 | 14.5 | 14.2 | 0.98 | 0.02 | 130 | 78 | 96 |

[a]Hardness (Norm) = normalized hardness = ratio of hardness to the compression force.

Both Carr's index and Hausner ratio show similar trends and increasing RSF leads to slightly better flow (lower Carr's index and Hausner ratio). The amount of lactose monohydrate in the formulation had no impact on flow.

Tablet hardness decreases with increasing RSF but is unaffected by the amount of lactose monohydrate in the formulation.

All factors studied had negligible impact on friability and tablets produced under all conditions studied had <0.10% weight loss.

Dissolution was studied in pH 4.5 acetate buffer at 37° C. using USP Apparatus II, rotating paddles at 75 rpm. These dissolution conditions were considered the optimum at this stage of development and for the examination of these formulations. Dissolution values (%) after 5 minutes were lower with increasing RSF and also lower with increasing lactose monohydrate level in the formulation. These values correlate well with tablet disintegration times, indicating that this slower dissolution after 5 minutes may be due to slower disintegration times for formulations containing higher lactose monohydrate content. These effects were not evident after 15 minutes, where dissolution for all batches was >85%.

Increasing RSF leads to less fines of the granules but also leads to tablets with a lower hardness (crushing strength) and lower % dissolution after 5 minutes.

Increasing lactose monohydrate present in the formulation has no significant impact on % fines or tablet hardness but leads to lower dissolution values after 5 minutes. These lower dissolution results are well correlated with, and— without being bound to any particular theory—believed to be most likely due to, slower disintegration times at higher lactose monohydrate contents.

An active drug with a smaller particle size leads to a slight increase in the amount of fines present in granules. This increase does not adversely impact flow, either apparent in Carr's index or Hausner ratio value or during tablet compression over the range studied.

Example 3

Prototype tablets were prepared in pilot scale testing at least on the basis of Examples 1 and 2 wherein the prototype formulations are disclosed in Tables 3.1 (prototype 1) and 3.2 (prototypes 2 and 3) below.

TABLE 3.1

| Material | Function | % w/w | mg/Tablet |
|---|---|---|---|
| Intragranular Excipients | | | |
| Lactose Monohydrate | Filler | 30.40 | 36.48 |
| Microcrystalline Cellulose[b] | Filler | 45.60 | 54.72[c] |
| Croscarmellose Sodium | Disintegrant | 2.00 | 2.40 |
| Magnesium Stearate | Lubricant | 0.25 | 0.30 |
| Extragranular Excipients | | | |
| Croscarmellose Sodium | Disintegrant | 2.00 | 2.40 |
| Magnesium Stearate | Lubricant | 1.25 | 1.50 |
| Tablet core weight | | 100.0 | 120.0 |
| Film Coating | | | |
| Opadry II White (85F18422) or Equivalent | Film coating | 4.00 | 4.80 |
| Total Film-Coated Tablet Weight: | | | 124.80 |

[a]The amount of cobimetinib hemifumarate is adjusted according to the potency of the active drug and corresponds to 20 mg of the free base.
[b]Microcrystalline cellulose PH-101, or equivalent.
[c]The amount of microcrystalline cellulose is adjusted based on the actual amount of the active drug.

TABLE 3.2

| Formulation | | Prototype Tablet 2 | Prototype Tablet 3 |
|---|---|---|---|
| Material | Function | % w/w | % w/w |
| Cobimetinib Hemifumarate | Active Drug | 18.50 | 18.50 |
| Lactose Monohydrate | Filler | 48.33 | 30.40 |
| Microcrystalline Cellulose[a] | Filler | 24.67 | 45.60 |
| Filler Ratio | | 2:1 | 1:1.5 |
| Copovidone | Binder | 5.00 | — |
| Croscarmellose Sodium | Disintegrant | | |
| Intragranular | | 1.00 | 2.00 |
| Extragranular | | 1.00 | 2.00 |
| Magnesium Stearate | Lubricant | | |
| Intragranular | | 0.375 | 0.25 |
| Extragranular | | 1.125 | 1.25 |
| Lubricant intra:extra ratio | | 1:3 | 1:5 |
| Opadry II White[b] | Film coating | 3.00 | 4.00 |

[a] Microcrystalline cellulose PH-101
[b] A commercially available equivalent film-coating mixture may be used (e.g., Opadry II White 85F18422).

Example 4

A relative bioavailability study compared the relative bioavailability of the active drug formulated as a power in a capsule ("PiC") (4×5 mg, equivalent to 18 mg cobimetinib as free base) with that of the prototype 2 film-coated tablet formulation (20 mg). Data are presented in Table 4.1 where "AUC" refers to the area under the plasma concentration vs. time curve; "CI" refers to the confidence interval; "CV" refers to the coefficient of variation; "PiC" refers to the active drug powder in capsule; Reference=PiC; and Test=prototype tablet. Statistical analysis was performed on the dose-normalized results. In the fasted state, the exposure of cobimetinib following administration of the prototype tablet was comparable to that following administration of the PiC formulation. Data indicate that formulation change (the presence of excipients in the tablet versus no excipients in the PiC formulation) had no effect on cobimetinib pharmacokinetics.

TABLE 4.1

| | Geometric Mean (CV %) | | |
|---|---|---|---|
| Formulation/ Dose | 4 × 5 mg PiC Fasted (n = 18) | 20 mg Prototype Tablet, Fasted (n = 19) | Test/Reference (90% CI) |
| $C_{max}$ (ng/mL) | 14.9 (45.9%) | 16.0 (33.5%) | 96.9 (84.2, 111) |
| $AUC_{0-\infty}$ (ng · h/mL) | 717 (45.1%) | 780 (34.7%) | 94.7 (83.9, 107) |

The relative bioavailability study was repeated comparing the relative bioavailability of the active drug formulated as a power in a capsule ("PiC") (4×5 mg, equivalent to 18 mg cobimetinib as free base) with that of the prototype 3 film-coated tablet formulation (20 mg). In the fasted state, exposures from the proposed commercial film-coated tablet formulation were comparable to that from the PiC. The 90% confidence intervals for the geometric mean ratio of AUC0-∞ were within 80% to 125% for the tablet versus PiC comparison, whereas the corresponding confidence intervals for Cmax suggest a slightly higher absorption rate for the commercial tablet than the PiC. Overall, these results indicate that cobimetinib oral bioavailability is unaltered by change in formulation form prototype 2 to prototype 3.

Example 5

In vitro performance of the prototype 3 cobimetinib 20 mg and 60 mg film-coated tablets was assessed according to the matrix of conditions shown in Table 5.1 using USP Apparatus II, rotating paddles, or USP Apparatus I, rotating baskets, and 900 mL of the stated medium at 37° C.

TABLE 5.1

| Agitation | 0.1M HCl (aq) | USP Acetate Buffer, pH | USP Phosphate Buffer, pH 6.8 | FaSSIF pH 6.5 |
|---|---|---|---|---|
| Paddles, 50 rpm | X | X | X | X |
| Paddles, 75 rpm | X | X | — | — |
| Baskets, 75 rpm | — | X | — | — |
| Baskets, 100 rpm | — | X | — | — |

Figure 4:
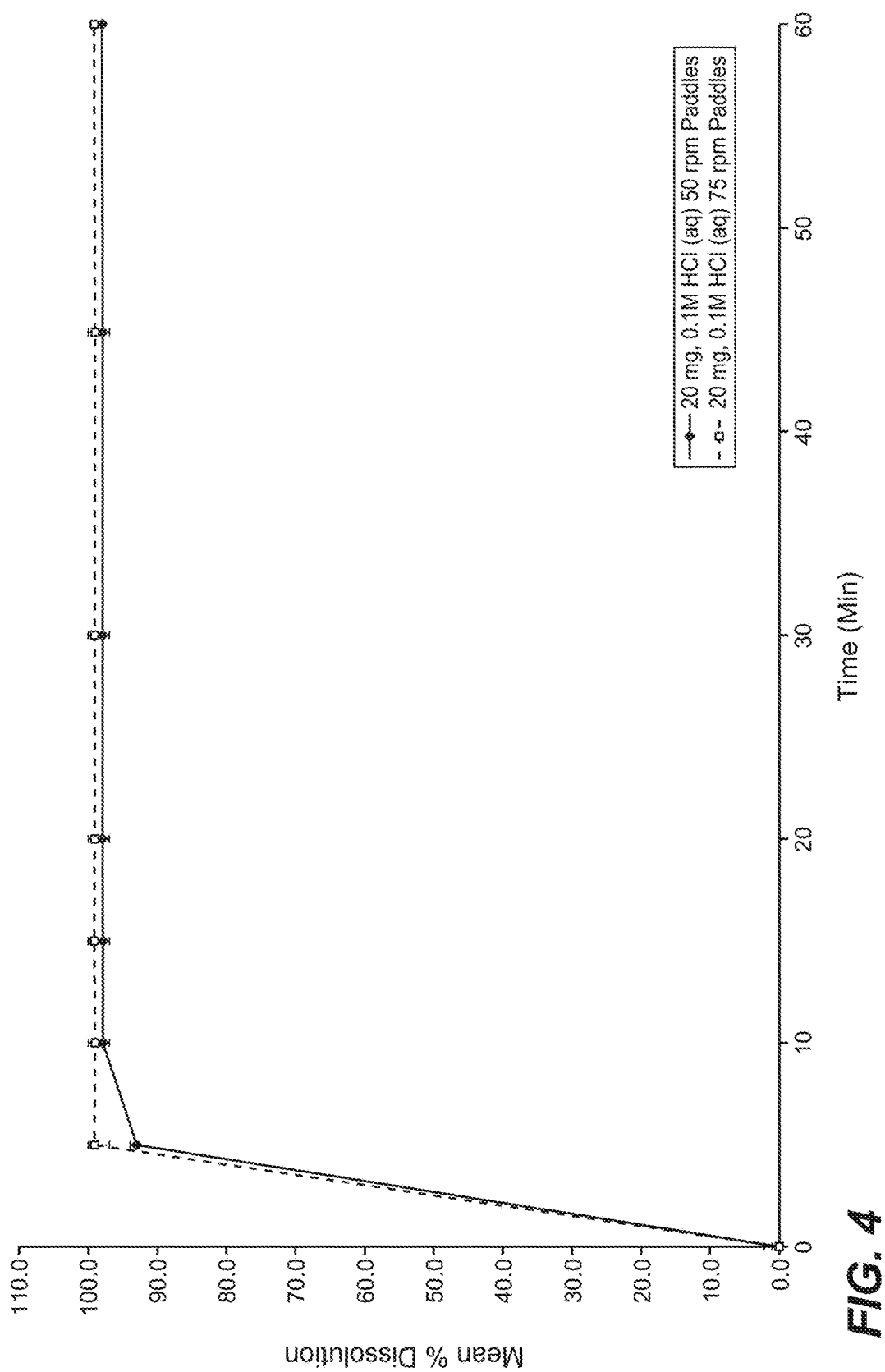
FIG. 4 is a graphical representation of the dissolution profile of cobimetinib hemifumarate film-coated tablets of the present disclosure in 0.1 M HCl.
Figure 5:
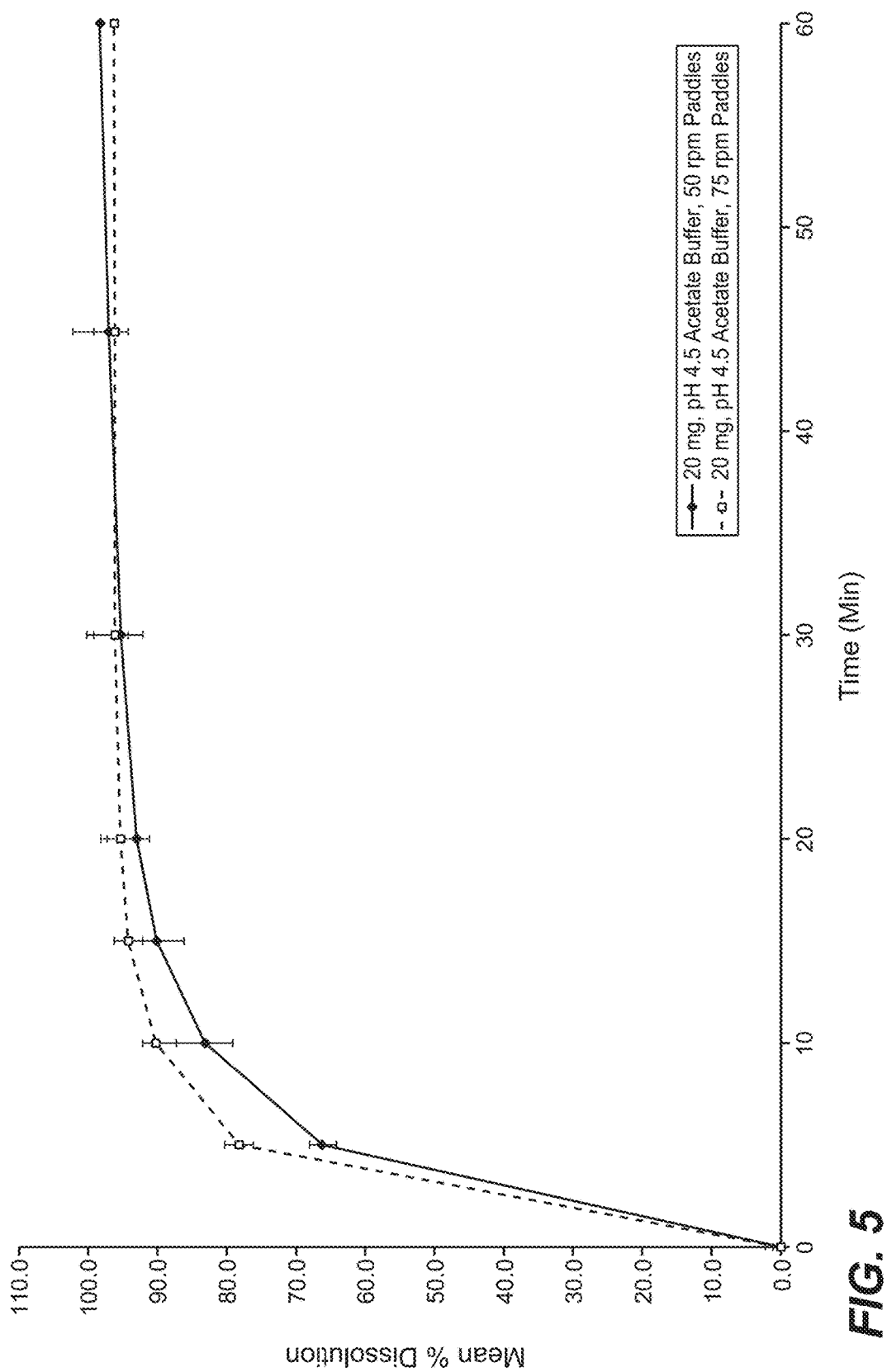
FIG. 5 is a graphical representation of the dissolution profile of cobimetinib hemifumarate film-coated tablets of the present disclosure in pH 4.5 Acetate buffer.
Figure 6:
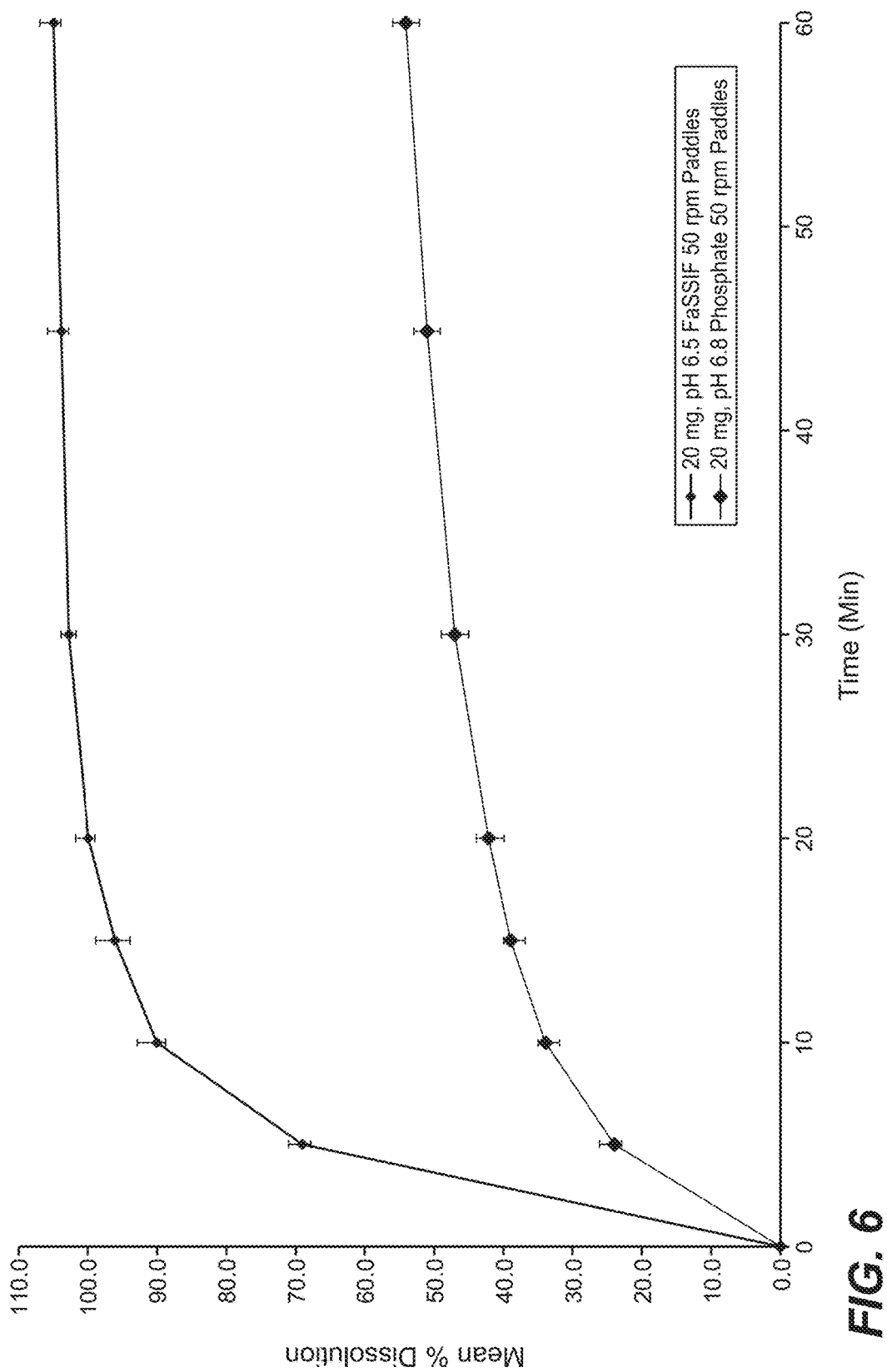
FIG. 6 is a graphical representation of the dissolution profile of cobimetinib hemifumarate film-coated tablets of the present disclosure in pH 6.8 Phosphate buffer.

Individual and mean dissolution results for both strengths were similar; therefore, data for the proposed commercial tablet strength of 20 mg only are presented in FIG. 4 (Plots of % dissolution against time for 0.1 M HCl (aq)), in FIG. 5 (for USP acetate buffer, pH 4.5), and in FIG. 6 (for phosphate buffer).

Dissolution in USP acetate buffer with agitation using rotating paddles (USP Apparatus II) shows an ascending profile between the start of the test and approximately 20 minutes, reaching a plateau by up to 30 minutes, using agitation speeds of both 50 rpm and 75 rpm. The dissolution curves show a similar profile, with only slightly more rapid dissolution at 75 rpm and low tablet-to-tablet variability under both conditions (standard deviation 3%-5% over the entire profile). Dissolution using the basket apparatus (USP Apparatus I) at 75 rpm is significantly slower than that using the paddles apparatus, achieving approximately 80% at 30 minutes and approximately 85% at 45 minutes without reaching a plateau. At 100 rpm rotation and basket apparatus, dissolution is slightly more rapid, reaching approximately 95% at 30 minutes but still increasing and with more variability than with the use of paddles. Infinity testing was applied from 45 min to 60 min.

Dissolution in conventional USP phosphate buffer, ($KH_2PO_4$, 50 mM) pH 6.8, for 20 mg tablets, was slow and incomplete after 60 minutes using an agitation speed of 50 rpm with paddles. The use of other media at similar pH, as FaSSIF pH 6.5 (Fasted State Simulated Intestinal Fluid) resulted in rapidly dissolving profile (>85% after 15 minutes). As FaSSIF is a complex medium and as exposure of cobimetinib is not expected to be limited by either solubility or permeability, no further Quality Control added value was expected at pH 6.8 in comparison to the consistence performance observed in acetate buffer at pH 4.5.

Dissolution in conventional USP phosphate buffer, ($KH_2PO_4$, 50 mM) pH 6.8, for 20 mg tablets, was slow and incomplete after 60 minutes using an agitation speed of 50 rpm with paddles. The use of other media at similar pH, as FaSSIF pH 6.5 (Fasted State Simulated Intestinal Fluid) resulted in rapidly dissolving profile (>85% after 15 minutes). As FaSSIF is a complex medium and as exposure of cobimetinib is not expected to be limited by either solubility or permeability.

Example 6

Dissolution plots were generated for three batches of cobimetinib 20 mg tablets manufactured according to the method of Example 3 prototype tablet 3 using active drug with a range of particle size particle size (D [v, 0.5]) between 11 μm and 47 μm were investigated. See Table 6.1 below.

TABLE 6.1

| Drug Product | Particle Size (μm) | |
|---|---|---|
| Tablet | D [v, 0.5] | D [v, 0.9] |
| Tablet 6A | 10.7 | 25.2 |
| Tablet 6B | 39 | 66 |
| Tablet 6C | 47 | 77 |

Figure 7:
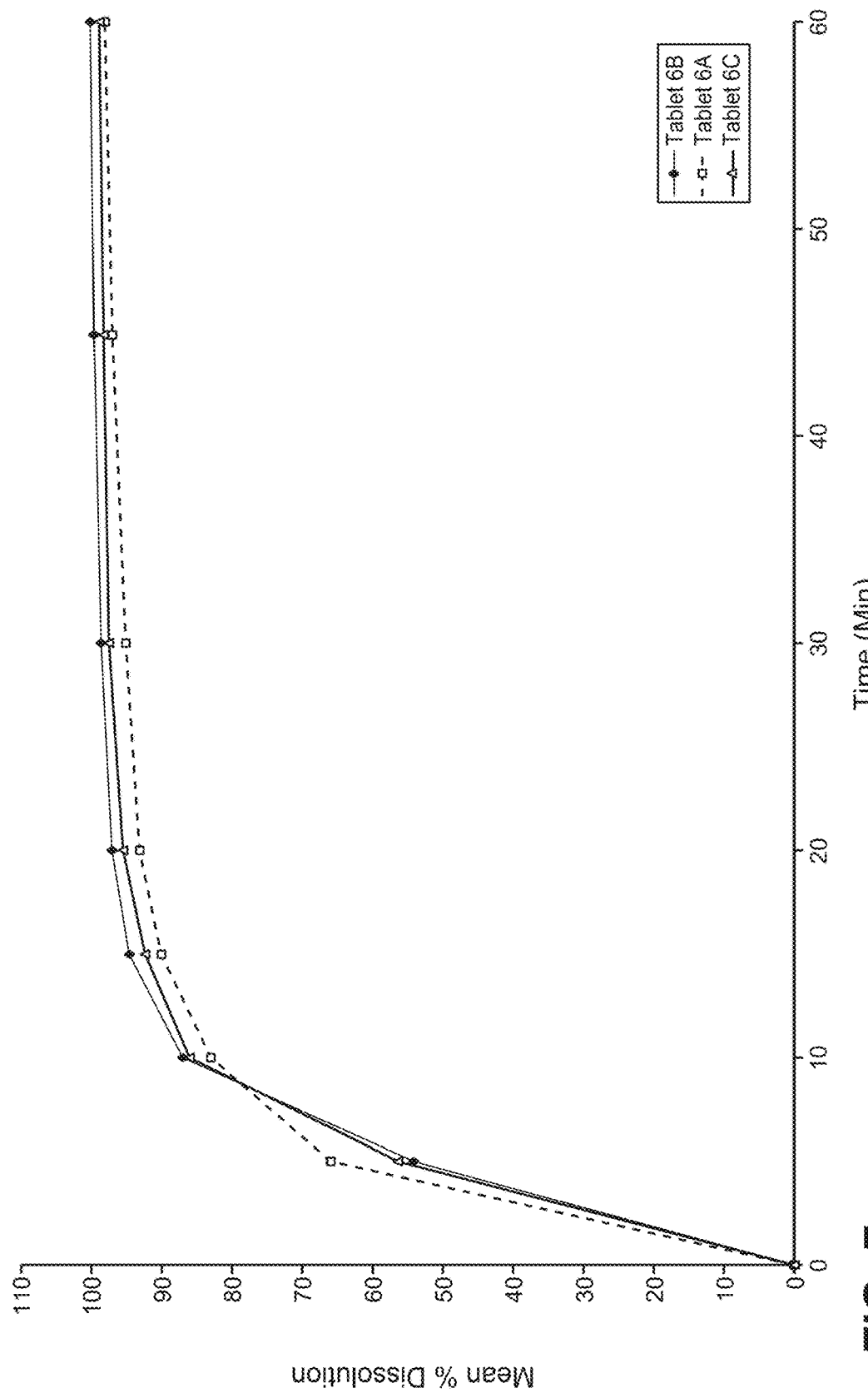
FIG. 7 is a graphical representation of the dissolution profile of three batches of cobimetinib hemifumarate film-coated tablets of the present disclosure in pH 4.5 Acetate buffer.

FIG. 7 depicts the dissolution plot for Batches 6A to 6C in 900 mL USP acetate buffer at pH 4.5 (50 rpm paddles) and at 37° C. and indicate that the tablets are insensitive to changes in active drug particle size distribution.

Example 7

Dissolution plots were generated for three batches of cobimetinib 60 mg tablets manufactured according to the method of Example 3 prototype tablet 3 manufactured with variations in the amount of disintegrant and lubricant and type and amount of filler were dissolved in 900 mL USP acetate buffer at pH 4.5 (50 rpm paddles) and at 37° C. The tablet compositions are disclosed in Table 7.1 below.

TABLE 7.1

| Tablet | Strength (mg) | Filler | Filler Level (%) | Disintegrant Level (%) | Lubricant Level (%) |
|---|---|---|---|---|---|
| Tablet 7A | 60 | MCC | 74.3 | 5.0 | 2.0 |
| Tablet 7B | 60 | MCC | 76.8 | 3.0 | 1.5 |
| Tablet 7C | 60 | Lactose | 75.0 | 5.0 | 1.5 |

Lubricant is magnesium stearate

Lubricant is Magnesium Stearate

Figure 8:
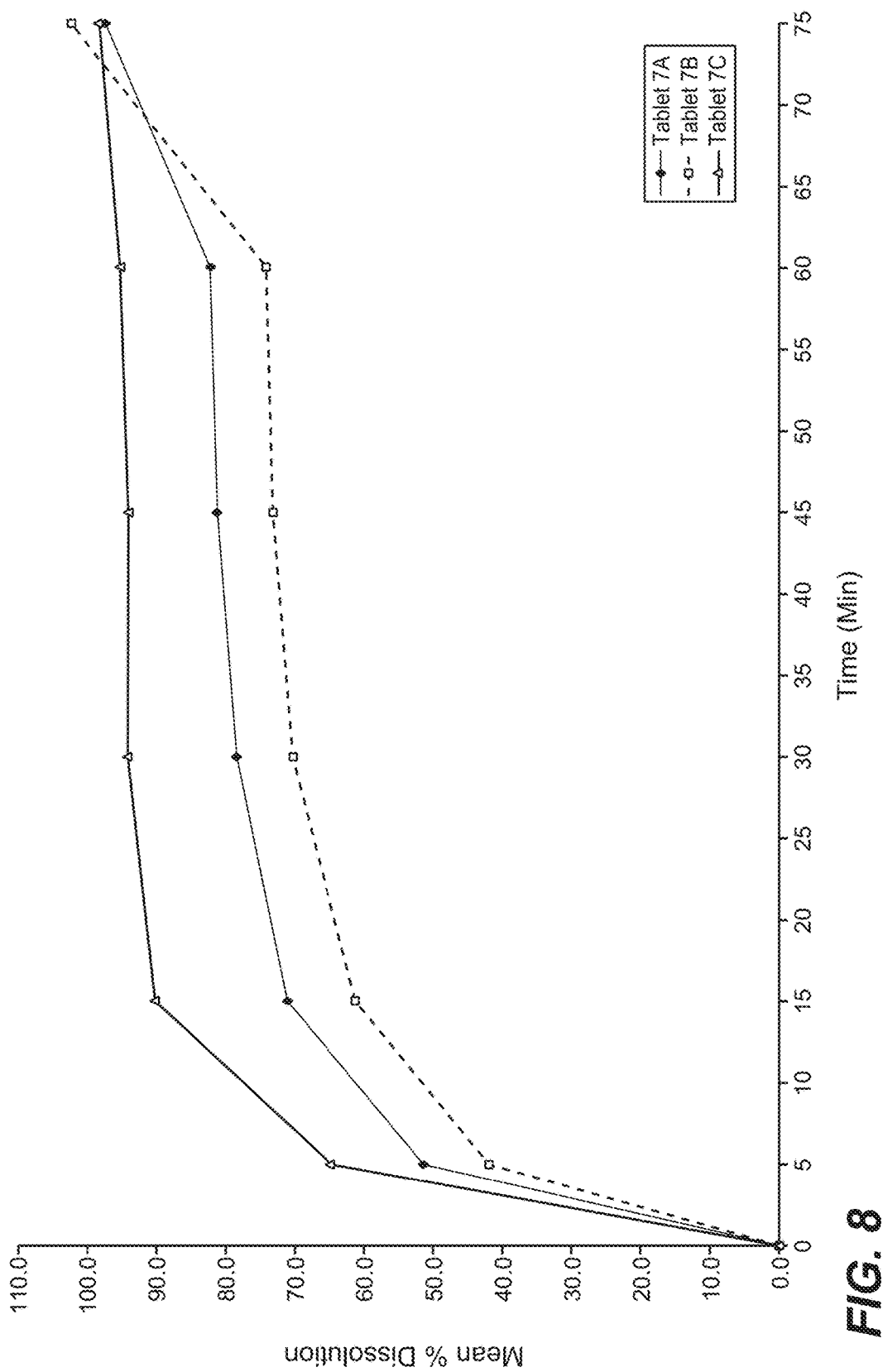
FIG. 8 is a graphical representation of the dissolution profile of three separate formulations of cobimetinib hemifumarate film-coated tablets of the present disclosure in pH 4.5 Acetate buffer.
Figure 9:
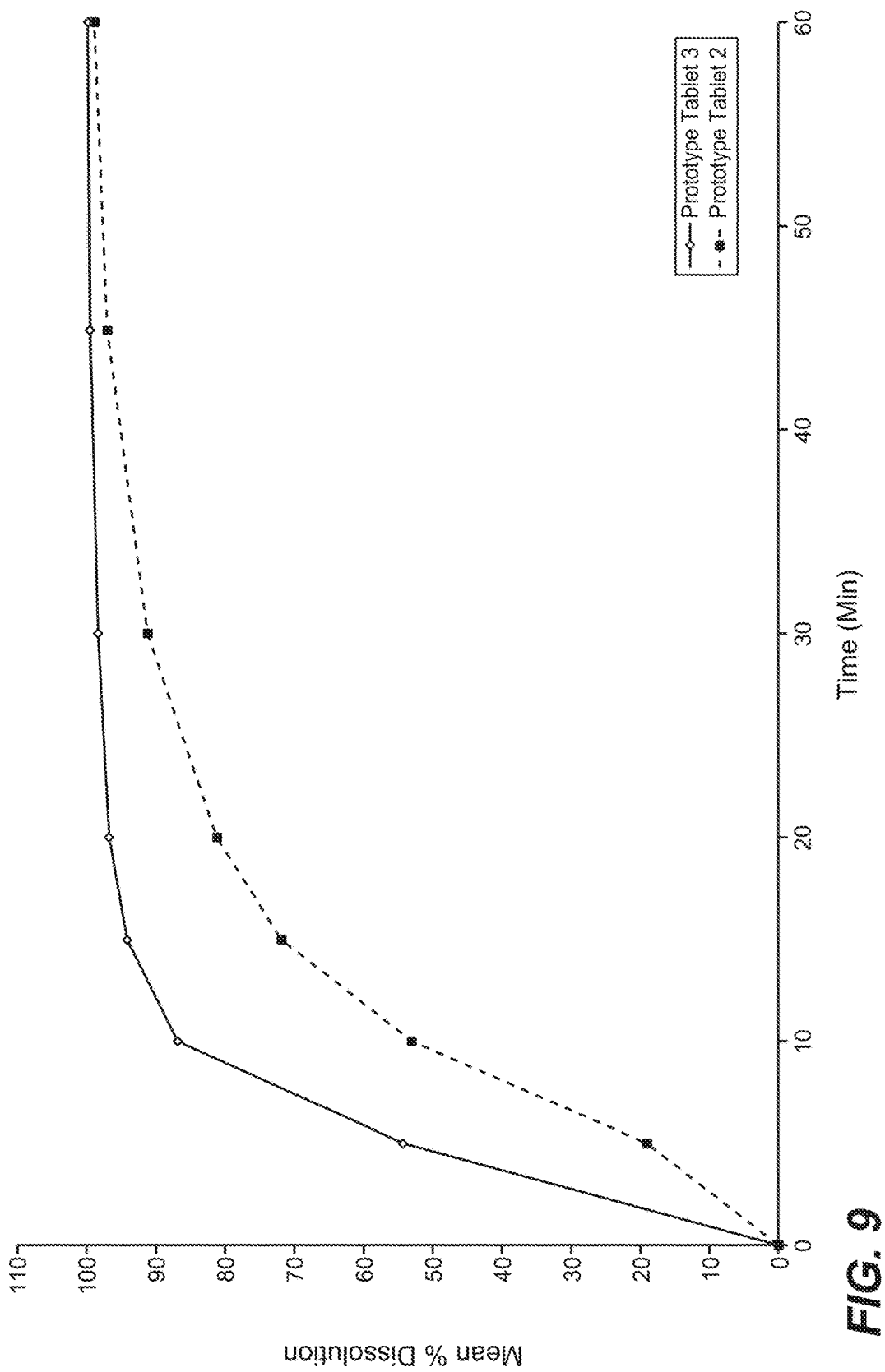
FIG. 9 is a graphical representation of the dissolution profile of two separate formulations of cobimetinib hemifumarate film-coated tablets of the present disclosure in pH 4.5 Acetate buffer.

The dissolution profile of Tablets 7A to 7C in USP acetate buffer at pH 4.5 (50 rpm paddles) is depicted in FIG. 8 and the dissolution profile of prototype tablets 2 and 3 of Example 3 in 900 mL USP acetate buffer at pH 4.5 (50 rpm paddles) and at 37° C. is depicted in FIG. 9.

Example 8

Figure 10:
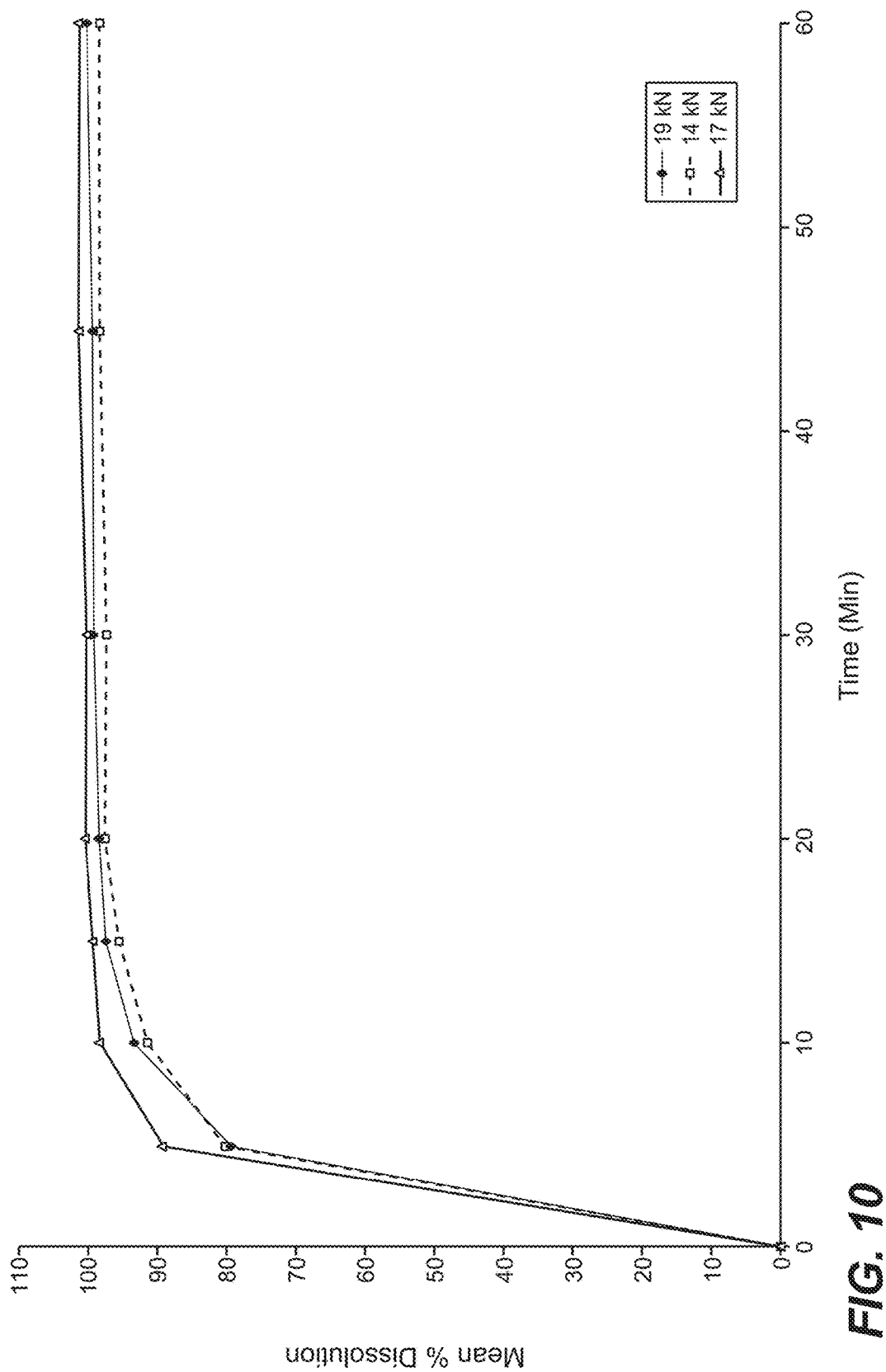
FIG. 10 is a graphical representation of the dissolution profile in pH 4.5 Acetate buffer of three formulations of cobimetinib hemifumarate film-coated tablets of the present disclosure tableted with different main compression force.

The impact of compression force on the dissolution of 20 mg tablets was studied over the range 7 to 19 kN during manufacturing process development experiments. Dissolution curves for core tablets manufactured with the proposed manufacturing process and compression at 7 kN, 14 kN and 19 kN are reported in FIG. 10. The data indicate that a slight trend is present in the early part of the dissolution profile (between approximately 0 and 15 minutes) for tablets manufactured with different compression forces (for gross changes). These differences are not apparent after 15-30 minutes.

Example 9

Tablets corresponding to prototype tablet 3 were formed from cobimetinib hemifumarate of varying particle according to the process of the present disclosure depicted in FIG. 11 and comprising (1) forming a pre-blend comprising lactose monohydrate, croscarmellose sodium, microcrystalline cellulose, cobimetinib hemifumarate and intragranular magnesium stearate, (2) roller compaction and milling to form granules, (3) blending the granules with extragranular croscarmellose sodium and extragranular magnesium stearate, (4) tableting and (5) film coating with Opadry II. A first group of tablets (designated Tablet 9A) were formed from cobimetinib hemifumarate having a particle size D[v. 0.5] of 29 μm and with a roller compaction force of 2.0 kN/cm, a gap size of 4.0 mm and a tableting compression force of 19 kN. A second group of tablets (designated Tablet 9B) were formed from cobimetinib hemifumarate having a particle size D[v. 0.5] of 38 μm and with a roller compaction force of 3.5 kN/cm, a gap size of 3.0 mm and a tableting compression force of 19 kN. A third group of tablets (designated Table 9C) were formed from cobimetinib hemifumarate having a particle size D[v. 0.5] of 47 μm and with a roller compaction force of 2.0 kN/cm, a gap size of 4.0 mm and a tableting compression force of 19 kN. For the tablets of each groups of tablets, tablet weight was measured and active drug content was determined by high pressure liquid chromatography.

Figure 12A:
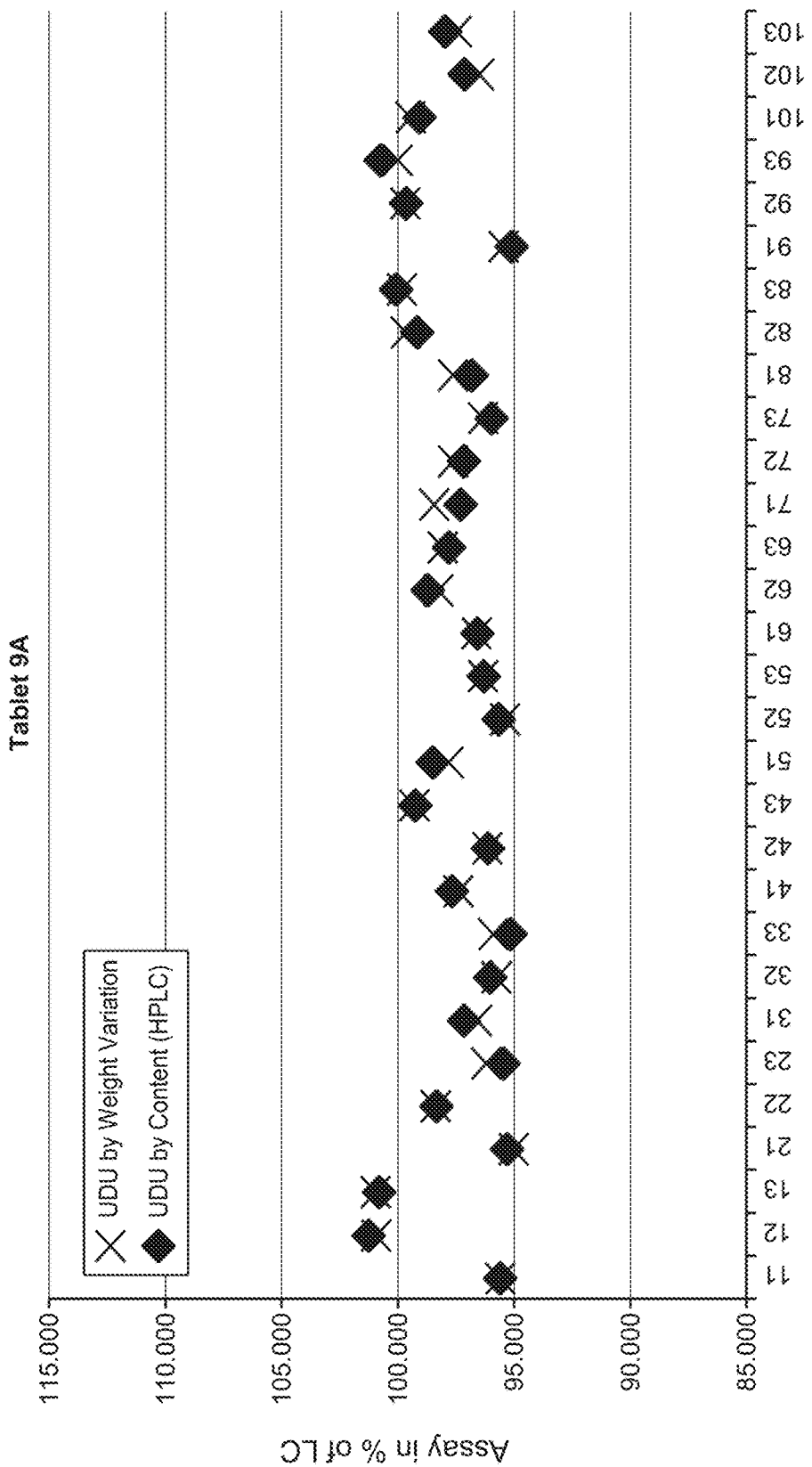
FIG. 12A is a plot of the comparison of tablet weight variation with content uniformity for tablets manufactured using an active drug with a particle size D [v, 0.5] of 29 μm.
Figure 12B:
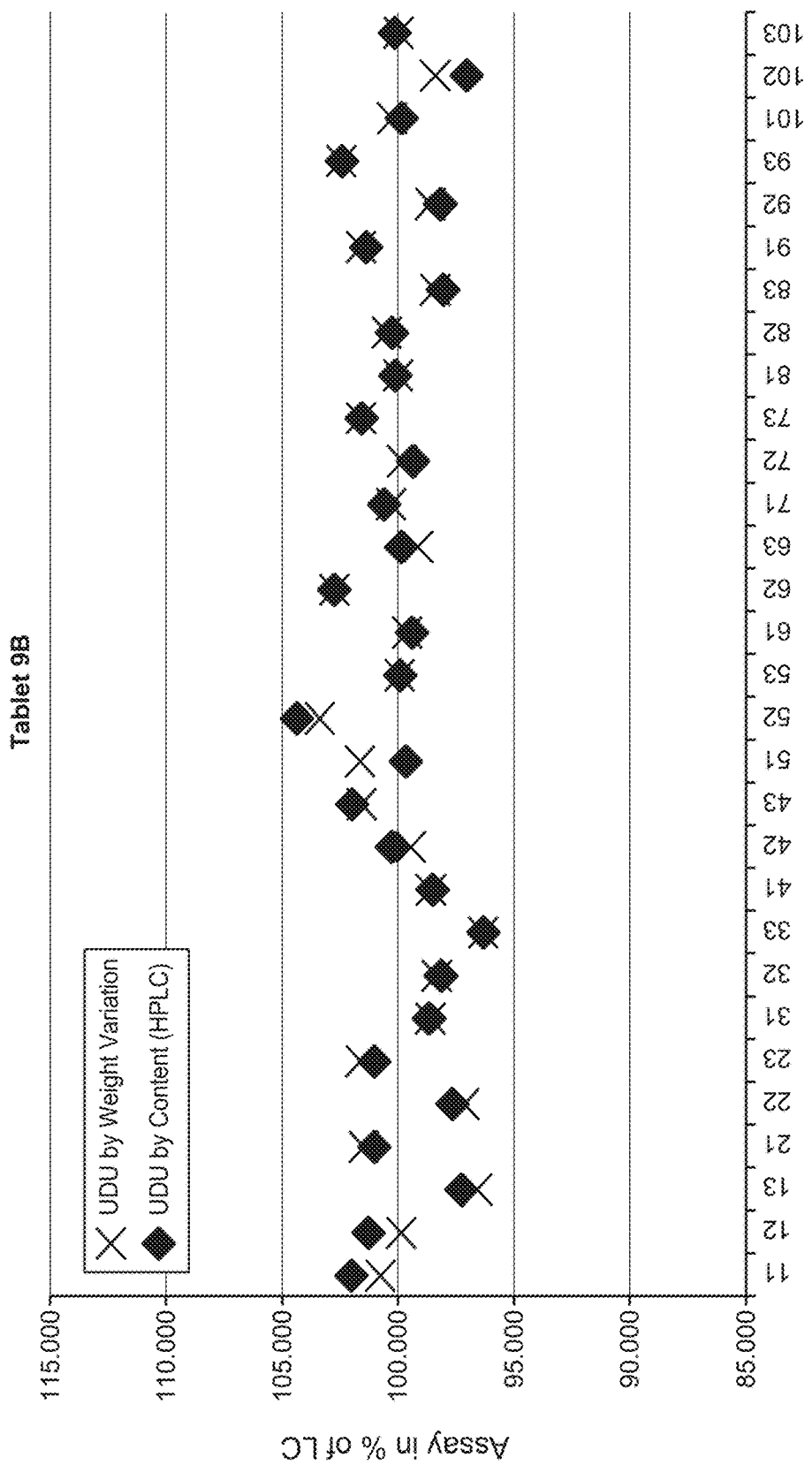
FIG. 12B is a plot of the comparison of tablet weight variation with content uniformity for tablets manufactured using an active drug with a particle size D [v, 0.5] of 38 μm.
Figure 12C:
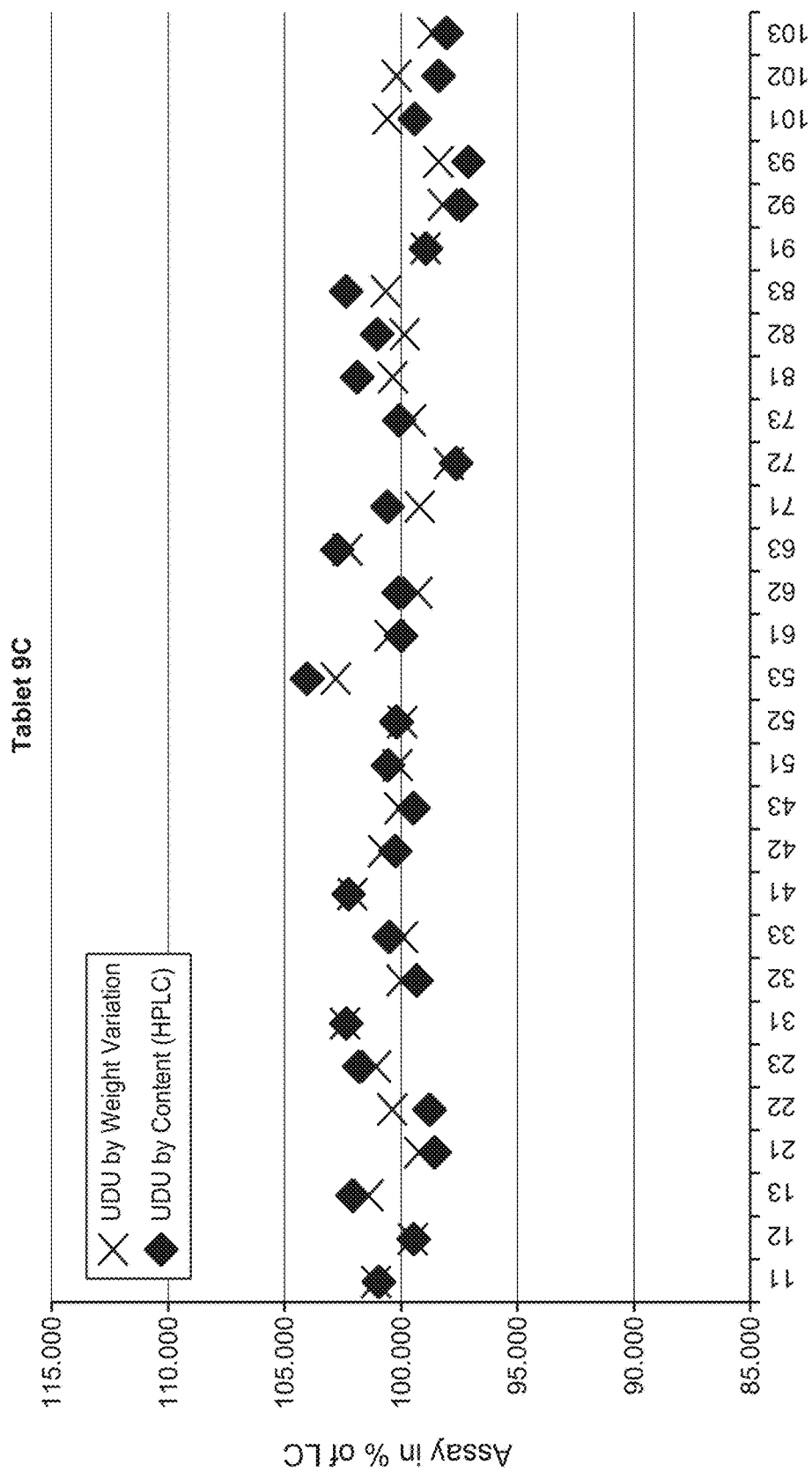
FIG. 12C is a plot of the comparison of tablet weight variation with content uniformity for tablets manufactured using an active drug with a particle size D [v, 0.5] of 47 μm.

The results are displayed in FIG. 12A, FIG. 12B and FIG. 12C. The plots show good correlation between tablet weight and content of active drug, demonstrating homogeneity with respect to active drug content when operating under the normal operating conditions for pre-blending, following processing through the subsequent manufacturing steps.

Example 10

A series of pilot scale roller compaction and tablet compression experiments were performed at fixed pre-blending and final blending process conditions for tablets corresponding to prototype tablet 3 to evaluate the effect of roller compaction settings on tablet core attributes of disintegration time (s), % dissolution after 15 minutes, main compression force variability (relative standard deviation [RSD] %), and table hardness (N). The screening roller compaction and tableting compression variables are summarized in Table 10A below.

TABLE 10A

| Variable | −1 | 0 | +1 |
|---|---|---|---|
| Roller Compaction and Screening | | | |
| Roller Compaction Force (kN/cm) | 3 | 5 | 8 |
| Roller Compaction Gap Size (mm) | 2 | 3 | 4 |
| Milling Screen Size (mm) | 0.8 | 1.0 | 1.25 |
| Tableting | | | |
| Main Compression Force (kN) | 15 | 20 | 25 |
| Rotor Speed (rpm) | 30 | 45 | 60 |
| Feed Frame Speed (rpm) | 30 | 55 | 80 |

The experiments showed that tablet hardness and variability in main compression force were impacted by rotor speed and main compression force ("MCF") force (data not shown). Increasing rotor speed and increasing main compression force led to tablets with slightly higher tablet hardness. Main compression force variability increased slightly with increasing rotor speed and decreasing main compression force. Feed frame speed appeared to have no impact on any of the attributes over the ranges studied. There was no correlation between tablet hardness and either disintegration time of the tablets or % dissolution after 15 minutes.

Example 11

Following these experiments and the observations on scale-up, a range of pilot scale experiments was performed wherein tablet cores corresponding to prototype tablet 3 were formed at 10 kN and 18.5 kN main compression force was studied using a roller compaction force of 5 kN/cm, a 3 mm roller compaction gap size and a 2 kN precompression force. The experiments showed that a main compression force of 10 kN gave about 46% acceptable cores and a main compression force of 18.5 kN gave about 98% acceptable cores.

Results from the experiments confirmed the conclusions from Example 10 with respect to main effects. It was also evident from these experiments that lower precompression force and especially higher main compression force reduces sticking tendency, leading to less punch filming and higher percentage of acceptable cores.

Example 12

In Example 12 the effect of active drug particle size distribution, roller compaction force, and roller compaction gap size on final blend and tablet core for tablets corresponding to prototype tablet 3 was evaluated. Pre-blending was done in a Bohle 100 L bin blender at first blend conditions of 30 minutes at 6 rpm and at second blend conditions of 8 minutes at 6 rpm. A Gerteis Mini-Pactor roller compactor with one smooth and one knurled roller was used in conjunction with integrated milling with a 1.0 mm screen. The final blend was done in a Bohle 100 L bin blender at first blend conditions of 10 minutes at 6 rpm and at second blend conditions of 8 minutes at 6 rpm. Tablet compression was done on a 20-station Korsch XL200 WIP rotary tablet press. Main compression forces over the range 14 to 19 kN (center point 16.5 kN) were evaluated. Evaluated tablet core attributes included active drug uniformity, assay, dissolution at 15 and 30 minutes, disintegration time, hardness (crushing strength), abrasion, tablet weight variability (by weight range), variability of main compression force, and visual appearance. Additional final blend attributes of particle size distribution, bulk density, specific surface area (BET), and flowability were also monitored, and their correlation with ribbon at-gap density was investigated. The screening roller compaction and tableting compression variables are summarized in Table 12A below. In addition, a small portion of each final blend was compressed at a significantly reduced tablet compression force of 7 kN to examine the impact on tablet hardness, abrasion, disintegration time, and in vivo dissolution performance.

TABLE 12A

| Variable | −1 | 0 | +1 |
|---|---|---|---|
| Roller Compaction and Screening | | | |
| Roller Compaction Force (kN/cm) | 2 | 3.5 | 5 |
| Roller Compaction Gap Size (mm) | 2 | 3 | 4 |
| Active Drug Particle Size (D [v, 0.5])(mm) | 29 | 38 | 47 |
| Tableting | | | |
| Main Compression Force (kN) | 14 | 16.5 | 19 |

The final blend results are presented in Table 12B where roller compaction force ("RCF") is in kN/cm, Gap Size is in mm, Ribbon at-Gap Density is in g/mL, active drug particle size distribution ("PSD") is in D [v, 0.5] μm, final blend PSD is in D [v, 0.5] μm, Final Blend specific surface area by Brunauer-Emmett-Teller ("BET") theory is in m2/g and final blend flow function coefficient ("FFC") is at 1000 Pa

TABLE 12B

| Pattern | RCF | Gap Size | Active Drug PSD | Ribbon at-Gap Density | Final Blend PSD | Final Blend Bulk Density | Final Blend BET | Final Blend FFC |
|---|---|---|---|---|---|---|---|---|
| 0 | 3.5 | 3 | 38 | 1.07 | 89 | 0.57 | 1.3 | 4.9 |
| − − + | 2.0 | 2 | 47 | 0.99 | 80 | 0.53 | 1.1 | 6.1 |
| + − − | 5.0 | 2 | 29 | 1.17 | 198 | 0.59 | 1.6 | 4.5 |
| + + − | 5.0 | 4 | 29 | 1.15 | 98 | 0.57 | 1.5 | 3.8 |
| − + − | 2.0 | 4 | 29 | 0.94 | 68 | 0.48 | 1.1 | 5.3 |
| 0 | 3.5 | 3 | 38 | 1.07 | 91 | 0.58 | 1.2 | 5.2 |
| + − + | 5.0 | 2 | 47 | 1.17 | 231 | 0.57 | 1.4 | 4.9 |
| − + + | 2.0 | 4 | 47 | 0.95 | 73 | 0.52 | 1.0 | 6.5 |
| − − − | 2.0 | 2 | 29 | 1.00 | 82 | 0.50 | 1.2 | 5.1 |
| + + + | 5.0 | 4 | 47 | 1.10 | 102 | 0.54 | 1.4 | 4.2 |
| 0 | 3.5 | 3 | 38 | 1.08 | 100 | 0.52 | 1.3 | 4.9 |

Roller compaction force and gap size had an effect on at-gap density. Final blend particle size distribution, evaluated as D [v, 0.5], is affected by roller compaction force (numerically positive effect) and gap size (numerically negative effect) and their interaction. For bulk density only, roller compaction force had an effect.

Figure 13:
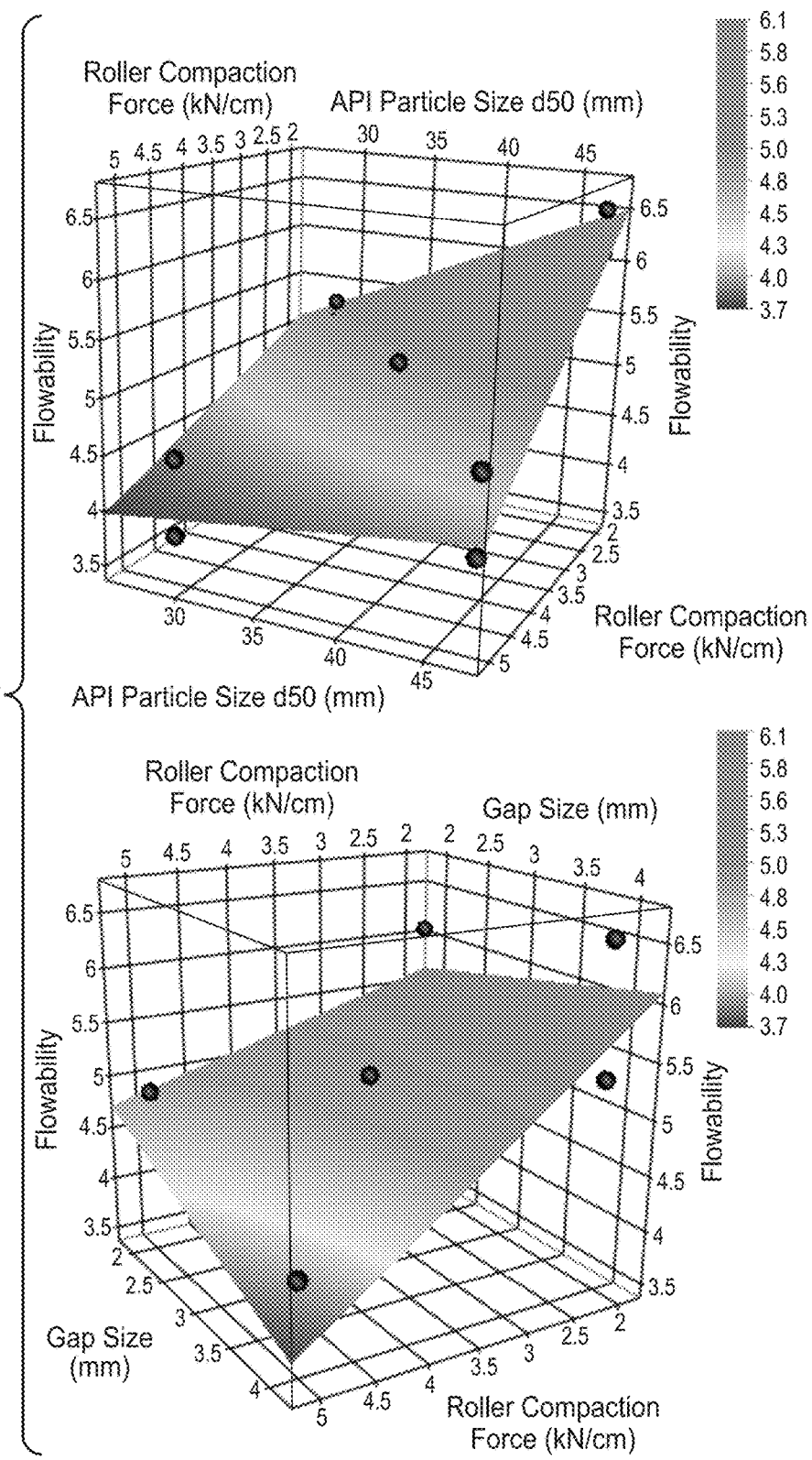
FIG. 13 depicts a three-dimensional surface plot of the effect of roller compaction force and active drug particle size distribution on flowability and a three-dimensional surface plot of the effect of roller compaction force and gap size on flowability.

Flowability of the final blend (R2=0.99), expressed as flow function coefficient, was measured using a ring shear cell at a pressure of 1000 Pa. The main factor impacting flowability appears to be roller compaction force (p=0.0001) where increasing force leads to final blend with poorer flow (lower FFC). Active drug particle size (where smaller particle size D [v, 0.5] leads to poorer flow; p=0.0013) and the interaction with roller compaction force (p=0.0203), and the interaction of roller compaction force and gap size (p=0.0060) also affect flowability. In summary, correlations between ribbon at-gap density and final blend properties show two different effects: (1) Higher ribbon at-gap density correlates with larger final blend PSD D [v, 0.5] and higher bulk density, as expected due to the higher degree of densification during roller compaction; (2) Higher ribbon at-gap density correlates with poorer flow properties, an observation that is opposite to the expectation; and (3) Higher roller compaction forces and lower active drug particle size impair flowability of the final blend and uniformity of die filling causing more variation to resulting MCFs wherein variation decreases slightly with increasing MCF (p=0.0035). Three-dimensional surface plots of roller compaction force and active drug particles size distribution on flowability and of roller compaction force and gap size on flowability are depicted in FIG. 13.

The final tablet core results are presented in Table 12C where "MCF" refers to main compression force (kN); "CU" refers to content uniformity (% RSD); Assay (%) refers to active drug assay; "Diss. 15 min" refers to % dissolution after 15 minutes; "Disint. Time" refers to average disintegration time in seconds; "Hard." refers to average hardness (N); "Abra." refers to abrasion (%); "Wt Rg" refers to weight range (mg) an is the maximum minus the minimum tablet weight; "Wt Var" refers to weight variation (% RSD); Var MCF" refers to variation in MCF; and "Vis App" refers to visual appearance (% good).

TABLE 12C

| Pattern | MCF | Batch | CU | Assay | Diss. 15 | Disint. Time | Hard. | Abra. | Wt Rg | Wt Var | Var MCF | Vis App |
|---|---|---|---|---|---|---|---|---|---|---|---|---|
| 0 | 16.5 | 1A | 1.9 | 99.9 | 94 | 189 | 59 | 0.4 | 12. | 1.6 | 7.4 | 66 |
|  | 14.0 | 1B | 2.0 | 99.2 | 94 | 145 | 60 | 0.3 | 8.9 | 1.6 | 7.6 | 60 |
| − − + | 19.0 | 2A | 1.0 | 100.9 | 96 | 163 | 58 | 0.4 | 7.8 | 1.1 | 5.3 | 61 |
|  | 14.0 | 2B | 1.3 | 100.9 | 97 | 147 | 59 | 0.3 | 5.7 | 1.0 | 6.1 | 57 |
| + − − | 14.0 | 3A | 2.8 | 99.5 | 95 | 140 | 58 | 0.3 | 12. | 2.0 | 11.9 | 42 |
|  | 19.0 | 3B | 2.7 | 99.3 | 93 | 179 | 61 | 0.4 | 13. | 2.2 | 9.6 | 48 |
| + + − | 19.0 | 4A | 2.9 | 99.3 | 95 | 179 | 61 | 0.3 | 11. | 2.1 | 10.1 | 100 |
|  | 14.0 | 4B | 2.6 | 99.7 | 92 | 160 | 59 | 0.3 | 16. | 3.0 | 11.8 | 97 |
| − + − | 14.0 | 5A | 1.9 | 98.4 | 96 | 127 | 57 | 0.4 | 12. | 2.1 | 10.1 | 84 |
|  | 19.0 | 5B | 1.9 | 97.5 | 92 | 121 | 59 | 0.3 | 12. | 2.1 | 8.8 | 86 |
| 0 | 16.5 | 6A | 2.3 | 100.6 | 94 | 152 | 60 | 0.4 | 11. | 2.0 | 7.8 | 67 |
|  | 16.5 | 6B | 1.4 | 99.3 | 94 | 141 | 63 | 0.3 | 7.3 | 1.3 | 7.3 | 68 |
| + − + | 19.0 | 7A | 1.6 | 100.3 | 91 | 213 | 56 | 0.4 | 9.1 | 1.6 | 7.9 | 45 |
|  | 14.0 | 7B | 2.0 | 99.7 | 93 | 202 | 52 | 0.4 | 11. | 1.6 | 9.2 | 34 |
| − + + | 14.0 | 8A | 1.0 | 101.2 | 98 | 130 | 55 | 0.5 | 6.8 | 1.2 | 6.2 | 92 |
|  | 19.0 | 8B | 1.7 | 100.2 | 95 | 157 | 52 | 0.4 | 7.1 | 1.2 | 5.8 | 93 |
| − − − | 19.0 | 9A | 2.5 | 99.4 | 95 | 170 | 63 | 0.4 | 12. | 1.7 | 8.0 | 57 |
|  | 14.0 | 9B | 2.0 | 98.5 | 95 | 167 | 61 | 0.3 | 10. | 1.7 | 9.4 | 54 |
| + + + | 14.0 | 10A | 2.1 | 101.2 | 97 | 177 | 57 | 0.4 | 9.9 | 1.8 | 8.3 | 93 |
|  | 19.0 | 10B | 1.5 | 101.0 | 96 | 178 | 58 | 0.4 | 8.7 | 1.6 | 7.6 | 99 |
| 0 | 19.0 | 11A | 1.8 | 100.0 | 93 | 175 | 57 | 0.4 | 10. | 1.7 | 7.2 | 58 |
|  | 16.5 | 11B | 1.4 | 100.1 | 95 | 184 | 58 | 0.4 | 8.9 | 1.6 | 8.2 | 56 |

The MCF variation can be linked to tablet weight range (R2=0.83) and content uniformity (R2=0.81) similarly with the effects of roller compaction force and active drug PSD. The % RSD of the individual content values of the sorted tablets was calculated. Content uniformity was improved (lower % RSD) at lower roller compaction forces and using active drug with a larger particle size. All results were less than 4% RSD.

Data, presented in previous examples suggest acceptable homogeneity of the blends and, therefore, content uniformity is primarily linked to variability in tablet weight. This conclusion is in alignment with the statistical evaluation of the Example 12 results, which shows interactions between content uniformity (% RSD), variation in MCF, and tablet weight range.

Figure 14:
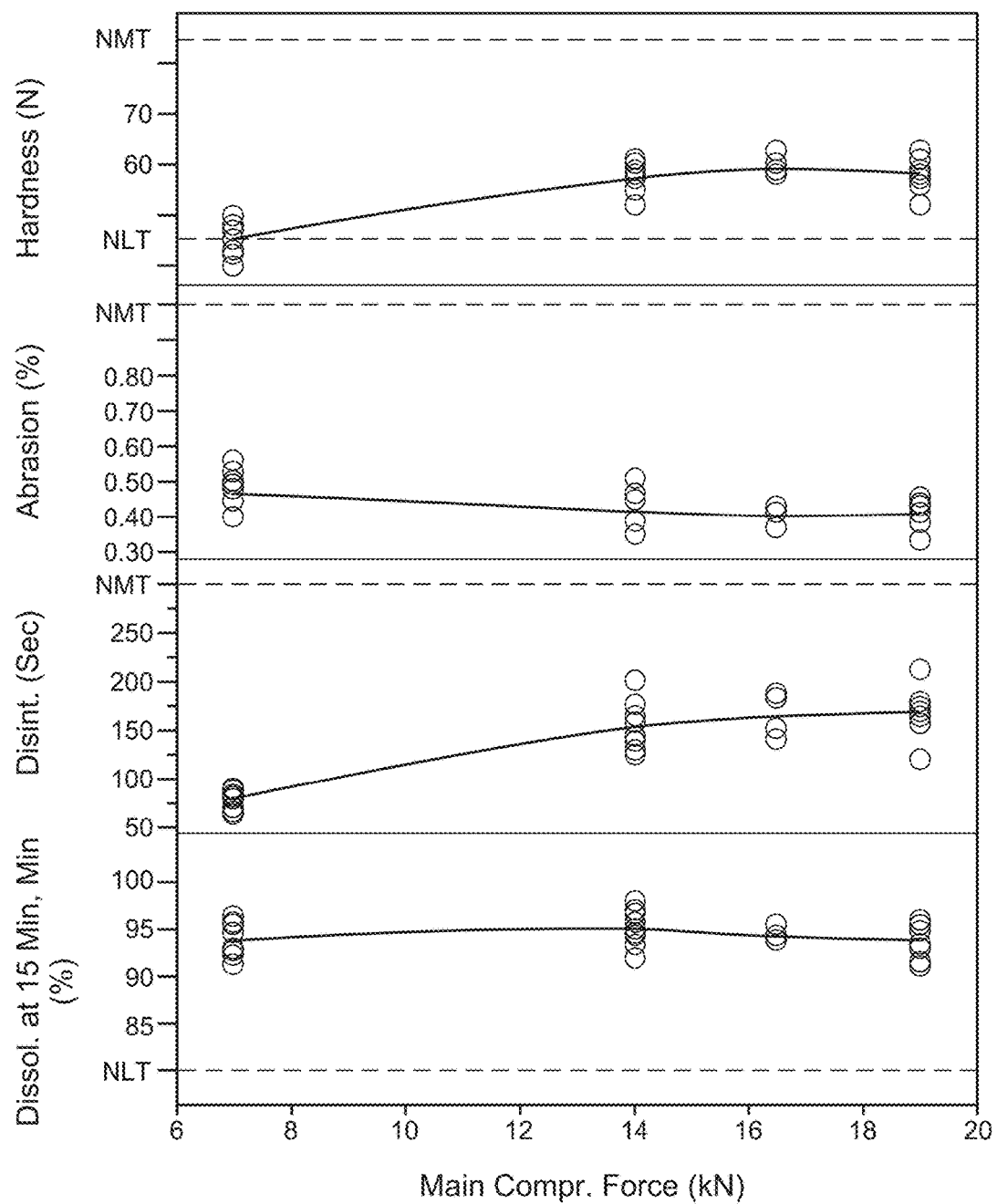
FIG. 14 is a scatter plot of main compression force versus tablet core hardness, abrasion, disintegration and dissolution.

Average tablet hardness ranges between 52 N and 61 N for tablets compressed at 14 kN, between 58 N and 63 N for tablets compressed at 16.5 kN, and between 52 N and 63 N for tablets compressed at 19 kN. This is consistent with the shape of the force-hardness profiles for the formulation that becomes almost flat above 14 kN. Tablets pressed at the reduced compression force of 7 kN have reduced hardness, in the range of 40-50 N. Tablet hardness is related to abrasion, disintegration time, and dissolution, as presented in FIG. 14 (where NLT means not less than and NMT refers to not more than); slight changes in these variables are only seen at the slightly reduced hardness of cores compressed at 7 kN. FIG. 14 demonstrates that acceptable abrasion performance, disintegration time, and dissolution were obtained with tablets pressed at 7 kN MCF, with obtained values far from the edge of failure.

Abrasion was tested using a modified version of the pharmacopedial friability test where the drum has multiple baffles (lamella); approximately 100 g of tablet cores are rotated for a total of 1250 revolutions at 100 rpm. This test is considered to be a more stringent test of the ability of tablets to withstand abrasion than the pharmacopedial friability test and is used to assess the suitability of tablet cores for the coating operation in a pan coater. Abrasion was found to be <0.6% under all of conditions tested. This is also valid for the tablets compressed at the significantly reduced compression force of 7 kN where the abrasion is only slightly increased (refer to FIG. 14). Statistically significant but negligible effects on abrasion (R2=0.76) were observed for active drug PSD and the interaction of roller compaction force and gap size.

Disintegration time did not exceed an average value of 213 seconds (n=6) under any of the conditions examined. Disintegration times are significantly reduced for tablets compressed at the low compression force of 7 kN. Roller compaction force, was found to have a positive effect on disintegration (R2=0.68).

Minor influences of roller compaction and main compression forces are apparent after 15 minutes dissolution, with increased roller compaction and compression forces leading to slightly reduced % dissolution in the range of 91% to 98% dissolved. Dissolution values after both 15 and 30 minutes are in the range of >80%, with minimum values under all of the conditions examined of 91% after 15 minutes and 92% after 30 minutes. Dissolution was not significantly impacted for tablets compressed at the reduced compression force of 7 kN.

Appearance was assessed by inspection of a sample of 320 tablet cores, collected at 10 timepoints across the whole compression process. The appearance of the tablet core surface was ranked not acceptable whenever dents on the core cap were present independent of the dent size. Dents occur due to punch filming; sticking/deposition of the final blend (mainly active drug) to the punch tip, which increases over time, causing an impression on the tablet surface.

The data indicate that roller compaction gap size is the most influential factor on tablet appearance (R2=0.94), as measured by percentage of good cores. Increasing gap size strongly reduces punch filming/sticking; hence, less dents are observed. Additionally, the interaction of gap size and roller compaction force has an effect. For main compression force, a range of 14 kN to 19 kN was evaluated wherein higher MCF reduces punch filming/sticking tendency.

Overall, based on the experimental results, roller compaction and tablet compression operations can impact processability and the quality attributes of the tablet cores as follows. First, roller compaction force as well as active drug particle size have an impact on flowability of the resultant final blends. Higher roller compaction force and smaller active drug particle size lead to final blends with lower FFC values (poorer flow). Second, roller compaction force and active drug PSD have an impact on tablet weight variation, expressed as weight range, on variability of main compression force during tablet compression and on content uniformity. Tablet weight range and MCF variability increase while content uniformity decreases with increasing roller compaction force and decreasing active drug particle size, which may be linked to poorer flowability of the final blend. Third, roller compaction gap size has an impact on sticking/filming of the punches during tablet compression and on the tablet appearance. Smaller gap size leads to granules that are more cohesive, leading to an increase in filming of the punches and a greater number of tablets with poor appearance (increased number of dents). Finally, although main compression force during tableting has an impact on disintegration, tablets pressed at main compression forces in the range 14 to 19 kN, and at 7 kN, to investigate tablets with lower hardness, all show acceptable abrasion, disintegration, and in vitro dissolution performance.

Example 13

Commercial scale tableting batches for tablets corresponding to prototype tablet 3 were done at a roller compaction gap size in the range of 3 to 5 mm, at a roller compaction force range of 2 to5 kN/cm and at a tableting main compression force of 14 to 19 kN. The gap size range was higher than compared with previous pilot scale experimental evaluations (i.e., 2-4 mm) due to the observed effect of gap size on physical appearance. Compression was performed on each batch of final blend with two center points and one additional run to produce a total of 11 batches of tablet cores. Experiments were performed at a scale of 50.4 kg of final blend to produce up to 420,000 tablet cores. Batches were produced at target at-gap density values of 0.92 (low densification), 1.03 (center point), and 1.14 g/mL (high densification) by varying roller compaction force and gap size. An active drug with a particle size (D [v, 0.5]) of 38 µm was used to produce all batches. Experiments were performed on the intended commercial equipment using a Gerteis Mini-Pactor for roller compaction with integrated milling and using a 21-station Fette 1090i WIP rotary tablet press for compression.

For the active drug particle size distribution D [v, 0.5], bulk density, specific surface area, and flowability results from the final blend, a standard least-squares linear model was estimated. This model included the main term ribbon at-gap density and no interaction terms. For results that were obtained after completion of both roller compaction and tablet compression, the model was extended by the factors main compression force and rotor speed, and the corresponding interaction terms of the three factors.

The screening roller compaction and tableting compression variables are summarized in Table 13A below.

TABLE 13A

| Variable | −1 | 0 | +1 |
| --- | --- | --- | --- |
| Roller Compaction and Screening | | | |
| Ribbon at-Gap Density (g/mL) | 0.92 | 1.03 | 1.14 |
| Roller Compaction Force (kN/cm) | 2 | 3.5 | 5 |
| Roller Compaction Gap Size (mm) | 5 | 4 | 3 |
| Tableting | | | |
| Main Compression Force (kN) | 14 | 16.5 | 19 |
| Rotor Speed (rpm) | 30 | 45 | 60 |

The experimental results for the final blend properties are presented in table 13B below where "RCF" refers to roller compaction force (kN/cm); "Gap" refers to roller gap size (mm); "PSD" refers to final blend particle size distribution (D [v, 0.5]); "Density" refers to final blend density (g/mL), "BET" refers to final blend specific surface area by Brunauer-Emmett-Teller theory; and "FCC" refers to final blend flow function coefficient at 1000 Pa.

TABLE 13B

| Pattern | Batch | RCF | Gap | At-Gap Density (g/mL) | | Final Blend | | | |
| | | | | Target | Actual | PSD | Density | BET | FCC |
| --- | --- | --- | --- | --- | --- | --- | --- | --- | --- |
| 0 | 4/02 | 3.5 | 4 | 1.03 | 1.13 | 86 | 0.56 | 1.3 | 5.4 |
| + | 5/02 | 5.0 | 3 | 1.14 | 1.24 | 131 | 0.59 | 1.5 | 5.7 |
| + | 5/02 | 5.0 | 3 | 1.14 | 1.24 | 131 | 0.59 | 1.5 | 5.7 |
| − | 6/02 | 2.0 | 5 | 0.92 | 0.95 | 72 | 0.51 | 1.1 | 6.2 |
| + | 7/02 | 5.0 | 3 | 1.14 | 1.19 | 148 | 0.59 | 1.5 | 4.9 |
| − | 8/02 | 2.0 | 5 | 0.92 | 0.93 | 69 | 0.51 | 1.0 | 6.9 |
| − | 8/02 | 2.0 | 5 | 0.92 | 0.93 | 69 | 0.51 | 1.0 | 6.9 |
| + | 9/02 | 5.0 | 3 | 1.14 | 1.18 | 128 | 0.63 | 1.5 | 5.4 |
| − | 10/02 | 2.0 | 5 | 0.92 | 0.95 | 71 | 0.51 | 1.1 | 6.1 |
| − | 10/02 | 2.0 | 5 | 0.92 | 0.95 | 71 | 0.51 | 1.1 | 6.1 |
| 0 | 11/02 | 3.5 | 4 | 1.03 | 1.07 | 86 | 0.56 | 1.3 | 5.8 |

Flowability was impacted by the factor ribbon at-gap density, with increasing density (increased roller compaction force and decreased roller compaction gap size) leading to a final blend with poorer flow (lower FFC). The shift in the lower range of gap size (from 2 mm in previous pilot scale examples to 3 mm) resulted in a final blend with finer PSD and better flow (higher FFC values) at the higher densification range. Flow Function Coefficient was greater than the target value of at least 4 under all combinations of parameters studied, with a minimum value of 4.9.

The results of Example 13 were consistent with previous pilot scale examples and the same correlations between ribbon at-gap density and final blend properties were apparent. Ribbon at-gap density had an effect on final blend PSD (D [v, 0.5]) as well as on bulk density and BET. As demonstrated in previous pilot scale examples, higher ribbon at-gap density leads to a final blend with larger PSD, higher bulk density, and an increased surface area (BET).

The experimental data further show that ribbon at-gap density, main compression force and rotor speed, have an impact on the variability of MCF (R2=0.96). MCF variability is lower with granules of lower density (lower at-gap density). As the ribbon at-gap density is mainly influenced by roller compaction force, this is consistent with previous pilot scale examples where roller compaction force showed a significant effect on variability of MCF. Variability is also decreased at high MCFs and slower rotation speeds of the tablet press. Variation in MCF was reduced in Example 13 as compared to previous pilot scale examples, and MCF variability was not more than 6.6% under all combinations of parameters studied.

The final tablet core results are presented in Tables 13C and 13D. The process parameters are presented in Table 13C where: "RCF" refers to roller compression force (kN/cm); "Gap" refers to gap size (mm); "Density" refers to at-Gap Density (g/mL); "Speed" refers to rotor speed (rpm); and "MCF" refers to main compression force (kN). The Experimental results are reported in Table 13D where: "CU" refers to content uniformity (% RSD); Assay (%) refers to active drug assay; "Diss. 15 min" refers to % dissolution after 15 minutes; "Disint. Time" refers to average disintegration time in seconds; "Hard." refers to average hardness (N); "Abra." refers to abrasion (%); "Wt Rg" refers to weight range (mg) an is the maximum minus the minimum tablet weight; "Wt Var" refers to weight variation (% RSD); Var MCF" refers to variation in MCF; and "Vis App" refers to visual appearance (% good) of 210,000 tablets.

TABLE 13C

| | | | | At-Gap Density | | | |
| Pattern | Batch | RCF | Gap | Target | Actual | Speed | MCF |
| --- | --- | --- | --- | --- | --- | --- | --- |
| 0 0 0 | 04/03 | 3.5 | 4 | 1.03 | 1.13 | 45 | 16.5 |
| + − − | 05/03 | 5.0 | 3 | 1.14 | 1.24 | 30 | 14 |
| + − + | 05/04 | 5.0 | 3 | 1.14 | 1.24 | 30 | 19 |
| − − + | 06/03 | 2.0 | 5 | 0.92 | 0.95 | 30 | 19 |
| + + − | 07/03 | 5.0 | 3 | 1.14 | 1.19 | 60 | 14 |
| − + + | 08/03 | 2.0 | 5 | 0.92 | 0.93 | 60 | 19 |
| − 0 0 | 08/04 | 2.0 | 5 | 0.92 | 0.93 | 45 | 16.5 |
| + + + | 09/03 | 5.0 | 3 | 1.14 | 1.18 | 60 | 19 |
| − − − | 10/03 | 2.0 | 5 | 0.92 | 0.95 | 30 | 14 |
| − + − | 10/04 | 2.0 | 5 | 0.92 | 0.95 | 60 | 14 |
| 0 0 0 | 11/03 | 3.5 | 4 | 1.03 | 1.07 | 45 | 16.5 |

TABLE 13D

| Pattern | Batch | CU | Assay | Diss. 15 min | Disint. Time | Hard. | Abra. | Wt Rg | Wt Var | Var MCF | Vis App |
| --- | --- | --- | --- | --- | --- | --- | --- | --- | --- | --- | --- |
| 0 0 0 | 04/03 | 1.5 | 99.9 | 95 | 180 | 60 | 0.25 | 5.1 | 0.86 | 4.5 | 100 |
| + − − | 05/03 | 2.4 | 99.7 | 95 | 193 | 62 | 0.23 | 9.9 | 1.25 | 5.3 | 100 |
| + − + | 05/04 | 1.4 | 100.8 | 98 | 207 | 62 | 0.26 | 7.7 | 1.22 | 4.3 | 100 |
| − − + | 06/03 | 1.3 | 98.9 | 96 | 155 | 57 | 0.28 | 5.7 | 0.85 | 2.4 | 100 |
| + + − | 07/03 | 1.5 | 100.5 | 96 | 190 | 63 | 0.25 | 7.4 | 1.04 | 6.6 | 99 |
| − + + | 08/03 | 2.1 | 98.6 | 96 | 150 | 72 | 0.24 | 7.7 | 1.10 | 3.9 | 100 |
| − 0 0 | 08/04 | 1.0 | 97.6 | 95 | 156 | 68 | 0.26 | 6.1 | 0.77 | 3.7 | 100 |
| + + + | 09/03 | 1.6 | 101.0 | 96 | 214 | 62 | 0.32 | 10.5 | 1.35 | 4.9 | 100 |
| − − − | 10/03 | 1.4 | 99.3 | 96 | 149 | 61 | 0.30 | 7.0 | 0.85 | 4.0 | 100 |
| − + − | 10/04 | 1.0 | 98.4 | 96 | 141 | 64 | 0.28 | 6.2 | 1.00 | 4.9 | 100 |
| 0 0 0 | 11/03 | 1.7 | 99.2 | 93 | 187 | 64 | 0.24 | 8.5 | 1.27 | 4.8 | 100 |

Tablet weight and content uniformity show low RSD values of not more 1.4% for tablet weight RSD and not more than 2.4% for content uniformity RSD, which confirms the process robustness for all combinations of parameters studied. Tablets tested were within the individual tablet weight acceptance limits of 111.0 to 129.0 mg (±7.5% of the nominal press weight of 120.0 mg). The difference between maximum and minimum single tablet weight was in the range of 5.1 to 10.5 mg for tablets manufactured under all conditions. Content uniformity and % RSD of the individual values was assessed using the same methods as in previous pilot scale examples.

The interaction of ribbon at-gap density and main compression force as well as the interaction of MCF and rotor speed showed an effect on % RSD of content uniformity.

Assay of tablet batches under all conditions tested is in the acceptable range of 95.0% to 105.0% of label claim, ranging from 97.6% to 101.0%.

Data from Example 13 is consistent with the results of previous pilot scale examples and the shape of the force-hardness profiles for the formulation. No significant factors impacting tablet hardness over the range studied were indicated. Average tablet hardness ranged between 61 and 64 N for tablets compressed at 14 kN, between 60 N and 68 N for tablets compressed at 16.5 kN, and between 57 N and 72 N for tablets compressed at 19 kN. The data support the use of an in-process control hardness test on tablet cores based on average tablet core hardness of 45 N (minimum), to ensure process and product quality control.

Abrasion was tested using the same method used for testing of samples of previous pilot scale examples. Abrasion results were low for tablet cores produced under all conditions examined with a maximum loss of 0.32%.

In line with the results from previous pilot scale examples, experimental data show acceptable disintegration for tablet cores produced under all of the conditions tested and disintegration time did not exceed an average value of 214 seconds (n=6). Ribbon at-gap density was found to have a positive effect on disintegration (R2=0.96). Dissolution was not impacted by any of the factors evaluated in Example 13.

Appearance testing is performed on 320 tablet cores for batch sizes of 210,000 tablets and on 640 tablet cores for batches of 420,000 tablets using the method of previous pilot scale examples. The number of tablet cores without dents was reported as percentage of good cores. For all except one batch, results from Example 13 (at commercial scale and on the intended commercial manufacturing equipment) show that 100% of tablets assessed have acceptable appearance (no evidence of tablet sticking). The single batch that showed minor tablet sticking was manufactured under the conditions predicted to be worst (i.e., the conditions that were expected to produce most appearance defects based on the results of previous pilot scale examples) and having the smallest gap size (3.0 mm), highest roller compaction force (5.0 kN/cm), and lowest MCF (14 kN). This batch had 91% tablet cores with acceptable appearance of 640 tablet cores tested for the full-scale batch size (420,000 tablets).

Statistical evaluation was performed for the results of Example 13. The mean of all results was well removed from the edge of failure. Moreover, the ranges of all batches for all results (i.e., all individual values) met acceptance criteria set. Under all combinations studied in Example 13, drug product of acceptable quality was produced.

The following impacts on processability and quality attributes of the tablet cores have been found. First, the impact of ribbon at-gap density on the resultant final blend properties flowability, PSD, bulk density, and BET were confirmed. As ribbon densification increases, final blend with lower FFC values (poorer flow) is produced. Second, Ribbon at-gap density, main compression force and rotation speed of the tablet press have an impact on the variability of MCF. It was confirmed that main compression force variability is lower with final blends that have been less densified during roller compaction (lower at-gap density), which can be linked with improved flowability of the final blend. Variability is slightly reduced at increased main compression force and decreased rotation speed. Shifting the gap size from 3 to 5 mm (compared to 2 to 4 mm in previous pilot scale examples), a final blend with better flowability was obtained, reducing overall the MCF variability compared to previous pilot scale examples. The same applies for the core weight variability, which shows a correlation with the variability of main compression force. Third, tablet compression rotor speed had a significant effect only on the variability of MCF, with low magnitude. There was no impact on tablet core attributes (e.g., hardness). Therefore, it can be concluded that no impact on drug product quality attributes is expected from varying the rotor speed in the evaluated range.

In summary, the Example 13 commercial scale trial confirmed the results of previous pilot scale examples in that a reduced degree of densification during roller compaction produces granules that perform better during tableting (better flowability, lower variability in MCF, and lower tablet weight variability). Appearance of the cores was good; only a single batch, produced under the predicted worst conditions (highest densification and lowest MCF), showed any dents (all other batches produced 100% of tablet cores without dents). Disintegration was fast and dissolution was not impacted by any of the factors studied.

Example 14

In previous examples, the impact of active drug particle size on processability and the drug product attributes were examined at pilot scale (105,000 units for cores). Results generated during these experiments demonstrated that an active drug with a smaller particle size showed more variability during processing. Further trials were, therefore, performed at commercial scale (420 000 units, using the intended commercial manufacturing equipment) with an active drug with smaller D [v, 0.5] for tablets corresponding to prototype tablet 3 in order to confirm observed effects and the magnitude thereof. An overview of these batches is presented in Table 14A where "PSD" refers to active drug particle size distribution (D [v, 0.5] µm); "RCF" refers to roller compaction force (kN/cm), "Gap Size" refers to roller compaction gap size (mm); "At-Gap Density" refers to actual at-gap density (g/mL); "MCF" refers to main compression force (kN); and "Speed" refers to rotor speed in rpm where batch 0032 was compressed to tablets partially with 45 rpm and with 60 rpm.

TABLE 14A

| Batch | PSD | RCF | Gap Size | At-Gap Density | MCF | Speed |
|---|---|---|---|---|---|---|
| 0032 | 29 | 5 | 4 | 1.17 | 14 | 45 60/45 |
| 0043 | 27 | 2 | 5 | 0.98 | 16.5 | 60 |
| 0044 | 27 | 4 | 5 | 1.14 | 16.5 | 60 |
| 0045 | 29 | 2 | 5 | 0.98 | 16.5 | 60 |
| 0046 | 32 | 2 | 5 | 0.96 | 16.5 | 60 |
| 0007 | 38 | 5 | 3 | 1.19 | 14 | 60 |
| 0035 | 38 | 2 | 5 | 0.94 | 16.5 | 60 |

Results of the experiments are presented in Table 14B wherein the result analysis method is the same as for previous examples.

TABLE 14B

| Batch | FCC | CU | Assay | Diss. 15 min | Disint. time | Hard. | Abra. | Wt Rg | Wt Var | Var MCF | Vis. App. |
|---|---|---|---|---|---|---|---|---|---|---|---|
| 0032 | 4.4 | 2 | 99.2 | 92 | 164 | 69 | 0.22 | 12 | 1.7 | 8.1 | 68 |
|  |  | 1.9 | 101.2 | 95 | 196 | 67 | 0.22 | 9.4 | 1.3 | 7.1 |  |
| 0043 | 5.1 | 1.4 | 100.3 | 97 | 160 | 67 | 0.24 | 9.3 | 1 | 4.1 | 95 |
| 0044 | 4.6 | 1.7 | 99.9 | 97 | 201 | 63 | 0.2 | 9.2 | 1.4 | 5.8 | 71 |
| 0045 | 5.2 | 1.5 | 99.4 | 98 | 159 | 67 | 0.23 | 8.1 | 1.4 | 4.9 | 96 |
| 0046 | 6.1 | 1.3 | 100.3 | 99 | 162 | 65 | 0.23 | 6.4 | 1 | 3.7 | 98 |
| 0007 | 4.9 | 1.5 | 100.5 | 96 | 190 | 63 | 0.25 | 7.4 | 1 | 6.6 | 91 |
| 0035 | 6.5 | 1.4 | 100 | 95 | 155 | 66 | 0.27 | 6.8 | 1 | 4.2 | 100 |

The experimental results confirm that an active drug with a smaller particle size distribution (D [v, 0.5]) leads to increased tablet weight variation and main compression force variation and uniformity of dosage units. This effect was observed under conditions of higher densification during roller compaction (higher roller compaction force and/or smaller gap size). However, conditions of lower densification did not show this influence. Under one theory, and without being bound to any particular theory, these effects may be linked with flowability of the final blends. The experimental results confirmed that increasing roller compaction force and smaller active drug particle size have a negative impact on flowability of the resultant final blend.

Smaller active drug particle size led to an increase in sticking/filming during tablet compression when using granules produced under conditions of higher densification during roller compaction (5 kN/cm). Active drug with a smaller D [v, 0.5] led to a greater number of tablets with poor appearance (increased number of dents). This impact of higher roller compaction force on appearance of the tablet cores was also apparent for a gap size of 5 mm.

The appearance of all film-coated tablets manufactured with reduced densification during roller compaction (2 kN/cm, 5 mm) was acceptable independent of the active drug particle size used (D [v, 0.5] 27 to 38 µm), when the batches were tested against commercial acceptance criteria.

In summary, for an active drug with a particle size of D [v, 0.5] 27 μm, tablet appearance and processability were proven to be acceptable on commercial scale (by use of a gap size of 5 mm and force of 2 kN/cm during roller compaction). The experiments confirmed that active drug particle size has an impact on flowability of the final blend (in interaction with roller compaction force) and thus variability during tablet manufacturing and content uniformity of the drug product. Furthermore, manufacturing of full-scale batches revealed an effect of active drug particle size and roller compaction force on tablet appearance, in addition to the known impact of gap size.

Example 15

Film-coating experiments were performed at a pilot scale of 50,000 tablets (6.0 kg tablet cores) using tablet cores from two batches of tablet cores corresponding to prototype tablet 3. The design of the coating experiment is detailed in Table 15A below.

TABLE 15A

| Factor | −1 | 0 | +1 |
| --- | --- | --- | --- |
| Coating suspension solid content (%) | 14 | 17 | 20 |
| Spray rate (g/min) | 7.5 | 10.0 | 12.5 |
| (Spray rate [g/min per kg cores]) | (1.25) | (1.67) | (2.08) |
| Target product temperature (° C.) | 40 | 42.5 | 45 |

Target settings and experimental results are reported in Table 15B where: "Solids" refers to solids content (%); "Rate" refers to target spray rate (g/min); "Temp" refers to target product temperature (° C.); "Speed" refers to actual pan speed (rpm); "Time" refers to actual spray time (min); "Diss. 15" refers to % dissolution after 15 minute (%); "Disint" refers to average disintegration time (sec); "App" refers to average appearance score; and "LOD" refers to loss on drying (%).

TABLE 15

| Pattern | Solids | Rate | Temp | Speed | Time | Diss. 15 | Disint. | App | LOD |
| --- | --- | --- | --- | --- | --- | --- | --- | --- | --- |
| − 0 + | 14 | 10 | 45 | 4-14 | 177 | 93 | 171 | 3.0 | 1.7 |
| 0 − 0 | 17 | 7.5 | 42.5 | 7-12 | 215 | 93 | 173 | 2.6 | 1.8 |
| − + + | 14 | 12.5 | 45 | 8-14 | 139 | 95 | 188 | 2.6 | 1.6 |
| − − + | 14 | 7.5 | 45 | 8-14 | 227 | 94 | 205 | 2.0 | 1.6 |
| − + − | 14 | 12.5 | 40 | 12-14 | 138 | 94 | 156 | 2.8 | 2.2 |
| 0 0 0 | 17 | 10.0 | 42.5 | 12-14 | 164 | 97 | 133 | 2.8 | 1.8 |
| + + − | 20 | 12.5 | 40 | 13-14 | 118 | 91 | 167 | 3.4 | 1.8 |
| + + + | 20 | 12.5 | 45 | 12-14 | 118 | 95 | 155 | 3.0 | 1.8 |
| + − + | 20 | 7.5 | 45 | 10-14 | 193 | 93 | 199 | 2.4 | 1.5 |
| + − − | 20 | 7.5 | 40 | 10-14 | 186 | 94 | 176 | 2.8 | 2.0 |
| 0 0 0 | 17 | 10 | 42.5 | 10-14 | 173 | 93 | 165 | 2.6 | 2.0 |
| − − − | 14 | 7.5 | 40 | 13-14 | 227 | 95 | 155 | 2.0 | 2.1 |

Product temperature has the largest impact on average disintegration time (n=6), with increased temperature leading to an increase in disintegration time. However, the effect is not statistically significant (p=0.156) and the model is poor (R2=0.57), in line with expected results, as the coating process parameter should have a low-to-no effect on either disintegration or dissolution for the applied nonfunctional coating. All average disintegration times were in the acceptable range of no more than 300 seconds (range of 133 to 205 seconds), with the longest time of 205 seconds being obtained with the combination of low solids content, low spray rate (hence longest spray time), and highest product temperature.

Average dissolution at 15 minutes (n=6 tablets) was measured. No factors were found to be statistically significant for in vitro dissolution performance (R2=0.43). Average dissolution results at 15 minutes were all in the acceptable range (at least 80%) and ranged between 91% and 97%.

Appearance was assessed independently by five individual scientists. A sample of film-coated tablets from each of the DoE runs was ranked for appearance on a scale of 1 to 6. Appearance score 1 refers to very good film-coating appearance with smooth and shiny surface; debossing has sharp, fine edges. Appearance score 2 refers to good film-coating with quite smooth surface and some polish; debossing has sharp edges. Appearance score 3 refers to acceptable film-coating appearance with some noticeable roughness; debossing is less distinct. Appearance score 4 refers to sufficient film-coating appearance with noticeable roughness; debossing is more blurry. Appearance score 5 refers to poor film-coating appearance. Negative appearance aspects might include film defects, signs of orange peel and/or blurry debossing. Some filling might be visible. Appearance score 6 refers to very poor film-coating appearance. Extensive film defects and/or orange peel visible. Debossing difficult to read. Some filling might be visible. Spray rate was the only statistically significant (p=0.0253) factor in the statistical model for appearance (R2=0.78). Solid content in the coating suspension and the interaction between solid content of the coating suspension and product temperature also have impacts on appearance, but these were determined to not be statistically significant. Decreased spray rate and decreased solid content in the coating suspension lead to tablets with improved appearance (a lower score as ranked according to the appearance criteria).

Example 16

The coating parameters evaluated in Example 16 were optimized and confirmed at the intended commercial manufacturing scale using the commercial equipment and using tablets corresponding to prototype tablet 3. The spray rate [g/min per kg cores] of 1.25 to 2.08 g/min per kg of cores evaluated Example 15 was shifted slightly for scale-up in order to take advantage of the positive effect of slower spray rates on appearance. An initial feasibility batch was processed starting under "dry conditions" (spray rate 1.0 g/min per kg, product temperature 47° C.), with the second half of the batch processed under "wet conditions" (spray rate 1.9 g/min per kg, product temperature 39° C.). Neither spray drying (indicated by dust formation) nor sticking of tablets (indicator for conditions that are too wet) was observed, and the proposed ranges were considered feasible at scale.

Inlet air volume was successfully scaled to the intended commercial batch size, at 1200 m³/h, and spray pressure was fixed at 2.0 bar. The spray nozzles were fixed at 20 cm distance from the core bed at a spray angle of about 90°, with adjustment of the angle possible in response to the movement of the core bed. Pan rotation was increased throughout processing from 9 rpm to 14 rpm in 1 rpm increments. At the highest rotation speed of 14 rpm, the motion of the core bed was turbulent and was therefore decreased to 12 rpm for the remaining film coating process. The appearance of this batch was scored at 2.7 (acceptable to good appearance) according to the criteria described in Example 15.

Following coating of the feasibility batch, three batches were coated at the driest, wettest, and center points of the coating parameter ranges proposed for the commercial scale. Cores that were manufactured at the extremes of the conditions and center points for the roller compaction and tablet compression unit were used. Pan rotational speed was increased throughout processing from 8 to 12 rpm as required to maintain a spray angle of about 90° following the core bed movement. The conditions under which these batches were produced are detailed in Table 16A below. Appearance scores are also presented in Table 16A and are all in the acceptable range. These results confirm findings from the Example 15 that smoothness of the film coat is improved at a lower spray rate. However, all batches met all acceptance criteria (including release testing). The dissolution profiles of these batches manufactured at the commercial facility were comparable to the pilot scale batches.

TABLE 16A

| Description | Dry Coating | Wet Coating | Center Point |
|---|---|---|---|
| Batch No. | 0006/04 | 0007/04 | 0004/04 |
| Roller Compaction Force (kN/cm) | 2 | 5 | 3.5 |
| Roller Compaction Gap Size (mm) | 5 | 3 | 4 |
| Main Compression Force (kN) | 19 | 14 | 16.5 |
| Spray rate (g/min per kg) set/actual values | 1/0.96 | 1.9/1.85 | 1.45/1.4 |
| Pan rotation range (rpm) | 8-11 | 8-12 | 8-12 |
| Product temperature (° C.) set/actual | 47/47 | 39/40 | 43/43 |
| Coating suspension solid content (w/w %) | 14 | 14 | 14 |
| Inlet air volume (m³/h) set/actual | 1200 | 1000 | 1100 |
| Spray time (min) | 306 | 159 | 210 |
| Appearance score | 1.9 | 3 | 2.3 |
| LOD (%) | 1.6 | 2.3 | 1.9 |

All conditions produced film-coated tablets with acceptable appearance (scores in the range of 2.3 to 2.8), far from the edge of failure (score>4). A positive influence of lower spray rate on appearance was confirmed. Additionally, the increase of product temperature led to a slight improvement in appearance of the film coated tablets. Comparing the appearance results of batches manufactured with high product temperature and low or high spray rate, the difference was small. Therefore, for a tablet core load of 35 to 48 kg, the conditions of spray rate of 1 to 1.9 g/min per kg cores, product temperature of 39 to 47° C., inlet air volume of 1000 to 1200 m³/h, pan rotational speed between 8 rpm and 14 rpm, and solid content of coating suspension of 14% are acceptable to optimize appearance and to optimize processing time.

When introducing elements of the present disclosure or the embodiment(s) thereof, the articles "a", "an", "the" and "said" are intended to mean that there are one or more of the elements. The terms "comprising," "including," "containing" and "having" are intended to be inclusive and mean that there may be additional elements other than the listed elements. The use of terms indicating a particular orientation (e.g., "top", "bottom", "side", etc.) is for convenience of description and does not require any particular orientation of the item described.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A process for preparing a pharmaceutical dosage unit tablet core, the process comprising:
   (1) blending a particulate pharmaceutical active drug, an intragranular filler, an intragranular disintegrant and an intragranular lubricant to form a pre-blend, wherein the particulate pharmaceutical drug active has a particle size D[v, 0.5] of from about 25 µm to about 65 µm, from about 25 µm to about 50 µm, or from about 30 µm to about 40 µm;
   (2) compacting the pre-blend by application of a compaction force of from about 1 kN/cm to about 8 kN/cm, from about 2 kN/cm to about 5 kN/cm, or from about 2 kN/cm to about 4 kN/cm;
   (3) milling and screening the compacted pre-blend to form granules; and
   (4) tableting the granules by application of a tableting compression force of from about 5 kN to about 20 kN, from about 14 kN to about 19 kN, from about 14 kN to about 18 kN, or from about 8 kN to about 13 kN to form the pharmaceutical dosage unit tablet core, wherein the particulate pharmaceutical active drug is cobimetinib hemifumarate polymorph Form A.

2. The process of claim 1, wherein the pharmaceutical active drug has a particle size D[v, 0.9] of from about 45 µm to about 500 µm, from about 45 µm to about 400 µm, from about 45 µm to about 300 µm, from about 45 µm to about 200 µm, from about 45 µm to about 100 µm, from about 50 µm to about 60 µm, from about 65 µm to about 100 µm, from about 45 µm to about 80 µm, or from about 75 µm to about 100 µm.

3. The process of claim 1, further comprising applying a film coating on the surface of the pharmaceutical dosage unit tablet core.

4. The process of claim 1, further comprising, prior to tableting, blending the granules with extragranular disintegrant and extragranular lubricant to form a final blend, wherein the final blend is tableted.

5. The process of claim 1, wherein the total lubricant content based on pharmaceutical dosage unit tablet core weight is from about 0.5 wt. % to about 5 wt. %, from about 0.5 wt. % to about 3 wt. %, from about 1 wt. % to about 3 wt. %, from about 1 wt. % to about 2.5 wt. %, or from about 1.5 wt. % to about 2 wt. %.

6. The process of claim 4, wherein
   (1) the intragranular lubricant content based on tablet core weight is from about 0.1 wt. % to about 1 wt. %, from about 0.2 wt. % to about 0.75 wt. %, or from about 0.25 wt. % to about 5 wt. %; and
   (2) the extragranular lubricant content based on tablet core weight is from about 0.5 wt. % to about 2.5 wt. %, from about 0.75 wt. % to about 2.25 wt. %, from about 0.75 wt. % to about 2 wt. %, from about 1 wt. % to about 1.75 wt. %, or from about 1.25 wt. % to about 1.5 wt. %.

7. The process of claim 1, wherein the total disintegrant content based on pharmaceutical dosage unit tablet core weight is from about 2 wt. % to about 7 wt. %, from about 2 wt. % to about 6 wt. %, from about 2 wt. % to about 5 wt. %, from about 3 wt. % to about 6 wt. %, or from about 3 wt. % to about 5 wt. %.

8. The process of claim 1, wherein the pharmaceutical dosage unit tablet core comprises intragranular disintegrant and extragranular disintegrant, wherein
    (1) the intragranular disintegrant content based on tablet core weight is from about 0.1 wt. % to about 3 wt. %, from about 0.25 wt. % to about 2.5 wt. %, from about 0.25 wt. % to about 2 wt. %, from about 0.25 wt. % to about 1.5 wt. %, from about 0.25 wt. % to about 1 wt. %, from about 0.5 wt. % to about 3 wt. %, from about 0.5 wt. % to about 2 wt. %, from about 0.5 wt. % to about 1.5 wt. %, from about 1 wt. % to about 3 wt. %, or from about 1.5 wt. % to about 2.5 wt. %; and
    (2) the extragranular disintegrant content based on tablet core weight is from about 0.5 wt. % to about 3 wt. %, from about 1 wt. % to about 3 wt. %, from about 1.25 wt. % to about 3 wt. %, from about 1.25 wt. % to about 2.5 wt. %, from about 1.25 wt. % to about 2 wt. %, from about 1.25 wt. % to about 1.5 wt. %, from about 1.5 wt. % to about 3 wt. %, or from about 1.5 wt. % to about 2.5 wt. %.

9. The process of claim 8, wherein the weight ratio of the intragranular disintegrant to the extragranular disintegrant is about 1:5, about 1:3, about 1:1, or about 2:1.

10. The process of claim 1, wherein the total filler content based on pharmaceutical dosage unit tablet core weight is from about 60 wt. % to about 78 wt. %, from about 65 wt. % to about 78 wt. %, from about 65 wt. % to about 77 wt. %, from about 70 wt. % to about 77 wt. %, or from about 71 wt. % to about 75 wt. %.

11. The process of claim 1, wherein the bulk density of the final blend is from about 0.4 g/mL to about 0.75 g/mL, from about 0.45 g/mL to about 0.7 g/mL, or from about 0.5 g/mL to about 0.65 g/mL.

12. The process of claim 1, wherein the screen size is from about 0.5 mm to about 2.0 mm, from about 0.5 mm to about 1.5 mm, from about 0.5 mm to about 1.25 mm, from about 0.75 mm to about 2.0 mm, from about 0.75 mm to about 1.5 mm, from about 0.75 mm to about 1.25 mm, or about 1 mm.

13. The process of claim 1, wherein the filler comprises (1) lactose or (2) lactose and microcrystalline cellulose wherein the weight ratio of lactose to microcrystalline cellulose is from about 1:1.5 to about 4:1, from about 1.25 to about 4:1, from about 1:1 to about 4:1, from about 1:1 to about 3:1, from about 1.5:1 to about 3:1, or from about 2:1 to about 2.5:1.

14. The process of claim 1, wherein the disintegrant comprises sodium starch glycolate, croscarmellose sodium, or a combination thereof.

15. The process of claim 1, wherein the lubricant comprises magnesium stearate, sodium stearyl fumarate, or a combination thereof.

16. The process of claim 1, wherein the pre-blend further comprises a binder at a total binder content based on pharmaceutical dosage unit tablet core weight of from about 1 wt. % to about 10 wt. %, from about 1 wt. % to about 7 wt. %, from about 1 wt. % to about 6 wt. %, or from about 1 wt. % to about 5 wt. %.

17. The process of claim 16, wherein the binder comprises povidone, copovidone, pregelatinized starch, hydroxypropyl methylcellulose, or a combination thereof.

18. The process of claim 1, wherein the particulate pharmaceutical active drug content based on the weight of the tablet core is at least 5 wt. %, from about 15 wt. % to about 25 wt. %, or about 20 wt. %.

19. The process of claim 1, wherein the pharmaceutical dosage unit tablet core comprises:
    (1) from 17.6 wt. % to 19.4 wt. % cobimetinib hemifumarate polymorph Form A;
    (2) from 43.3 wt. % to 47.9 wt. % microcrystalline cellulose;
    (3) from 28.9 wt. % to 31.9 wt. % lactose monohydrate;
    (4) from 3.8 wt. % to 4.2 wt. % croscarmellose sodium; and
    (5) from 1.4 wt. % to 1.6 wt. % magnesium stearate.

20. The process of claim 1, wherein the pre-blend is compacted between at least two rotating rolls having a gap width of from about 2 mm to about 5 mm, from about 2 mm to about 4 mm, from about 3 mm to about 5 mm, or from about 4 mm to about 5 mm to form a ribbon, wherein the ribbon is milled and screened to form granules.

21. The process of claim 20, wherein the ribbon has an at-gap density selected from:
    from about 0.85 g/mL to about 0.95 g/mL from about 0.9 g/mL to about 0.95 g/mL, from about 0.95 g/mL to about 1.1 g/mL, from about 0.95 g/mL to about 1.05 g/mL, from about 1 g/mL to about 1.10 g/mL, from about 1 g/mL to about 1.05 g/mL, from about 1.1 g/mL to about 1.3 g/mL, from about 1.1 g/mL to about 1.25 g/mL, from about 1.1 g/mL to about 1.2 g/mL, from about 1.1 g/mL to about 1.15 g/mL, from about 1.15 g/mL to about 1.3 g/mL, from about 1.15 g/mL to about 1.25 g/mL, and from about 1.15 g/mL to about 1.2 g/mL.

22. The process of claim 20, wherein the particulate pharmaceutical active drug has a particle size D[v, 0.5] of from about 27 μm to about 37 μm, the roller compaction gap force is about 2 kN/cm, and the gap width is about 5 mm.

23. The process of claim 20, wherein the particulate pharmaceutical active drug has a particle size D[v, 0.5] of from about 38 μm to about 65 μm, the roller compaction gap force is from about 2 kN/cm to about 4 kN/cm, and the gap width is from about 4 mm to about 5 mm.

24. A pharmaceutical dosage unit tablet core, the tablet core comprising:
    (1) about 5 wt. % or more of a particulate pharmaceutical active drug;
    (2) a lubricant at a content based on the pharmaceutical dosage unit tablet core weight of from about 0.5 wt. % to about 5 wt. %, from about 0.5 wt. % to about 3 wt. %, from about 1 wt. % to about 3 wt. %, from about 1 wt. % to about 2.5 wt. %, or from about 1.5 wt. % to about 2 wt. %;
    (3) a disintegrant at a content based on the pharmaceutical dosage unit tablet core weight of from about 2 wt. % to about 7 wt. %, from about 2 wt. % to about 6 wt. %, from about 2 wt. % to about 5 wt. %, from about 3 wt. % to about 6 wt. %, or from about 3 wt. % to about 5 wt. %;
    (4) a filler at a content based on the pharmaceutical dosage unit tablet core weight of from about 60 wt. % to about 78 wt. %, from about 65 wt. % to about 78 wt. %, from about 65 wt. % to about 77 wt. %, from about 70 wt. % to about 77 wt. %, or from about 71 wt. % to about 75 wt. %; and
    (5) optionally, up to 10 wt. % of a binder, wherein the particulate pharmaceutical active drug is cobimetinib hemifumarate polymorph Form A.

25. The pharmaceutical dosage unit tablet core of claim 24, wherein the particulate pharmaceutical active drug content based on the weight of the tablet core is from about 15 wt. % to about 25 wt. %, or about 20 wt. %.

26. The pharmaceutical dosage unit tablet core of claim 24, wherein the particulate pharmaceutical active drug has a particle size D[v, 0.5] of from about 25 μm to about 65 μm, from about 25 μm to about 50 μm, or from about 30 μm to about 40 μm.

27. The pharmaceutical dosage unit tablet core of claim 24, wherein the particulate pharmaceutical active drug has a particle size D[v, 0.5] of from about 45 μm to about 500 μm, from about 45 μm to about 400 μm, from about 45 μm to about 300 μm, from about 45 μm to about 200 μm, from about 44 μm to about 100 μm, from about 50 μm to about 60 μm, from about 65 μm to about 100 μm, from about 45 μm to about 80 μm, or from about 75 μm to about 100 μm.

28. The pharmaceutical dosage unit tablet core of claim 24, wherein said tablet core comprises intragranular lubricant and extragranular lubricant, wherein:
(1) the intragranular lubricant content based on said tablet core weight is from about 0.1 wt. % to about 1 wt. %, from about 0.2 wt. % to about 0.75 wt. %, or from about 0.25 wt. % to about 5 wt. %; and
(2) the extragranular lubricant content based on said tablet core weight is from about 0.5 wt. % to about 2.5 wt. %, from about 0.75 wt. % to about 2.25 wt. %, from about 0.75 wt. % to about 2 wt. %, from about 1 wt. % to about 1.75 wt. %, or from about 1.25 wt. % to about 1.5 wt. %.

29. The pharmaceutical dosage unit tablet core of claim 24, wherein the lubricant comprises magnesium stearate, sodium stearyl fumarate, or a combination thereof.

30. The pharmaceutical dosage unit tablet core of claim 24, wherein said tablet core comprises intragranular disintegrant and extragranular disintegrant, wherein:
(1) the intragranular disintegrant content based on said tablet core weight is from about 0.1 wt. % to about 3 wt. %, from about 0.25 wt. % to about 2.5 wt. %, from about 0.25 wt. % to about 2 wt. %, from about 0.25 wt. % to about 1.5 wt. %, from about 0.25 wt. % to about 1 wt. %, from about 0.5 wt. % to about 3 wt. %, from about 0.5 wt. % to about 2 wt. %, from about 0.5 wt. % to about 1.5 wt. %, from about 1 wt. % to about 3 wt. %, or from about 1.5 wt. % to about 2.5 wt. %; and
(2) the extragranular disintegrant content based on said tablet core weight is from about 0.5 wt. % to about 3 wt. %, from about 1 wt. % to about 3 wt. %, from about 1.25 wt. % to about 3 wt. %, from about 1.25 wt. % to about 2.5 wt. %, from about 1.25 wt. % to about 2 wt. %, from about 1.25 wt. % to about 1.5 wt. %, from about 1.5 wt. % to about 3 wt. %, or from about 1.5 wt. % to about 2.5 wt. %.

31. The pharmaceutical dosage unit tablet core of claim 30, wherein the weight ratio of the intragranular disintegrant to the extragranular disintegrant is about 1:5, about 1:3, about 1:1, or about 2:1.

32. The pharmaceutical dosage unit tablet core of claim 24, wherein the disintegrant comprises sodium starch glycolate, croscarmellose sodium, or a combination thereof.

33. The pharmaceutical dosage unit tablet core of claim 24, wherein the filler comprises (1) lactose or (2) lactose and microcrystalline cellulose, wherein the weight ratio of lactose to microcrystalline cellulose is from about 1:1.5 to about 4:1, from about 1:1.25 to about 4:1, from about 1:1 to about 4:1 from about 1:1 to about 3:1, from about 1.5:1 to about 3:1, or from about 2:1 to about 2.5:1.

34. The pharmaceutical dosage unit tablet core of claim 24, wherein the particulate pharmaceutical active drug has a particle size D[v, 0.5] of from about 25 μm to about 40 μm.

35. The pharmaceutical dosage unit tablet core of claim 24, wherein the particulate pharmaceutical active drug has a particle size D[v, 0.5] of from about 40 μm to about 65 μm.

36. The pharmaceutical dosage unit tablet core of claim 24, wherein the tablet core further comprises a binder at a total binder content based on said tablet core weight of from about 1 wt. % to about 10 wt. %, from about 1 wt. % to about 7 wt. %, from about 1 wt. % to about 6 wt. %, or from about 1 wt. % to about 5 wt. %.

37. The pharmaceutical dosage unit tablet core of claim 36, wherein the binder comprises povidone, copovidone, pregelatinized starch, hydroxypropyl methylcellulose, or a combination thereof.

38. The pharmaceutical dosage unit tablet core of claim 24, wherein said tablet core comprises:
(1) from about 17.6 wt. % to about 19.4 wt. % cobimetinib hemifumarate polymorph Form A;
(2) from about 43.3 wt. % to about 47.9 wt. % microcrystalline cellulose;
(3) from about 28.9 wt. % to about 31.9 wt. % lactose monohydrate;
(4) from about 3.8 wt. % to about 4.2 wt. % croscarmellose sodium; and
(5) from about 1.4 wt. % to about 1.6 wt. % magnesium stearate.

39. The pharmaceutical dosage unit tablet core of claim 24, further comprising a film-coating on the surface of said tablet core, wherein the coated pharmaceutical dosage unit tablet core is characterized by:
(1) a dissolution profile such that 80% of the tablet dissolves in 20 minutes;
(2) a minimum hardness of 45 N;
(3) a disintegration time of no more than 300; and
(4) an abrasion of less than 1.0%.

40. The pharmaceutical dosage unit tablet core of claim 39, wherein the coated pharmaceutical dosage unit tablet core comprises from about 2 wt. % to about 6 wt. % or from about 3 wt. % to about 5 wt. % of the film-coating based on the weight of said tablet core, and, wherein the film-coating comprises:
(1) from about 38 wt. % to about 42 wt. % polyvinyl alcohol;
(2) from about 23.8 wt. % to about 26.3 wt. % titanium dioxide;
(3) from about 19.2 wt. % to about 21.2 wt. % macrogol/PEG3350; and
(4) from about 14.1 wt. % to about 15.5 wt. % talc.

41. A pharmaceutical product comprising:
(1) a first tablet comprising the coated pharmaceutical dosage unit tablet core of claim 39; and
(2) a second tablet comprising propane-1-sulfonic acid {3-[5-(4-chlorophenyl)-1H-pyrrolo[2,3-b]pyridine-3-carbonyl]-2,4-difluoro-phenyl}-amide (vemurafenib), or a pharmaceutically acceptable salt thereof.

42. The pharmaceutical product of claim 41, wherein the first tablet comprises 20 mg cobimetinib, 40 mg cobimetinib, or 60 mg cobimetinib.

43. A method of treating BRAFV600 mutation-positive unresectable or metastatic melanoma comprising administering to a patient a therapeutically effective amount of the pharmaceutical product of claim 41.

44. The method of claim 43, wherein one or more first tablets are administered to provide a total dose of 60 mg cobimetinib, on days 1-21 of a 28 day cycle, and wherein one or more second tablets are administered to provide a total dose of 960 mg vemurafenib, twice daily each day of the 28 day cycle.

45. The method of claim 43, wherein the first tablet is administered sequentially with the second tablet.

46. The method of claim 43, wherein the first tablet is administered concurrently with the second tablet.

47. The method of claim 43, wherein the unresectable or metastatic melanoma is BRAFV600E mutation-positive melanoma.

48. The method of claim 43, wherein the unresectable or metastatic melanoma is metastatic melanoma.

49. The method of claim 43, wherein the BRAFV600 mutation-positive unresectable or metastatic melanoma has not been previously treated.

50. A pharmaceutical dosage unit tablet core, the tablet core comprising:
   (1) 18.5 wt. % cobimetinib hemifumarate polymorph Form A;
   (2) 45.6 wt. % microcrystalline cellulose;
   (3) 30.4 wt. % lactose monohydrate;
   (4) 4 wt. % croscarmellose sodium; and
   (5) 1.5 wt. % magnesium stearate.

51. The pharmaceutical dosage unit tablet core of claim 50, comprising:
   (1) 2 wt. % intragranular croscarmellose sodium and 2 wt. % extragranular croscarmellose sodium; and
   (2) 0.25 wt. % intragranular magnesium stearate and 1.25 wt. % extragranular magnesium stearate.

52. The pharmaceutical dosage unit tablet core of claim 50, wherein the microcrystalline cellulose has a bulk density from 0.26 to 0.31 g/mL, a degree of polymerization of not more than 350, and a particle size measured by air jet of not more than 1 wt. %+60 mesh (250 microns) and not more than 30 wt. %+200 mesh (75 microns).

53. A coated pharmaceutical dosage unit tablet core, the coated tablet comprising:
   (1) 17.79 wt. % cobimetinib hemifumarate polymorph Form A;
   (2) 43.85 wt. % microcrystalline cellulose;
   (3) 29.23 wt. % lactose monohydrate;
   (4) 3.84 wt. % croscarmellose sodium;
   (5) 1.45 wt. % magnesium stearate; and
   (6) 3.85 wt. % film coating.

54. The coated pharmaceutical dosage unit tablet of claim 53, comprising:
   (1) 1.92 wt. % intragranular croscarmellose sodium and 1.92 wt. % extragranular croscarmellose sodium; and
   (2) 0.24 wt. % intragranular magnesium stearate and 1.21 wt. % extragranular magnesium stearate.

55. The coated pharmaceutical dosage unit tablet of claim 53, wherein the film coating comprises:
   (1) 40 wt. % polyvinyl alcohol;
   (2) 25 wt. % titanium dioxide;
   (3) 20.2 wt. % macrogol/PEG 3350; and
   (4) 14.8 wt. % talc.

56. A pharmaceutical product comprising:
   (1) a first tablet comprising the coated tablet of claim 53; and
   (2) a second tablet comprising propane-1-sulfonic acid {3-[5-(4-chlorophenyl)-1H-pyrrolo[2,3-b]pyridine-3-carbonyl]-2,4-difluoro-phenyl}-amide (vemurafenib), or a pharmaceutically acceptable salt thereof.

57. The pharmaceutical product of claim 56, wherein the first tablet comprises 20 mg cobimetinib, 40 mg cobimetinib, or 60 mg cobimetinib.

58. A method of treating BRAFV600 mutation-positive unresectable or metastatic melanoma comprising administering to a patient a therapeutically effective amount of the pharmaceutical product of claim 56.

59. The method of claim 58, wherein one or more first tablets are administered to provide a total dose of 60 mg cobimetinib, on days 1-21 of a 28 day cycle, and wherein one or more second tablets are administered to provide a total dose of 960 mg vemurafenib, twice daily each day of the 28 day cycle.

60. The method of claim 58, wherein the first tablet is administered sequentially with the second tablet.

61. The method of claim 58, wherein the first tablet is administered concurrently with the second tablet.

62. The method of claim 58, wherein the unresectable or metastatic melanoma is BRAFV600E mutation-positive melanoma.

63. The method of claim 58, wherein the unresectable or metastatic melanoma is metastatic melanoma.

64. The method of claim 58, wherein the BRAFV600 mutation-positive unresectable or metastatic melanoma has not been previously treated.

65. A process for preparing a coated pharmaceutical dosage unit tablet, the process comprising the following steps:
   (1) combining a particulate filler component, a first particulate disintegrant component and cobimetinib hemifumarate polymorph Form A in a blender and admixing said components to form a primary pre-blend;
   (2) combining a particulate first lubricant component with the primary pre-blend in a blender and admixing said first lubricant component and primary pre-blend to form a finished preblend;
   (3) dry granulating the finished pre-blend to form granules;
   (4) combining the granules and a second particulate disintegrant component in a blender and admixing said granules and disintegrant component to form a primary final blend;
   (5) combining a second particulate lubricant component and the primary final blend in a blender and admixing said second lubricant component and primary final blend to form a finished final blend;
   (6) tableting the finished final blend to form tablet cores; and
   (7) coating the tablet cores.

66. The process of claim 65, further comprising suspending a film-coat solid mixture in water to form a coating slurry mixture and coating the tablet cores with the coating mixture slurry.

67. The process of claim 65, wherein:
   (1) the particulate filler component is selected from lactose, microcrystalline cellulose, and combinations thereof;
   (2) the first particulate disintegrant and second particulate disintegrant are each selected from sodium starch glycolate, croscarmellose sodium, and combinations thereof; and
   (3) first lubricant component and the second lubricant component are each selected from magnesium stearate, sodium stearyl fumarate, and combinations thereof.

* * * * *